US006287840B1

United States Patent
Palmer et al.

(12)

(10) Patent No.: US 6,287,840 B1
(45) Date of Patent: Sep. 11, 2001

(54) IRREVERSIBLE CYSTEINE PROTEASE INHIBITORS CONTAINING VINYL GROUPS CONJUGATED TO ELECTRON WITHDRAWING GROUPS

(75) Inventors: James T. Palmer, San Ramon; David Rasnick, San Francisco; Jeffrey Lee Klaus, Redwood City, all of CA (US)

(73) Assignee: Axys Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/376,267

(22) Filed: Aug. 18, 1999

Related U.S. Application Data

(63) Continuation of application No. 08/700,518, filed as application No. PCT/US95/02252 on Feb. 24, 1995, now Pat. No. 5,976,858, which is a continuation of application No. 08/202,051, filed on Feb. 25, 1994, now abandoned.

(51) Int. Cl.[7] .............................. C12N 9/50; C12N 9/99; A61K 38/03
(52) U.S. Cl. .......................... 435/219; 435/184; 514/18; 514/19
(58) Field of Search .................................. 435/219, 184; 514/18, 19

(56) References Cited

U.S. PATENT DOCUMENTS

| | | |
|---|---|---|
| 4,518,528 | 5/1985 | Rasnick . |
| 5,037,957 | 8/1991 | Grubb et al. . |
| 5,055,451 | 10/1991 | Krantz . |
| 5,101,068 | 3/1992 | Palmer . |
| 5,374,623 | 12/1994 | Zimmerman et al. . |
| 5,585,368 | 12/1996 | Steinmeyer et al. . |

FOREIGN PATENT DOCUMENTS

| | | |
|---|---|---|
| 4-202170 | 4/1992 | (JP) . |
| 4-273896 | 9/1992 | (JP) . |
| 4-273897 | 9/1992 | (JP) . |
| 5-213990 | 8/1993 | (JP) . |
| 93/14777 | 8/1993 | (WO) . |
| 93/16710 | 9/1993 | (WO) . |
| 94/04172 | 3/1994 | (WO) . |

OTHER PUBLICATIONS

Hanzlik et al., "Vinylogous Amino Acid Esters: A New Class of Inactivators for Thiol Proteases," *Journal of Medicinal Chemistry*, vol. 27, No. 6:711–712 (1984).

Thompson et al., "Carboxyl–Modified Amino Acids and Peptides as Protease Inhibitors," *J. Med. Chem.*, 29:104–111 (1986).

Liu and Hanzlik, "Structure–Activity Relationships for Inhibition of Papain by Peptide Michael Acceptors," *J. Med. Chem.*, 35(6):1067–1075 (1992).

Rawlings et al., "Evolutionary Families of Peptidases," *J. Biochem.*, 290:205–218 (1993).

Walker et al., "Peptidylmethyl Sulfonium Salts, A New Class of Thiol Protease Inactivators," *Protease Inhibitors*, p. 1433 (Abstract No. 5975).

Fehrentz et al., "An Efficient Synthesis of Optically Active α–(t–Butoxycarbonylamino)–aldehydes from α–Amino Acids," *Communications*, pp. 676–678 (1983)

Mehdi, "Synthetic and Naturally Occurring Protease Inhibitors Containing and Electrophilic Carbonyl Group,"*Bioorganic Chemistry*, 21:249–259 (1993).

Wadsworth et al., "The Utility of Phosphonate Carbanions Olefin Synthesis," [Contribution from Rohm and Haas Co., Philadlphia 37, Penna,], 83:1733–1738 (1961).

Brömme et al., "Novel–N–peptidyl–O–acyl Hydroxamates: Selective Inhibitors of Cysteine Proteinases," *Biochimica et Biophysica Acta.*, 1202:271–276 (1993).

Rosenthal et al., "Antimalarial Effects of Peptide Inhibitors of a Plasmodium Falciparum Cysteine Proteinase," *J. Clin. Invest.*, 88:1467–1472 (1991).

Rasnick, "Synthesis of Peptide Fluormethyl Ketones and the Inhibition of Human Cathepsin B," *Analytical Biochemistry*, 149:461–465 (1985).

Kirschke et al., "Rapid Inactivation of Cathepsin L by Z–Phe–Phechn$^1_2$ and Z–Phe–Alachn$_2$, " *Biochemical and Biophysical Reasearch Communications*, 101(2):454–458 (1981).

Krantz et al., "Peptidyl (Acyloxy)methyl Ketones and the Quiescent Affinity Label Concept: The Departing Group as a Variable Structural Element in the Design of Inactivators of Cysteine Proteinases," *Biochemistry*, 30:4678–4687 (1991).

Hanada et al., "Isolation and Characterization of E–64, A New Thiol Protease Inhibitor," *Agric. Biol. Chem.*, 42(3):523–528 (1978).

Sumiya et al., "Molecular Design of Potent Inhibitor Specific for Cathepsin B Based on the Tertiary Structure Prediction," *Chem. Parm. Bul.*, 40(2):299–303 (1992).

Gour–Salin et al., "Epoxysuccinyl Dipeptides as Selective Inhibitors of Cathepsin B," *J. Med. Chem.*, 36:720–725 (1993).

(List continued on next page.)

Primary Examiner—Jon P. Weber
(74) Attorney, Agent, or Firm—Robin M. Silva, Esq.; Flehr Hohbach Test Albritton & Herbert LLP

(57) ABSTRACT

Irreversible cysteine protease inhibitors based upon an alkene bond being conjugated to an electron withdrawing group are disclosed. The inhibitor structure also provides a targeting peptide which is specific for different cysteine proteases. The method of making the inhibitors, and methods of using the inhibitors to inhibit cysteine proteases and for therapy are disclosed.

32 Claims, No Drawings

OTHER PUBLICATIONS

Barrett et al., "Proteinase Inhibitors," Chapter 4, pp. 154–177, in Dingle et al., *Research Monographs in Cell and Tissue Physiology*, vol. 12, Elsevier (1986).

Shaw, "Cysteinyl Proetinases and Their Selective Inactivation," *Advances in Enzymology and Related Areas of Molecular Biology*, 63:271–347 (1990).

Anderson et al., "Nucleophilic an Electrophilic Mercaptanylations via 2–(Trimethylsilyl) ethanethiol–Derived Reagenst," *J. Org. Chem.*, 53:3125–3127 (1988).

Spaltenstein et al., "New Approaches to the Syntheis of trans–ALkene Isosteres of Dipeptides," *J. Org. Chem.*, 52:3759–3766 (1987).

McIlwain, "Amino–Suphonic Acid Analogues of Natural Amino–Carboxylic Acids," Department of Bacterial Chemistry (Medical Research Counsil), Bland Sutton Institute of Pathology and the Courtauld Institute of Biochemistry, pp. 75–77 (1941).

Engberts et al., "The Mannich Condensation of Sulfinic Acids, Aldehyde, and Ethyl Carbamate," *Recueil*, 84:942–950 (1965).

Esser, "Cysteine Proteinase Inhibitors Decrease Articular Cartilage and Bone Destruction in Chronic Inflammatory Arthritis," *Arthritis & Rheumatism*, 37(2):236–247 (1994).

Sebti et al., "Metabolic Inactivation: A Mechanism of Human Tumor Resistance to Bleomycin," *Cancer Res.*, pp. 227–232 (Jan. 1991).

Reetz et al., "Stereoselective Nucleophilic Addition Reactions of Reactive Pseudopeptides," *Angew. Chem. Int. Ed. Engl.*, 31(12):1626–1629 (1992).

Meng and Hesse, "Synthetic Approaches toward Gildobamine, the Core Structure of the Glidobactin Antibiotics," *Tetrahedron*, 47(32):6251–6264 (1991).

Kolter et al., "Configuaratively Stable Dipeotude Aldehydes from D–Glucosamine Hydrochloride," *Angew. Chem. Int. Ed. Engl.*, 31(10):1391–1392 (1992).

Smith et al., "Synthesis and Renin Inhibitory Activity of Angiotensinogen Analogues Having Dehydrostatine Leuψ[Ch$_2$S] Val, of Leuψ[Ch$_2$SO] Val at the P$_1$–P$_1$' Cleavage Site," *J. Med. Chem.*, 31:1377–1382 (1988).

Barton et al., "Synthesis of Novel α–Amino–Acids and Derivatives Using Radical Chemistry; Synthesis of L– And D–α–Amino–Adipic Acids, L–α–Aminopimelic Acid and Appropriate Unsaturated Derivatives," *Tetrahedron*, 43(19):4297–4308 (1987).

Hagihara and Schreiber, "Reassignment of Stereochemistry and Total Synthesis of the Thrombin Inhibitor Cyclotheonamide B," *J. Am. Chem. Soc.*, 114:6570–6571 (1992).

Maryanoff et al., "Molecular Basis for the Inhibition of Human α–thrombin by the Macrocyclic Peptide Cyclothenamide A," *Proc. Natl. Acad. Sci. USA*, 90:8048–8052 (1993).

Rich et al., "Synthesis of Analogues of the Carboxyl Protease Inhibitor Pepstatin. Effect of Structure on Inhibition of Pepsin and Renin," *J. Med. Chem.*, 23:27–33 (1980).

Brillon et al., *J. Org. Chem.*, 57:1838–1842 (1992).

Takaaki et al., "Structures and Activities of Protease Inhibitors of Microbial Origin," *Chemical Abstracts*, 85:145, Abstract No. 1676 (1975).

Morgan et al., "Synthesis and Pharmacology of Dipeptides Related to des [Gly$^3$] Enkaphalin: Modification of the C–Terminal Amide," *Chemical Abstracts*, 106:650, Abstract No. 85020 (1985).

Boden et al., "Rationally Designed 'Dipeptoid' Analogues of Cholecystokinin (CCK): C–Terminal Structure–Activity Relationships of α–methyl Tryptophan Derivatives," *Eur. J. Med. Chem.*, 28:47–61 (1993).

Liu et al., "Teh Contribution of Intermolecular Hydrogen Bonding to the Kinetic Specificity of Papain," *Biochim. Biophys. Acta.*, 1158(3):264–272 (1993).

Liu et al., "Effects of Homologetaion an dLigand Reactivity on the Apparent Kinetic Specificity of Papsin," *Biochim. Biophys. Acta.*, 1250(3):43–48 (1995).

IRREVERSIBLE CYSTEINE PROTEASE INHIBITORS CONTAINING VINYL GROUPS CONJUGATED TO ELECTRON WITHDRAWING GROUPS

CROSS-REFERENCE TO RELATED APPLICATIONS

This application is a continuation of U.S. application Ser. No. 08/700,518, filed Aug. 23, 1996, which issued as U.S. Pat. No. 5,976,858, Nov. 2, 1999, which is a national phase entry of PCT/US95/02252, filed Feb. 24, 1995, which is a continuation of U.S. application Ser. No. 08/202,051 filed Feb. 25, 1994, abandoned.

FIELD OF THE INVENTION

The invention relates to novel cysteine protease inhibitors. The inhibitors are specific to cysteine proteases and do not inhibit serine, aspartyl or zinc protease.

BACKGROUND OF THE INVENTION

Cysteine or thiol proteases contain a cysteine residue at the active site responsible for proteolysis. Since cysteine proteases have been implicated in a number of diseases, including arthritis, muscular dystrophy, inflammation, tumor invasion, glomerulonephritis, malaria, and other parasite-borne infections, methods for selectively and irreversibly inactivating them provide opportunities for new drug candidates. See, for example, Meijers, M. H. M. et al., Agents Actions (1993), 39 (Special Conference Issue), C219; Machleidt, W. et al, Fibrinolysis (1992), 6 Suppl. 4, 125; Sloane, B. F. et al., Biomed. Biochim. Acta (1991), 50, 549; Duffy, M. J., Clin. Exp. Metastasis (1992), 10, 145; Rosenthal, P. J., Wollish, W. S., Palmer, J. T., Rasnick, D., J. Clin. Investigations (1991), 88, 1467; Baricos, W. H. et al, Arch. Biochem. Biophys. (1991), 288, 468; Thornberry, N. A. et al., Nature (1992), 356, 768.

Low molecular weight inhibitors of cysteine proteases have been described by Rich, Proteinase Inhibitors (Chapter 4, "Inhibitors of Cysteine Proteinases"), Elsevier Science Publishers (1986). Such inhibitors include peptide aldehydes, which form hemithioacetals with the cysteine of the protease active site. The disadvantage of aldehydes is their in vivo and chemical instabilities.

Aldehydes have been transformed into α,β-unsaturated esters and sulfones by means of the Wadsworth-Emmons-Horner modification of the Wittig reaction (Wadsworth, W. S. and Emmons, W. D. (J. Am. Chem. Soc. (1961), 83, 1733: Equation 1).

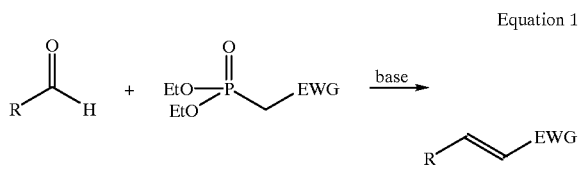

Equation 1 where
R=alkyl, aryl, etc.
EWG=COOEt, SO$_2$Me, etc.

α,β-unsaturated esters (Hanzlik et al., J. Med. Chem., 27(6):711–712 (1984), Thompson et al., J. Med. Chem. 29:104–111 (1986), Liu et al., J. Med. Chem., 35(6):1067 (1992)) and an α,β-unsaturated sulfones (Thompson et al., supra, Liu et al., supra) were made using this method and tested as inhibitors of two cysteine proteases, papain and dipeptidyl amino-peptidase I (also called cathepsin C). However, the inhibition of papain by these α,β-unsaturated compounds showed poor inhibition, evidenced by second order rate constants from less than 1 M$^{-1}$sec$^{-1}$ to less than 70 M$^{-1}$sec$^{-1}$ for the α,β-unsaturated esters, and from less than 20 M$^{-1}$sec$^{-1}$ to less than 60 M$^{-1}$sec$^{-1}$ for the sulfone.

In addition, this chemistry has not been demonstrated with derivatives of α-amino acids other than those corresponding to glycine, or in the case of the ester, phenylalanine. Thus the chirality of these compounds is non-existent for the glycine derivatives and unclear for the phenylalanine derivatives. This is significant since inhibition of an enzyme generally requires a chiral compound.

Additional methods for selectively and irreversibly inhibiting cysteine proteases have relied upon alkylation by peptide α-fluoromethyl ketones (Rasnick, D., Anal. Biochem. (1985), 149, 416), diazomethylketones (Kirschke, H., Shaw, E. Biochem. Biphys. Res. Commun. (1981), 101, 454), acyloxymethyl ketones (Krantz, A. et al., Biochemistry, (1991), 30, 4678; Krantz, A. et al., U.S. Pat. No. 5,055,451, issued Oct. 8, 1991), and ketosulfonium salts (Walker, B., Shaw, E., Fed. Proc. Fed. Am. Soc. Exp. Biol., (1985), 44, 1433). The proposed mechanism of inactivation relies upon irreversible inactivation of the active site thiol group via alkylation, as depicted in Equation 2.

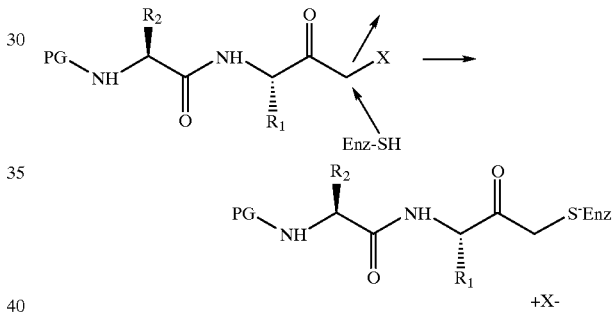

Equation 2 where
PG=protecting group
R$_1$, R$_2$=amino acid side chains
X=Cl, F, N$_2$, OC(O)R, (+)S(CH$_3$)$_3$ Other families of cysteine protease inhibitors include epoxysuccinyl peptides, including E-64 and its analogs (Hanada, K. et al., Agric. Biol. Chem (1978), 42, 523; Sumiya, S. et al., Chem. Pharm. Bull. ((1992), 40, 299 Gour-Salin, B. J. et al., J. Med. Chem., (1993), 36, 720), α-dicarbonyl compounds, reviewed by Mehdi, S., Bioorganic Chemistry, (1993), 21, 249, and N-peptidyl-O-acyl hydroxamates (Bromme, D., Neumann, U., Kirschke, H., Demuth, H-U., Biochim. Biophys. Acta, (1993), 1202, 271.

SUMMARY OF THE INVENTION

It is an object of the present invention to provide novel cysteine protease inhibitors that function irreversibly, resulting in large second order rate constants for the overall inhibition reaction. Accordingly, it is an object to provide these novel cysteine protease inhibitors that can be used to inhibit cysteine proteases selectively, and are thus useful in a variety of therapeutic applications.

In accordance with the foregoing objects, the present invention provides cysteine protease inhibitors comprising a targeting group linked to an alkene bond electronically conjugated with an electron withdrawing group (EWG). The second order rate constant for inhibition of a cysteine protease with the inhibitor, expressed as $k_{irr}/K_I$, preferably is at least about 1000 $M^{-1}sec^{-1}$.

An additional aspect of the present invention is to provide chiral cysteine protease inhibitors comprising a targeting group linked to an alkene bond conjugated with an EWG. Additionally provided are these chiral cysteine protease inhibitors wherein the second order rate constant for inhibition of a cysteine protease with the inhibitor, expressed as $k_{irr}/K_I$, is at least about 1000 $M^{-1}sec^{-1}$.

In a further aspect of the present invention, a cysteine protease inhibitor is provided with the formula:

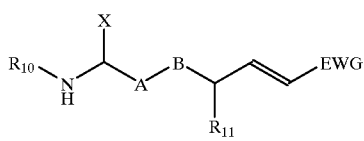

Formula 1

In this formula, $R_{10}$ is hydrogen, a peptide amino end blocking group, a peptide residue with or without an amino end blocking group, a single amino acid residue with or without an amino end blocking group or a label. X and $R_{11}$ are amino side chains, with either (R) or (S) configuration. The A—B linkage is a peptide or peptidomimetic linkage, and EWG is an electron withdrawing group. Also provided are cysteine protease inhibitors wherein the second order rate constant for inhibition of a cysteine protease with the inhibitor, expressed as $k_{irr}/K_I$, is at least about 1000 $M^{-1}sec^{-1}$.

Also provided are labelled cysteine protease inhibitors, and cysteine protease inhibitors that contain additional targeting groups linked to the EWG.

In a further aspect of the present invention, cysteine protease inhibitors are provided wherein the EWG is a moiety or group that will work in the Wadsworth-Emmons reaction for olefin synthesis when directly attached to a methylenephosphonate species. Thus the EWG group, when functionally included as a component of the cysteine protease inhibitor, may be selected from the group consisting of vinylogous esters, vinylogous sulfones, vinylogous carboxylates, vinylogous amides, vinylogous phosphonates, vinylogous ketones, vinylogous nitriles, vinylogous sulfoxides, vinylogous sulfonamides, vinylogous sulfinamides, vinylogous sulfonates and vinylogous sulfoximines.

An additional aspect of the present invention relates to methods for making a cysteine protease inhibitor. The method comprises: a) a protected α-amino aldehyde is coupled with a Wadsworth-Emmons reagent containing an EWG to form a cysteine protease inhibitor intermediate; b) the cysteine protease inhibitor intermediate is the n deprotected at the N-terminus; and c) the deprotected cysteine protease inhibitor intermediate is then coupled to N-terminally protected amino acids.

The invention also includes a method for inhibiting a cysteine protease, comprising irreversibly binding an cysteine protease inhibitor to the protease.

The invention further provides a method of treating cysteine proteane-associated disorders, comprising administering a therapeutically effective dose of a cysteine protease inhibitor to a patient. Thus, pharmaceutical compositions of cysteine protease inhibitors are also provided.

Additionally, the invention provides methods of detecting a cysteine protease in a sample, comprising assaying the sample in the presence and absence of a cysteine protease inhibitor of the present invention and calculating the difference in activity due to the protease.

Further provided are cysteine protease inhibitors with the formula:

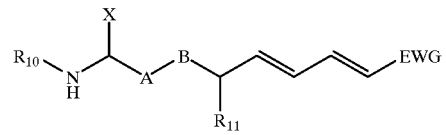

In this formula, $R_{10}$ is hydrogen, a peptide amino end blocking group, a peptide residue with or without an amino end blocking group, a single amino acid residue with or without an amino end blocking group, or a label. X and $R_{11}$ are amino side chains, with either (R) or (S) configuration. The A—B linkage is a peptide or peptidomimetic linkage, and EWG is an electron withdrawing group.

An additional aspect of the invention provides cysteine protease inhibitors with the formula:

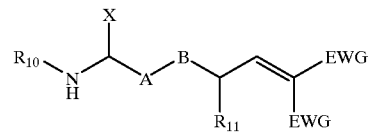

In this formula, $R_{10}$ is hydrogen, a peptide amino end blocking group, a peptide residue with or without an amino end blocking group, a single amino acid residue with or without an amino end blocking group or a label. X and $R_{11}$ are amino side chains, with either (R) or (S) configuration. The A—B linkage is a peptide or peptidomimetic linkage, and EWG is an electron withdrawing group.

DETAILED DESCRIPTION OF THE INVENTION

The present invention relates to novel cysteine protease inhibitors. It is believed that the inhibitors function to inactivate cysteine proteases based on the following mechanism:

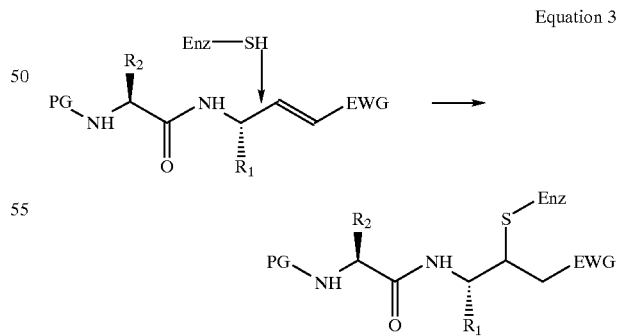

Equation 3

It is believed that the enzyme is thus irreversibly inhibited by 1,4 conjugate addition of the nucleophilic thiol group. This mechanism is thus distinguished from the alkylation mechanism depicted in Equation 2.

This mechanism permits specificity of the enzyme inhibitors for cysteine proteases over serine, aspartyl, and zinc proteases, by virtue of a different mechanism. The mechanisms of serine protease action have been described by Walsh, C., in "Enzymatic Reaction Mechanisms" pp. 94–97, W.H. Freeman and Co., San Francisco, 1979. The serine at the active site reacts with the carbonyl of the substrate, forming a tetrahedral intermediate. The inhibitors of this invention have no carbonyl at the site of nucleophilic attack, and are not susceptible to attack by serine proteases.

Cysteine proteases are a family of proteases that bear a thiol group at the active site. These proteases are found in bacteria, viruses, eukaryotic microorganisms, plants, and animals. Cysteine proteases may be generally classified as belonging to one of four or more distinct superfamilies. Examples of cysteine proteases that may be inhibited by the novel cysteine protease inhibitors of the present invention include, but are not limited to, the plant cysteine proteases such as papain, ficin, aleurain, oryzain and actinidain; mammalian cysteine proteases such as cathepsins B, H, J, L, N, S, T and C, (cathepsin C is also known as dipeptidyl peptidase I), interleukin converting enzyme (ICE), calcium-activated neutral proteases, calpain I and II; viral cysteine proteases such as picornian 2A and 3C, aphthovirus endopeptidase, cardiovirus endopeptidase, comovirus endopeptidase, potyvirus endopeptidases I and II, adenovirus endopeptidase, the two endopeptidases from chestnut blight virus, togavirus cysteine endopeptidase, as well as cysteine proteases of the polio and rhinoviruses; and cysteine proteases known to be essential for parasite lifecycles, such as the proteases from species of Plasmodia, Entamoeba, Onchocera, Trypansoma, Leishmania, Haemonchus, Dictyostelium, Therileria, and Schistosoma, such as those associated with malaria (*P. falciparium*), trypanosomes (*T. cruzi,* the enzyme is,also known as cruzain or cruzipain), murine *P. vinckei,* and the *C. elegans* cysteine protease. For an extensive listing of cysteine proteases that may be inhibited by the cysteine protease inhibitors of the present invention, see Rawlings et al., Biochem. J. 290:205–218 (1993), hereby expressly incorporated by reference.

Accordingly, inhibitors of cysteine proteases are useful in a wide variety of applications. For example, the inhibitors of the present invention are used to quantify the amount of cysteine protease present in a sample, and thus are used in assays and diagnostic kits for the quantification of cysteine proteases in blood, lymph, saliva, or other tissue samples, in addition to bacterial, fungal, plant, yeast, viral or mammalian cell cultures. Thus in a preferred embodiment, the sample is assayed using a standard protease substrate. A cysteine protease inhibitor is added, and allowed to bind to any cysteine protease present. The protease assay is then rerun, and the loss of activity is correlated to cysteine protease activity using techniques well known to those skilled in the art.

The cysteine protease inhibitors are also useful to remove or inhibit contaminating cysteine proteases in a sample. For example, the cysteine protease inhibitors of the present invention are added to samples where proteolytic degradation by contaminating cysteine proteases is undesirable. Alternatively, the cysteine protease inhibitors of the present invention may be bound to a chromatographic support, using techniques well known in the art, to form an affinity chromatography column. A sample containing an undesirable cysteine protease is run through the column to remove the protease.

In a preferred embodiment, the cysteine protease inhibitors are useful for inhibiting cysteine proteases implicated in a number of diseases. In particular, cathepsins B, L, and S, cruzain, and interleukin 1β converting enzyme are inhibited. These enzymes are examples of lysosomal cysteine proteases implicated in a wide spectrum of diseases characterized by tissue degradation. Such diseases include, but are not limited to, arthritis, muscular dystrophy, inflammation, tumor invasion, glomerulonephritis, parasite-borne infections, Alzheimer's disease, periodontal disease, and cancer metastasis. For example, mammalian lysosomal thiol proteases play an important role in intracellular degradation of proteins and possibly in the activation of some peptide hormones. Enzymes similar to cathepsins B and L are released from tumors and may be involved in tumor metastasis. Cathepsin L is present in diseased human synovial fluid and transformed tissues. Similarly, the release of cathepsin B and other lysosomal proteases from polymorphonuclear granulocytes and macrophages is observed in trauma and inflammation.

The cysteine protease inhibitors also find application in a multitude of other diseases, including, but not limited to, gingivitis, malaria, leishmaniasis, filariasis, and other bacterial and parasite-borne infections. The compounds also offer application in viral diseases, based on the approach of inhibiting proteases necessary for viral replication. For example, many picornoviruses including poliovirus, foot and mouth disease virus, and rhinovirus encode for cysteine proteases that are essential for cleavage of viral polyproteins.

Additionally, these compounds offer application in disorders involving interleukin-1β converting enzyme (ICE), a cysteine protease responsible for processing interleukin 1β; for example, in the treatment of inflammation and immune based disorders of the lung, airways, central nervous system and surrounding membranes, eyes, ears, joints, bones, connective tissues, cardiovascular system including the pericardium, gastrointestinal and urogenital systems, the skin and the mucosal membranes. These conditions include infectious diseases where active infection exists at any body site, such as meningitis and salpingitis; complications of infections including septic shock, disseminated intravascular coagulation, and/or adult respiratory distress syndrome; acute or chronic inflammation due to antigen, antibody and/or complement deposition; inflammatory conditions including arthritis, chalangitis, colitis, encephalitis, endocarditis, glomerulonephritis, hepatitis, myocarditis, pancreatitis, pericarditis, reperfusion injury and vasculitis. Immune-based diseases include but are not limited to conditions involving T-cells and/or macrophages such as acute and delayed hypersensitivity, graft rejection, and graft-versus-host disease; auto-immune diseases including Type I diabetes mellitus and multiple sclerosis. Bone and cartilage reabsorption as well as diseases resulting in excessive deposition of extracellular matrix such as interstitial pulmonary fibrosis, cirrhosis, systemic sclerosis, and keloid formation may also be treated with the inhibitors of the present invention. The inhibitors may also be useful in the treatment of certain tumor that produce IL 1 as an autocrine growth factor and in preventing the cachexia associated with certain tumors. Apoptosis and cell death are also associated with ICE and may be treated with the inhibitors of the present invention.

Furthermore, the cysteine protease inhibitors of the present invention find use in drug potentiation applications. For example, therapeutic agents such as antibiotics or anti-tumor drugs can be inactivated through proteolysis by endogeneous cysteine proteases, thus rendering the administered drug less effective or inactive. For example, it has been shown that bleomycin, an antitumor drug, can be hydrolyzed by bleomycin hydrolase, a cysteine protease (see Sebti et al., Cancer Res. January 1991, pages 227–232). Accordingly, the cysteine protease inhibitors of the invention may be administered to a patient in conjunction with a therapeutic agent in order to potentiate or increase the activity of the drug. This co-administration may be by simultaneous administration, such as a mixture of the cysteine protease inhibitor and the drug, or by separate simultaneous or sequential administration.

In addition, cysteine protease inhibitors have been shown to inhibit the growth of bacteria, particularly human pathogenic bacteria (see Bjorck et al., Nature 337:385 (1989)). Accordingly, the cysteine protease inhibitors of the present invention may be used as antibacterial agents to retard or inhibit the growth of certain bacteria.

The cysteine protease inhibitors of the invention also find use as agents to reduce the damage of bacterial cysteine proteases to host organisms. For example, staphylococcus produces a very active extracellular cysteine protease which degrades insoluble elastin, possibly contributing to the connective tissue destruction seen in bacterial infections such as septicemia, septic arthritis and otitis. See Potempa et al., J. Biol. Chem. 263(6):2664–2667 (1988). Accordingly, the cysteine protease inhibitors of the invention may be used to treat bacterial infections to prevent tissue damage.

The present invention generally provides new peptide-based and peptidomimetic cysteine protease inhibitors for use as irreversible, mechanism-based cysteine protease inhibitors. In the preferred embodiment, these cysteine protease inhibitors are Michael acceptors. By the term "Michael acceptor" or grammatical equivalents herein is meant an alkene conjugated with an electron-withdrawing group, such as an α,β-unsaturated, vinylogous electron withdrawing group.

The cysteine protease inhibitors are comprised of a targeting group linked to an alkene conjugated with an EWG. A preferred embodiment exhibits the structure shown below in Formula 1:

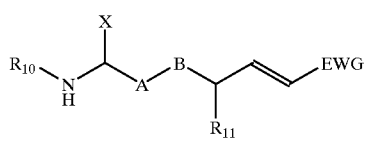

Formula 1 wherein
  $R_{10}$ is hydrogen, a peptide amino end blocking group, a peptide residue with or without an amino end blocking group, a single amino acid residue with or without an amino end blocking group or a label;
  X and $R_{11}$ are amino acid side chains, with either (R) or (S) stereochemical configuration;
  A—B is a peptide linkage; and
  EWG is an electron withdrawing group.

By the term "targeting group", or grammatical equivalents, herein is meant a portion of a cysteine protease inhibitor that allows the binding of the inhibitor to a cysteine protease. In a preferred embodiment, the targeting group of a cysteine protease inhibitor comprises at least one amino acid side chain. In the preferred embodiment, the targeting group comprises at least two amino acids linked via a peptide bond. In a preferred embodiment, the carbon to which the $R_{11}$ amino acid side chain is attached is directly attached to the carbon-carbon double bond. The targeting group may include up to about 15 amino acids, although cysteine protease inhibitors are generally from 1 to 7 amino acids, since smaller inhibitors are usually desired in therapeutic applications.

The targeting group may comprise naturally occurring amino acids and peptide bonds, or synthetic peptidomimetic structures. Thus "amino acid", or "peptide residue", as used herein means both naturally occurring and synthetic amino acids, although preferably a single cysteine protease inhibitor does not contain more than one non-naturally occurring amino acid side chain. For example, homo-phenylalanine, citrulline and noreleucine are considered amino acids for the purposes of the invention. "Amino acid" also includes imino acid residues such as proline and hydroxyproline. The term as used herein also refers to portions of an amino acid, such as an amino acid side chain. The side chains may be in either the (R) or the (S) configuration. In the preferred embodiment, the amino acids are in the (S) or L-configuration.

If non-naturally occurring side chains are used, non-amino acid substituents may be used, for example to prevent or retard in vivo degradations. Such non-amino acid substituents will normally include, but are not limited to, an alkyl, a cycloalkyl, a cycloalkylalkyl, a cycloalkylalkenyl, an aryl, an aralkyl, an alkoxy, a heteroaryl, a heteroarylalkyl, or a heteroarylalkenyl. In such an instance, alkyl is preferably of 1 to 5 carbon atoms, preferably branched, particularly isobutyl. Cycloalkyl preferably is of 3 to 7 carbon atoms, preferably cyclopentyl or cyclohexyl. Cycloalkylalkyl or cycloalkylalkenyl preferably is of 3 to 7 carbon atoms in the cycloalkyl, particularly 5 or 6 carbon atoms, and of 1 to 5 carbon atoms, particularly 1 carbon atom, in the alkyl or alkylene moieties thereof. Aryl preferably is phenyl. Aralkyl preferably is phenylalkyl of 7 to 12 carbon atoms, particularly benzyl and phenylethyl. Alkoxy preferably is of 1 to 5 carbon atoms, preferably methoxy. Acyloxy preferably is of 2 to 6 carbon atoms, preferably acetoxy. Heteroaryl preferably is pyridinyl, especially 4-pyridinyl, thienyl, especially 2-thienyl, or furyl, especially 2-furyl. Heteroarylalkyl and heteroalkenyl preferably has 1 to 6 carbon atoms, especially 1 carbon atom in the alkyl or alkylene moieties thereof. The heteroaryl moiety of heteroarylalkyl and heteroarylakylene preferably has the significances indicated above as preferred for heteroaryl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, halogen-substituted alkyl of 1 to 5 carbon atoms, particularly trifluoromethyl.

The specific amino acids comprising the targeting group are initially determined by the rules governing substrate specificity in cysteine proteases. That is, combinations of amino acids that confer specificity to the enzyme to be inhibited will be used.

It is to be understood that the order of the amino acid side chains within the inhibitor is significant in conferring inhibitor targeting. Thus, as is well known for substrates, the amino acid side chain of the targeting group closest to the alkene bond, generally referred to herein as $R_{11}$, will occupy the $S_1$ position of the enzyme's substrate binding site when the inhibitor is bound to the enzyme. That is, the $R_{11}$ amino acid side chain of the targeting group is the $P_1$ residue of the inhibitor. Similarly, the amino acid side chain of the targeting group second from the alkene bond, generally referred to herein as "X", will occupy the $S_2$ position of the enzyme's substrate binding site when the inhibitor is bound to the enzyme, and thus is the $P_2$ residue. If present, additional amino acid side chains of the inhibitor will occupy the $P_3$, $P_4$, etc. positions.

In a preferred embodiment, additional targeting residues or specificity-enhancing residues are attached to the EWG, to occupy the $S_1'$, $S_2'$, etc. position of the enzyme's substrate binding site. These additional targeting groups are considered the $P_1'$, $P_2'$ etc. residues of the inhibitor. As for the targeting group, the additional targeting, residues are chosen to confer increased specificity on the inhibitor for the particular cysteine protease to be inhibited.

The choice of the amino acid side chains of the targeting group and of the additional targeting residues will be done using the available information about the substrate specificity of the protease, and is routine to those skilled in the art using commercially available substrates. For example, interleukin-1β converting enzyme displays the greatest specificity demonstrated for a cysteine protease toward a substrate, requiring an aspartyl side chain in the $P_1$ position. The papain superfamily of cysteine proteases have an extended specificity site containing five to seven significant subsites, with the dominant one being $S_2$, which is a hydrophobic pocket that binds phenylalanyl-like sidechains very well. Cathepsin B, similar to papain, accepts a phenylalanine side chain in $S_2$, as well as an arginyl sidechain.

For a general review, see "Proteinase Inhibitors", in Research Monographs in Cell and Tissue Physiology (1986), ed. Barrett et al., Vol. 12, Chapter 4: Inhibitors of Cysteine Proteinases, Daniel Rich, Elsevier, New York, hereby expressly incorporated by reference. In addition, the specificity of the interleukin 1β converting enzyme (ICE), was explored in Thornberry et al., supra, also expressly incorporated by reference herein. Table 1 lists some of the favored amino acid side chains for the "X" ($P_2$), $R_{11}$ ($P_1$), etc. positions for a number of cysteine proteases.

TABLE 1

| enzyme | X ($P_2$) | $R_{11}$ ($P_1$) |
|---|---|---|
| papain | phe, try, 2-napthyl, leu, nle, ile, ala | arg, lys, lys (ε-Z), guanidino-phenylalanine, hph, nle |
| cathepsin B | phe, tyr, tyr ($I_2$), 2-napthyl, arg, guanidino-phenylalanine, Cit* | arg, lys, lys (ε-Z), guanidino-phenylalanaine, hph, cit, nle |
| cathepsin L or cruzain | phe, tyr, 2-napthyl | arg, lys, lys (ε-Z), guanidino-phenylalanaine, hph, cit, nle |
| cathepsin S | phe, tyr, 2-napthyl, val, leu, nle, ile, ala | arg, lys, lys (ε-Z), guanidino-phenylalanaine, hph, cit, nle |
| DPP-1 | gly, ala | phe, tyr |
| calpain | val, leu, nle, ile, phe | tyr, phe, met, met ($O_2$), val |
| ICE | ala, val | asp |

*citrulline

The targeting group of the cysteine protease inhibitor may also contain additional functional groups, as shown in Formula 1, above. Thus, the $R_{10}$ group of Formula 1 may be a hydrogen, a peptide amino end blocking group, a peptide residue with or without an amino end blocking group, a single amino acid residue with or without an amino end blocking group, or a label. In some embodiments, the $R_{10}$ group may also be a label, such as a fluorescent label. By the term "peptide amino end blocking group" herein is meant, for example, groups including, but not limited to, an alkoxy-ω-oxoalkanoyl of 2 to 10 carbon atoms, alkoxycarbonyl of overall 2 to 10 carbon atoms, alkanoyl of overall 2 to 10 carbon atoms, cycloalkylcarbonyl of overall 4 to 8 carbon atoms, carbamoyl, alkylcarbamoyl, or dialkylcarbamoyl, a benzoyl, an alkylsulfonyl of overall 1 to 10 carbon atoms, especially alkoxycarbonyl of overall 4 to 8 carbon atoms, particularly tert-butoxycarbonyl (BOC) or benzyloxycarbonyl (CBZ, Z), especially cycloalkylaminocarbonyl or oxacycloalkylaminocarbonyl of overall 4 to 8 atoms in the ring, particularly 4-morpholinecarbonyl (Mu).

The amino acids, or peptide residues, are normally linked via a peptide bond or linkage, i.e. a peptidic carbamoyl group, i.e. —CONH—. Thus, in Formula 1, A=CO and B=NH. However, peptidomimetic bonds are also included, such as $CH_2$—NH, CO—$CH_2$, azapeptide and retro-inverso bonds.

By the term "alkene bond", or grammatical equivalents, herein is meant a carbon-carbon double bond. It is to be understood that the alkene bonds of the cysteine protease inhibitors confer Michael acceptor functionality to the cysteine protease inhibitors. In a preferred embodiment, the carbon to which the $R_{11}$ amino acid side chain is attached is directly attached to the carbon-carbon double bond.

In a preferred embodiment, the targeting group is linked to one of the carbons of the carbon-carbon double bond, and the EWG is linked to the other carbon of the carbon-carbon double bond. By the term "linked" or grammatical equivalents herein is meant a covalent attachment. For the targeting group linkage to the alkene bond, the linkage may be direct, such that the carbon to which the $R_{11}$ amino acid side chain is attached is attached to one of the carbons of the carbon-carbon double bond. Alternatively, there may be other groups between the targeting group and the alkene bond that do not substantially diminish the ability of the targeting group to target an enzyme. In the case of the linkage between the alkene bond and the EWG, the linkage is such that the electron withdrawing properties of the EWG are exerted on the alkene bond, to allow nucleophilic attack by a cysteine protease on the alkene bond.

In a preferred embodiment, the targeting group and the EWG are attached by the alkene bond in trans configuration. In alternative embodiments, the targeting group and the EWG are attached in cis configuration. (α,β-unsaturated compounds in the cis (Z) configuration, as opposed to the trans (E) configuration, are made by using phosphonates bearing the highly electrophilic β-trifluoroethoxy groups at the phsophorus atom (Still et al., Tetrahedron Lett. 24:4405 (1983)) in place of phosphonates bearing dialkyl groups such as diethyl.

By the term "electron withdrawing group" or "EWG" or grammatical equivalents herein is meant a functional group that allows nucleophilic attack by the thiol-group of a cysteine protease at the alkene bond of the inhibitor as a result of the electron withdrawing properties of the EWG. Thus the EWG is conjugated with the alkene bond, such that the electron withdrawing properties of the EWG serve to allow nucleophilic attack by a cysteine protease at the alkene bond, i.e. the alkene bond and the EWG are electronically conjugated. Thus, preferably the linkage between the alkene bond and the EWG is a direct one, without intervening moieties that would prevent the electron withdrawing properties of the EWG from being exerted on the alkene bond.

In some embodiments, an EWG comprises an electron withdrawing moiety, EWM, as defined below. In alternative embodiments, an EWG comprises a ring (e.g. a five or six membered aromatic ring) that is substituted with at least one EWM, a meta directing moiety or group (MDG), or a deactivating group (DG), as defined below. It is to be understood, as will be described more fully below, that an EWG that contains structures such as five or six membered rings between a functional EWM, MDG or DG, and the alkene bond, is permissible as long as the ability of the EWM, MDG or DG to exert an electron withdrawing force on the double bond is not substantially diminished; i.e. that nucleophilic attack by the cysteine protease at the alkene bond may still occur.

In one embodiment, the EWG comprises a homocyclic six membered aromatic ring or a heterocyclic five or six membered aromatic ring, which is substituted with an EWM, MDG or DG. The ring must be aromatic, that is, it must conform to Huckel's rule for the number of delocalized $\pi$ electrons.

If the ring is a six membered homocyclic ring, i.e. containing only carbon, it is substituted, with a substitution group, in such a manner that the substituted ring, when linked to the alkene bond of a cysteine protease inhibitor, allows nucleophilic attack by the protease at the alkene bond. Thus the substituted homocyclic ring is an EWG. The substitution group may be an EWM, MDG, or DG.

In one embodiment, a homocyclic ring may have at least one EWM, as defined below as useful in the Wadsworth-Emmons reaction, substituted at any of the carbons of the ring, to confer electron withdrawing properties on the EWG. Alternative embodiments have more than one EWM substituted on the ring, with up to five substitution groups on a six membered aromatic ring.

In alternative embodiments, the substitution group may or may not be an EWM, as defined below, but instead is considered meta directing in respect to electrophilic aromatic substitution. That is, that the electron withdrawing properties of the substitution group, when present on an aromatic ring, direct further addition of groups to the ring to a meta position, relative to the original substitution group. Meta directing groups or moieties, in respect to electrophilic aromatic substitution, are well known in the art. Examples of meta directing moieties are the quaternary ammonium salts, $NR_3+$, where R may be for example an aryl, alkyl or an aralkyl group, among others, as well as such meta directing groups as $NO_2$, $SO_3H$, $SO_2R$, SOR, $SO_2NH_2$, $SO_2NHR$, $SO_2NHR_2$, $SONH_2$, SONHR, $SONR_2$, CN, $PO_3H$, $P(O)(OR)_2$, P(O)OR, COOH, COR, and COOR'.

In one embodiment, the substitution group is a deactivating group. "Deactivating group" (DG) or grammatical equivalents, means a group or moiety which is deactivating in respect to electrophilic aromatic substitution, by virtue of their electronegativity, as is well known in the art. That is, a substitution group that is deactivating renders the substituted aromatic ring to be less reactive than the non-substituted ring. In this embodiment, examples of suitable deactivating groups are all halogen atoms, such as F, Cl, Br, I, and At; for example, $F_5$, $CF_3$, and $(CF_3)_n$.

The substitution may be either in the para, ortho or meta position, relative to the ring carbon that is attached to one of the carbons of the carbon-carbon double bond of the cysteine protease inhibitor.

Alternatively, the ring may be heterocyclic aromatic rings, that is, contain more than one kind of atom. Thus five membered rings that contain at least one nitrogen, oxygen, phosphorus, arsenic or sulfur atom, and six membered rings that contain at least one nitrogen or phosphorus atom, may be used as outlined below. The rings may contain more than one of the atoms, as well as combinations of atoms. In addition, in the preferred embodiment, the heterocyclic five membered rings may be substituted, as outlined above, with a group that is an EWM as defined below. The six membered rings may be substituted with a group that is either an EWM as defined below, a MDG or a DG, as defined above.

Examples of suitable heterocyclic aromatic rings are pyrrole, furan, thiophene, pyridine, thiazole, pyrimidine, phosphole, and arsole. Particularly useful substitution groups for these rings are quaternary pyridinium salts, such as $NR_3+$, where R is, for example, an aralkyl or alkyl group.

EWGs containing five or six membered aromatic substituted rings useful in the present invention are determined by their ability to be used in the Wittig reaction. The Wittig reaction is a well known method of synthesizing alkenes from carbonyl compounds, wherein the carbonyl oxygen is replaced by a carbon atom, in a reaction with a phosphonium ylide or phosphine oxide. The reaction proceeds if the phosphonium ylide or phosphine oxide contains an electron withdrawing group. Thus an electron withdrawing group that will function in the Wittig reaction can be an EWG in the present invention. This reaction is well characterized and one skilled in the art will be able to choose and assay likely EWG candidates, using routine techniques.

In a preferred embodiment, the EWG comprises an EWM. In this embodiment, the EWM group is attached to or conjugated directly with one of the carbons of the carbon-carbon double bond. By the term "electron withdrawing moiety" or "EWM" or grammatical equivalents herein is meant any functional group that can be used in the Wadsworth-Emmons modification of the Wittig reaction in olefin synthesis. Thus, the ability of a functional group to form $\alpha,\beta$ unsaturated hydrocarbons in the Wadsworth-Emmons reaction will confer the required level of electron withdrawing to function as an EWG in a cysteine protease inhibitor.

One skilled in the art will be able to routinely test the electron-withdrawing properties of a functional group using the Wadsworth-Emmons modification of the Wittig reaction (see Wadsworth et al., J. Am. Chem. Soc. 83:1733, (1961)). For example, the alkali metal anion of $(RO)_2P(O)CH_2$—EWG will react with an aldehyde to form the $\alpha,\beta$ unsaturated alkene.

Preferably, the EWGs of the present invention are vinylogous moieties, that is, they are attached to the carbon-carbon double bond of the cysteine protease inhibitor. As used herein, the term "vinylogous EWG" means an EWG linked to the alkene bond of the inhibitor; that is, the alkene bond is not part of the EWG. Some of the vinylogous compounds that are useful in the present invention include, but are not limited to, vinylogous esters, vinylogous sulfones, vinylogous carboxylates, vinylogous amides, vinylogous phosphonates, vinylogous ketones, vinylogous nitriles, vinylogous sulfoxides, vinylogous sulfonamides, vinylogous sulfinamides, vinylogous nitro compounds, vinylogous sulfonates and vinylogous sulfoximines.

In a preferred embodiment, the cysteine protease inhibitor includes a vinylogous ester moiety as the EWG, as shown in Formula 2:

Formula 2

$$R_{10}-\underset{H}{N}-\underset{X}{\overset{|}{C}}-A-B-\underset{R_{11}}{\overset{|}{C}}-CH=CH-\underset{}{\overset{O}{\overset{\|}{C}}}-OR_1$$

wherein
$R_{10}$ is hydrogen, a peptide amino end blocking group, a peptide residue with or without an amino end blocking group, a single amino acid residue with or without an amino end blocking group or a label;

X and $R_{11}$ are amino acid side chains, with either (R) or (S) stereochemical configuration;

$R_1$ is an ester moiety; and the A—B linkage is a peptide residue or an isosteric form thereof.

By the term "ester moiety" herein is meant a group including, but not limited to, an alkyl, a cycloalkyl, a cycloalkylalkyl, an aryl, or an aralkyl. In such an instance, alkyl is preferably of 1 to 5 carbon atoms, especially ethyl. Cycloalkyl preferably is of 3 to 7 carbon atoms, preferably cyclopentyl or cyclohexyl. Cycloalkylalkyl preferably is of 3 to 7 carbon atoms in the cycloalkyl, particularly 5 or 6 carbon atoms, and of 1 to 5 carbon atoms, particularly 1 carbon atom, in the alkyl moieties thereof. Aryl preferably is phenyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Particularly preferred $R_1$ groups include C1–C5 alkyl, especially ethyl; C3–C7 cycloalkyl, especially cyclopentyl or cyclohexyl; C3–C7 (cycloalkyl)-C1–C5 alkyl, especially C5–C6(cycloalkyl)-methyl; phenyl; C7–C12 phenylalkyl, especially benzyl; aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred. Also preferred are aryl or aralkyl substituted by one or two groups of halogen-substituted C1–C5 alkyl, especially trifluoromethyl; nitro; sulfonyl; or arylsulfonyl, in protected form where appropriate.

In a specific preferred embodiment, cysteine protease inhibitors containing vinylogous esters as EWGs are (1) ethyl (S)-(E)-4-(4-morpholinecarbonylphenylalanyl)-amino-6-phenyl-2-hexenoate, abbreviated herein as Mu-Phe-HphVEOEt, (2) ethyl (S)-(E)-7-guanidino-4-(4-morpholinecarbonylphenylalanyl)amino-2-heptenoate hydrobromide, abbreviated herein as Mu-Phe-ArgVEOEt.HBr; (3) (S)-(E)-Ethyl 8-(benzyloxycarbonyl)amino-4-(4-morpholinecarbonylphenylalanyl)amino-2-octenoate, abbreviated herein as Mu-Phe-Lys(z)VEOEt; and (4) (S)-(E)-Ethyl 8-amino-4-(4-morpholinecarbonylphenylalanyl)amino-2octenoate hydrobromide, abbreviated herein as Mu-Phe-LysVEOEt-HBr.

In an additional preferred embodiment, the cysteine protease inhibitor includes a vinylogous sulfone moiety as the EWG, as shown in Formula 3:

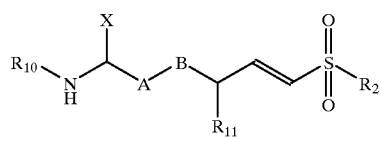

Formula 3 wherein $R_{10}$ is hydrogen, a peptide amino end blocking group, a peptide residue with or without an amino end blocking group, a single amino acid with or without an amino end blocking group, or a label;

X an $R_{11}$ are amino acid side chains, with either (R) or (S) stereochemical configuration;

$R_2$ is a side chain moiety; and the A—B linkage is a peptide residue or an isosteric form thereof.

The S—$R_2$ bond is a sulfur-carbon link where $R_2$ is a side chain moiety. The $R_2$ side chain moiety may be a group including, but not limited to, an alkyl, a substituted alkyl, a cycloalkyl, a cycloalkylalkyl, a cycloalkylalkenyl, an aryl, or an aralkyl. In such an instance, alkyl is preferably of 1 to 5 carbon atoms, especially methyl. Substituted alkyl is preferably of 1 to 5 carbon atoms, bearing substitutions of alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Cycloalkyl preferably is of 3 to 7 carbon atoms, preferably cyclopentyl or cyclohexyl. Cycloalkylalkyl or cycloalkylalkenyl preferably is of 3 to 7 carbon atoms in the cycloalkyl, particularly 5 or 6 carbon atoms, and of 1 to 5 carbon atoms, particularly I carbon atom, in the alkyl or alkylene moieties thereof. Aryl preferably is phenyl, pentafluorophenyl or naphthyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl.

Particularly preferred $R_2$ groups include (1) C1–C5 alkyl, especially methyl; (2) C3–C7 cycloalkyl, preferably cyclopentyl or cycolhexyl; (3) C3–C7(cycloalkyl)-C1–C5 alkyl, preferably C5–C6(cycloalkyl)methyl; (4) C3–C7 (cycloalkylalkenyl)-C1–C5 alkyl, preferably C5–C6 (cycloalkylalkenyl)methyl; (5) phenyl, preferably pentafluorophenyl or naphtyl; (6) C7–C12 phenylalkyl, preferably benzyl; (7) C1–C5 alkyl substituted by C1–C5 alkyoxy, halogen, hydroxy or amino, with C1–C5 alkyl preferably substituted by one or two groups selected from methyl, methoxy, chlorine, bromine, fluorine, hydroxy or amino, with hydroxy, amino, chlorine, bromine or fluorine being most preferred; (8) C1–C5 alkyl substituted with nitro, alkyl or arylsufonyl, optionally protected where appropriate; (9) C1–C5 alkyl substituted with halogen, preferably trifluoromethyl; (10) aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred; (11) aryl or aralkyl substituted by one or two groups of halogen-substituted C1–C5 alkyl, especially trifluoromethyl; nitro; sulfonyl; or arylsulfonyl, in protected form where appropriate.

Preferred cysteine protease inhibitors with vinylogous sulfones as the EWG include: (1) (S)-(E)-5-(4-morpholinecarbonylphenylalanyl)amino-7-phenyl-2-thia-3-heptene 2,2-dioxide, abbreviated herein as Mu-Phe-HphVSMe; (2) (S)(E)-3-tert-butoxycarbonylamino-4- methyl-1-phenylsulfonyl-1-pentene, abbreviated herein as Boc-ValVSPh; (3) (S)-(E)-3-(4-morpholinecarbonyl-phenylalanyl)amino-5-phenyl-1-phenylsulfonyl-1-pentene, abbreviated herein as Mu-Phe-HphVSPh; (4) (S)-(E)- 3-tert-butoxycarbonylamino-4-tert-butoxycarbonyl-1-methylsulfonyl-1-butene, abbreviated herein as (Boc-Asp(Ot-Bu)VSMe; (5) (S)-(E)-3-amino-4-tert-butoxycarbonyl-1-methylsulfonyl-1-butene, abbreviated TsOH.Asp(Ot-Bu)VSMe; (6) (S)-(E)-3-tert-butoxycarbonylamino-4-tert-butoxycarbonyl-1-phenylsulfonyl-1-butene, abbreviated Boc-Asp(Ot-Bu)-VSPh; (7) (S)-(E)-3-amino-4-tert-butoxycarbonyl-1-phenylsulfonyl-1-butene-p-toluenesulfonate, abbreviated TsOH.Asp(Ot-Bu)VSPh; (8) (S)-(E)-3-amino-4-hycroxylcarbonyl-1-phenylsulfonyl-1-butene-p-toluenesulfonate, abbreviated HCl.AspVSPh; (9) (E)-3-acetyltyrosylvalylalanylamino-4-tert-butoxycarbonyl-1-phenylsulfonyl-1-butene, abbreviated Ac-Tyr-Val-Ala-Asp(Ot-Bu)VSPh; (10) (e)-3-acetyltyrosylvalylalanylamino-4-hydroxycarbonyl-1-phenylsulfonyl-1-butene (Ac-Tyr-Val-Ala-AspVSPh; (11) (S)-(E)-3-(4-morpholinecarbonylleucyl)amino-5-phenyl-1-phenylsulfonyl-1-pentene, abbreviated Mu-Leu-HphVSPh, (12) (S)-(E)-3-(4-morpholinecarbonylphenylalanyl)amino-6-guanidino-1-phenylsulfonyl-1-hexene hydrobromide, abbreviated Mu-Phe-ArgVSPh.HBr; (13) (S)-(E)-3-(4-morpholinecarbonylphenylalanyl)amino-5-phenyl-1-phenylsulfonyl-1-pentene, abbreviated Mu-Phe-HphVSPh; (14) (S)-(E)-3-glycylamino-4-phenyl-1-phenylsulfonyl-1-butene hydrochloride, abbreviated Gly-PheVSPh.HCl; (15) (S)-(E)-7-(benzyloxycarbonyl)amino-3-(4-morpholinecarbonylphenylalanyl)-amino-1-phenylsulfonyl-1-heptene, abbreviated Mu-Phe-Lys(Z)VSPh: (16) (G)-(E)-7-amino-3-(4-morpholinecarbonylphenylalanyl)amino-1-phenylsulfonyl-1-heptene hydrobromide, abbreviated Mu-Phe-LysVSPh.HBr; (17) (S)-(E)-3-(4-morpholinecarbonylphenylalanyl)amino-4-methyl-1-phenylsulfonyl-1-pentene, abbreviated Mu-Phe-ValVSPh; (18) (S)-(E)-3-amino-4-phenyl-1-phenylsulfonyl-1-butene hydrochloride, abbreviated PheVSPh.HCl; (19) (S)-(E)-3-(4-morpholinecarbonylvalyl)amino-4-phenyl-1-phenylsulfonyl-1-butene, abbreviated Mu-Val-PheVSPh; (20) (S)-(E)-3-(4-morpholinecarbonylarginyl)amino-6-guanidino-1-phenylsulfonyl-1-hexene dihydrobromide, abbreviated Mu-ARg-Arg-VSPh.2HBr; (21) (S)-(E)-3-(4-morpholinecarbonylphenylalanyl)amino-4-benzyloxy-1-phenylsulfonyl-1-butene, abbreviated Mu-Phe-SEr(OBzl)VSPh; (22) (S)-(E)-3-(4-morpholinecarbonylphenylalanyl)amino-7-benzoylamino-1-phenylsulfonyl-1-heptene, abbreviated Mu-Phe-Lys(Bz)VSPh; (23) (R)-(E)-3-(4-morpholinecarbonylphenylalanyl)amino-5-phenyl-1-phenylsulfonyl-1-pentene, abbreviated Mu-Phe-D-HphVSPh; (24) (S)-(E)-3-[4-morpholinecarbonyl-(3,5-diiodotyrosyl)]-amino-5-phenyl-1-phenylsulfonyl-1-pentene, abbreviated Mu-Tyr(I$_2$)-HphVSPh; (25) (S)-(E)-3-[4-tert-butoxycarbonyl-(3,5-diiodotyrosyl)]-amino-5-phenyl-1-phenylsulfonyl-1-pentene, abbreviated Boc-Tyr(I$_2$)-HphVSPh; (26) (S,S)-(E)-3-[4-morpholinecarbonyl-(1,2,3,4-tetrahydro-3-isoquinoline-carbonyl)]amino-5-phenyl-1-phenylsulfonyl-1-pentene, abbreviated Mu-Tic-HphVSPh; (27) (S,S)-(E)-3-[tert-butoxycarbonyl-(1,2,3,4-tetrahydro-3-isoquinolinecarbonyl)]-amino-5-phenyl-1-phenylsulfonyl-1-pentene, abbreviated Boc-Tic-HphVSPh; (28) (S)-(E)-3-(4-morpholinecarbonylleucylleucyl)amino-4-(4-hydroxyphenyl)-1-phenylsulfonyl-1-butene, abbreviated Mu-Leu-HphVSPh; (29) (S)-(E)-3-amino-5-phenyl-1-phenylsulfonyl-1-pentene hydrochloride, abbreviated HphVSPh-HCl; (30) (S)-(E)-3-[(4-morpholinecarbonyl-(R,S)-α-methylphenylalanyl]amino-5-phenyl-1-phenylsulfonyl-1-pentene, abbreviated Mu-DL-Fam-HphVSPh; (31) (S)-(E)-3-(benzyloxycarbonylleucylleucyl)amino-4-(4-hydroxyphenyl)-1-phenylsulfonyl-1-butene, abbreviated Z-Leu-Leu-TyrVSPh; (32) (S)-(E)-3-(4-morpholinecarbonyltyrosyl)amino-5-phenyl-1-phenylsulfonyl-1-pentene, abbreviated Mu-Tyr-HphVSPh; (33) (S)-(E)-3-(tert-butoxycarbonyl-2-naphthylalanyl)amino-5-phenyl-1-phenylsulfonyl-1-pentene, abbreviated Boc-Np-HphVSPh; (34) (S)-(E)-3-(4-morpholinecarbonyl-2-naphthylalanyl)amino-5-phenyl-1-phenylsulfonyl-1-pentene, abbreviated Mu-Np-HphVSPh; (35) (S)-(E)-3-(4-morpholinecarbonyl-4-biphenylalanyl)amino-5-phenyl-1-phenylsulfonyl-1-pentene, abbreviated Mu-Bip-HphVSPh; (36) (S)-(E)-3-(4-morpholinecarbonylphenylalanyl)amino-1-phenylsulfonyl-1-heptene, abbreviated Mu-Phe-NleVSPh; (37) (S)-(E)-3-(4-morpholinecarbonylphenylalanyl)amino-1-phenylsulfonyl-6-thia-1-heptene, abbreviated Mu-Phe-MetVSPh; (38) (S)-(E)-3-(4-morpholinecarbonylphenylalanyl)amino-5-methylsulfonyl-1-phenylsulfonyl-1-pentene, abbreviated Mu-Phe-Met(O$_2$)VSPh; (39) (S)-(E)-3-(acetylleucylleucyl)amino-1-phenylsulfonyl-1-heptene, abbreviated Ac-Leu-Leu-NleVSPh; (40) (S)-(E)-3-(acetylleucylleucyl)amino-1-phenylsulfonyl-6-thia-1-heptene, abbreviated Ac-Leu-Leu-MetVSPh; (41) (S)-(E)-3-(acetylleucylleucyl)amino-5-methylsulfonyl-1-phenylsulfonyl-1-pentene, abbreviated Ac-Leu-Leu-Met(O$_2$)VSPh; (42) (S)-(E)-3-(carbomethoxypropionylphenylalanyl)amino-5-phenyl-1-phenylsulfonyl-1-pentene, abbreviated MeOSuc-Phe-HphVSPh; (43) (S)-7-(benzyloxycarbonyl)amino-3-(4-morpholinecarbonylphenylalanyl)amino-1-fluoro-1-phenylsulfonyl-1-heptene, abbreviated Mu-Phe-Lys(Z)fVSPh; (44) (S)-(E)-3-(acetylleucylleucyl)amino-4-(4-hydroxyphenyl)-1-phenylsulfonyl-1-butene, abbreviated Ac-Leu-Leu-TyrVSPh; (45) (S)-(E)-3-(dimethylsulfamoylphenylalanyl)amino-5-phenyl-1-phenylsulfonyl-1-pentene, abbreviated DimSam-Phe-HphVSPh; (46) (S)-(E)-3-(4-morpholinecarbonylphenylalanyl)amino-1-(4-bromophenylsulfonyl)-5-phenyl-1-pentene, abbreviated Mu-Phe-HphVSPhBr; (47) (S)-(E)-3-(4-morpholinecarbonylphenylalanyl)amino-1-(2-napthylsulfonyl)-5-phenyl-1-pentene, abbreviated Mu-Phe-HphVSNp; (48) (S)-(E)-3-(4-morpholinecarbonyl-2-naphthylalanyl)amino-1-(2-napthylsulfonyl)-5-phenyl-1-pentene, abbreviated Mu-Np-HphVSNp; (49) (S)-(E)-3-(4-morpholinecarbonyl)amino-5-phenyl-1-phenylsulfonyl-1-pentene, abbreviated Mu-HphVSPh; (50) (S)-(E)-3-(4-morpholinecarbonylphenylalanyl)amino-1-methylsulfonyl-1-butene, abbreviated Mu-Phe-AlaVSMe; (51) (S)-(E)-3-(4-morpholinecarbonylphenylalanyl)amino-1-methylsulfonyl-4-phenyl-1-butene, abbreviated Mu-Phe-PheVSMe; and (52) (S)-(E)-3-(tert-2butoxycarbonylalanyl)amino-1-methylsulfonyl-4-phenyl-1-butene, abbreviated Boc-Ala-PheVSMe.

In one embodiment, the cysteine protease inhibitors of the present invention include a vinylogous carboxylate as the EWG, as shown in Formula 4:

Formula 4

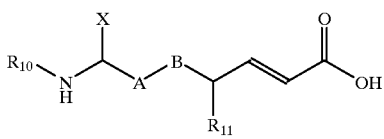

wherein
- $R_{10}$ is hydrogen, a peptide amino end blocking group, a peptide residue with or without an amino end blocking group, a single amino acid with or without an amino end blocking group, or a label;
- X and $R_{11}$ are amino acid side chains, with either (R) or (S) stereochemical configuration; and
- the A—B linkage is a peptide residue or an isosteric form thereof.

In the preferred embodiment, a cysteine protease inhibitor with a vinylogous carboxylate as the EWG is (S)-(E)-4-(4-morpholinecarbonylphenylalanyl)amino-6- phenyl-2-hexenoic acid, abbreviated herein as Mu-Phe-HphVA, and (S)-(E)-Benzyl 4-(4-morpholinecarbonylphenylalanyl) amino-6-phenyl-2-hexenamide, abbreviated herein as Mu-Phe-HphVAMbzl.

In a preferred embodiment, the cysteine protease inhibitor includes a vinylogous phosphonate as the EWG, as shown in Formula 5:

Formula 5

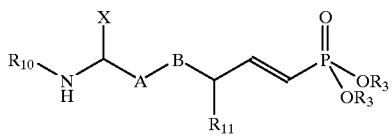

wherein
- $R_{10}$ hydrogen, a peptide amino end blocking group, a peptide residue with or without an amino end blocking group, a single amino acid with or without an amino end blocking group, or a label;
- X and $R_{11}$ are amino acid side chains, with either (R) or (S) stereochemical configuration;
- $R_3$ is an ester moiety; and
- the A—B linkage is a peptide residue or an isosteric form thereof.

The $R_3$ groups are ester moieties, and may be groups including, but not limited to, an alkyl, a cycloalkyl, a cycloalkylalkyl, a cycloalkylalkenyl, an aryl, or an aralkyl. In such an instance, alkyl is preferably of 1 to 5 carbon atoms, especially ethyl. Cycloalkyl preferably is of 3 to 7 carbon atoms, preferably cyclopentyl or cyclohexyl. Cycloalkylalkyl or cycloalkylalkenyl preferably is of 3 to 7 carbon atoms in the cycloalkyl, particularly 5 or 6 carbon atoms, and of 1 to 5 carbon atoms, particularly 1 carbon atom, in the alkyl or alkylene moieties thereof. Aryl preferably is phenyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Also included are perfluoro groups, such as perfluoro alkyl, aryl and aralkyl groups.

Particularly preferred are: (1) C1–C5 alkyl, especially ethyl; (2) C3–C7 cycloalkyl, preferably cyclopentyl or cycolhexyl; (3) C3–C7(cycloalkyl)-C1–C5 alkyl, preferably C5–C6(cycloalkyl)methyl; (4) C3–C7(cycloalkylalkenyl)-C1–C5 alkyl, preferably C5–C6(cycloalkylalkenyl)methyl; (5) phenyl; (6) C7–C12 phenylalkyl, preferably benzyl; (7) C1–C5 alkyl substituted by C1–C5 alkyoxy, halogen, hydroxy or amino, with C1–C5 alkyl preferably substituted by one or two groups selected from methyl, methoxy, chlorine, bromine, fluorine, hydroxy or amino, with hydroxy, amino, chlorine, bromine or fluorine being most preferred; (8) C1–C5 alkyl substituted with nitro, alkyl or arylsufonyl, optionally protected where appropriate; (9) C1–C5 alkyl substituted with halogen, preferably trifluoromethyl; (10) aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred; (11) aryl or aralkyl substituted by one or two groups of halogen-substituted C1–C5 alkyl, especially trifluoromethyl; nitro; sulfonyl; or arylsulfonyl, in protected form where appropriate.

In a preferred embodiment, a cysteine protease inhibitor with a vinylogous phosphonate as the EWG is diethyl (S)-(E)-4-(4-morpholinecarbonylphenylalanyl)amino-6-phenyl-2-hexenephosphonate, abbreviated herein as Mu-Phe-HphVPEt.

In another preferred embodiment, the cysteine protease inhibitors of the present invention include vinylogous amides as the EWG, as shown in Formula 6:

Formula 6

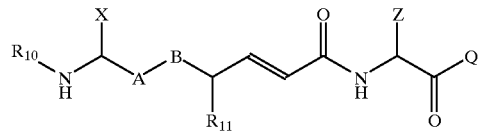

wherein
- $R_{10}$=hydrogen, a peptide amino end blocking group, a peptide residue with or without an amino end blocking group, a single amino acid with or without an amino end blocking group, or a label;
- X, $R_{11}$ and Z are amino acid side chains, with either (R) or (S) stereochemical configuration,
- Q=hydrogen, an ester, a peptide residue, or an amide moiety; and
- The A—B linkage is a peptide residue or an isosteric form thereof.

By "amide moiety" as used with regard to Q is meant a group including, but not limited to, an NH2, or an NH-alkyl, an NH-cycloalkyl, an NH-cycloalkylalkyl, an NH-aryl, or an NH-aralkyl, or an N-dialkyl, N-dicycloalkyl, an N-dicycloalkylalkyl, an N-diaryl, or an N-diaralkyl. In such an instance, alkyl is preferably of 1 to 5 carbon atoms, especially ethyl. Cycloalkyl preferably is of 3 to 7 carbon atoms, preferably cyclopentyl or cyclohexyl. Cycloalkylalkyl preferably is of 3 to 7 carbon atoms in the cycloalkyl, particularly 5 or 6 carbon atoms, and of 1 to 5 carbon atoms, particularly 1 carbon atom, in the alkyl moieties thereof. Aryl preferably is phenyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl.

Particularly preferred for Q are: (1) NH—(C1–C5) alkyl, especially NH-ethyl; (2) NH—(C3–C7)cycloalkyl, preferably cyclopentyl or cyclohexyl; (3) HN—(C3–C7) cycloalkyl-(C1–C5) alkyl, preferably NH—(C5–C6) cycloalkyl-methyl; (4) NH-aryl, preferably NH-phenyl; (5) NH—(C—C12)phenylalkyl, preferably benzyl; (6) aryl or aralkyl substituted by one or two groups of (C1–C5) alkyl, (preferably methyl), (C1–C5)alkyoxy, (preferably methoxy), or halogen, (preferably chlorine,bromine, fluorine, hydroxy, or amino).

Especially preferred is to substitue the aryl or aralkyl with one group selected from hydroxy, amino, chlorine, bromine, or fluorine, optionally in protected form where appropriate, nitro, alkyl or arylsufonyl, or halogen-substituted (C1–C5) alkyl, especially trifluoromethyl.

The ester as used with regard to Q may be an oxygen linked with the ester moieties defined for vinylogous esters and phosphonates to form esters. Specific preferred embodiments, include the following cysteine protease inhibitors that contain vinylogous amides as the EWG: (S)-(E)-(N-leucylproline methylester)-4-(4-morpholinecarbonylphenyl-alanyl)amino-6-phenyl-2-hexenamide, abbreviated herein as Mu-Phe-HphVAM-Leu-ProOMe; (S)-(E)-(N-phenylalanine)-4-(4-morpholinecarbonylphenylalanyl)amino- 6-phenyl-2-hexenamide, abbreviated herein as Mu-Phe-HphVAM-PheOH; (S)-(E)-3-(4-morpholinecarbonyl-phenylalanylamino)-6-phenyl-2-hexenamide, abbreviated Mu-Phe-HphVAM; and (S)-(E)-Benzyl 4-(4-morpholine-carbonyl)amino-6-phenyl-2-hexenamide, abbreviated Mu-Phe-HphVAMBzl.

Although not preferred, in one embodiment, the cysteine protease inhibitor includes a vinylogous ketone as the EWG, as shown in Formula 7:

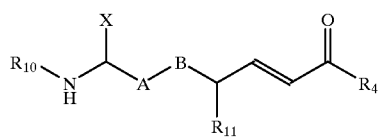

Formula 7 wherein
  $R_{10}$=hydrogen, a peptide amino end blocking group, a peptide residue with or without an amino end blocking group, a single amino acid with or without an amino end blocking group, or a label;
  X and $R_{11}$ are amino acid side chains, with either (R) or (S) stereochemical configuration;
  $R_4$=ketone moiety; and
  the A—B linkage is a peptide residue or an isosteric form thereof.

By "ketone moiety" as used with regard to $R_4$ herein is meant groups including, but not limited to, an alkyl, a cycloalkyl, a cycloalkylalkyl, a cycloalkylalkenyl, an aryl, or an aralkyl. In such an instance, alkyl is preferably of 1 to 5 carbon atoms, especially ethyl. Cycloalkyl preferably is of 3 to 7 carbon atoms, preferably cyclopentyl or cyclohexyl.

Cycloalkylalkyl or cycloalkylalkenyl preferably is of 3 to 7 carbon atoms in the cycloalkyl, particularly 5 or 6 carbon atoms, and of 1 to 5 carbon atoms, particularly 1 carbon atom, in the alkyl or alkylene moieties thereof. Aryl preferably is phenyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Also included are perfluoro groups, such as perfluoro alkyl, aryl, and aralkyl.

Particularly preferred are: (1) (C1–C5)alkyl, preferably ethyl; (2) (C3–C7)cycloalkyl, preferably cyclopentyl or cyclohexyl; (3) (C3–C7)cycloalkyl-(C1–C5)alkyl, especially (C5–C6)cycloalkyl-methyl; (4) (C3–C7)cycloalkyl-(C1–C5)alkenyl, especially (C5–C6)cycloalkyl-methylene; (5) phenyl; (6) (C7–C12)penylalkyl, especially benzyl; (7) aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred; (11) aryl or aralkyl substituted by one or two groups of halogen-substituted C1–C5 alkyl, especially trifluoromethyl; nitro; sulfonyl; or arylsulfonyl, in protected form where appropriate; (12) perfluoro groups, such as perfluoro alkyl, aryl, and aralkyl.

In another preferred embodiment, the cysteine protease inhibitors of the present invention include a nitrile group as the EWG, as shown in Formula 8:

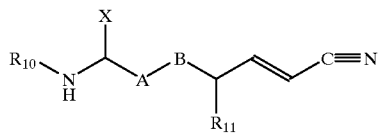

Formula 8 wherein
  $R_{10}$=hydrogen, a peptide amino end blocking group, a peptide residue with or without an amino end blocking group, a single amino acid with or without an amino end blocking group, or a label;
  X and $R_{11}$ amino acid side chains, with either (R) or (S) stereochemical configuration;
  the C≡N group is a nitrile; and
  the A—B linkage is a peptide residue or an isosteric form thereof.

In another preferred embodiment, the cysteine protease inhibitors of the present invention contain a vinylogous sulfoxide as the EWG, as shown in Formula 9:

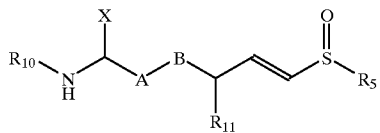

Formula 9

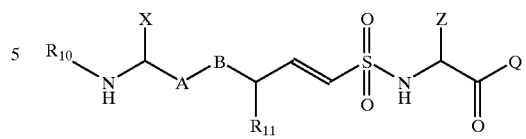

Formula 10 wherein $R_{10}$=hydrogen, a peptide amino end blocking group, a peptide residue with or without an amino end blocking group, a single amino acid with or without an amino end blocking group, or a label;

X and $R_{11}$ are amino acid side chains, with either (R) or (S) stereochemical configuration;

$R_5$=sulfoxide moiety; and the A—B linkage is a peptide residue or an isosteric form thereof.

By "sulfoxide moiety" as used with regard to $R_5$ herein is meant groups including, but are not limited to, an alkyl, a cycloalkyl; a cycloalkylalkyl, a cycloalkylalkenyl, an aryl, or an aralkyl. In such an instance, alkyl is preferably of 1 to 5 carbon atoms, especially ethyl. Cycloalkyl preferably is of 3 to 7 carbon atoms, preferably cyclopentyl or cyclohexyl. Cycloalkylalkyl or cycloalkylalkenyl preferably is of 3 to 7 carbon atoms in the cycloalkyl, particularly 5 or 6 carbon atoms, and of 1 to 5 carbon atoms, particularly 1 carbon atom, in the alkyl or alkylene moieties thereof. Aryl preferably is phenyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Also included are perfluoro groups such as perfluoro alkyl, aryl, and aralkyl.

Particularly preferred for $R_5$ are:(1) (C1–C5)alkyl, preferably ethyl; (2) (C3–C7)cycloalkyl, preferably cyclohexyl or cyclopentyl; (3) (C3–C7)cycloalkyl-(C1–C5)alkyl, preferably (C5–C6)cycloalklyl-C1alkyl-C1alkyl; (4) (C3–C7) cycloalkyl-(C1–C5)alkenyl, preferably (C5–C6)cycloalkyl-C1alkenyl; (5) phenyl; (6) (C7–C12)phenylalkyl, preferably benzyl; (7) aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred; or (8) aryl or aralkyl substituted by one or two groups of halogen-substituted C1–C5 alkyl, especially trifluoromethyl.

In a preferred embodiment, the EWG of the cysteine protease inhibitor includes a vinylogous sulfonamide as the EWG, as shown in Formula 10:

wherein $R_{10}$=hydrogen, a peptide amino end blocking group, a peptide residue with or without an amino end blocking group, a single amino acid with or without an amino end blocking group, or a label;

X, $R_{11}$ and Z are amino acid side chains, with either (R) or (S) stereochemical configuration;

Q=hydrogen, an ester, a peptide residue or an amide moiety; and the A—B linkage is a peptide residue or an isosteric form thereof.

By "amide moiety" as used with regard to Q is meant a group including, but not limited to, an NH2, or an NH-alkyl, an NH-cycloalkyl, an NH-cycloalkylalkyl, an NH-aryl, or an NH-aralkyl, or an N-dialkyl, N-dicycloalkyl, an N-dicycloalkylalkyl, an N-diaryl, or an N-diaralkyl. In such an instance, alkyl is preferably of 1 to 5 carbon atoms, especially ethyl. Cycloalkyl preferably is of 3 to 7 carbon atoms, preferably cyclopentyl or cyclohexyl. Cycloalkylalkyl preferably is of 3 to 7 carbon atoms in the cycloalkyl, particularly 5 or 6 carbon atoms, and of 1 to 5 carbon atoms, particularly 1 carbon atom, in the alkyl moieties thereof. Aryl preferably is phenyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl.

By "ester" as regards to Q means an oxygen attached to the ester moities previously defined, to form an ester.

In a preferred embodiment, the cysteine protease inhibitors of the present invention include a vinylogous sulfoximine as the EWG, as shown in Formula 11:

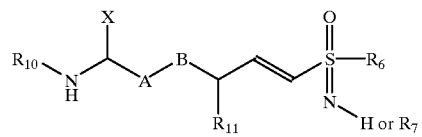

Formula 11 wherein $R_{10}$=hydrogen, a peptide amino end blocking group, a peptide residue with or without an amino end blocking group, a single amino acid with or without an amino end blocking group, or a label;

X and $R_{11}$ are amino acid side chains, with either (R) or (S) stereochemical configuration;

$R_6$ and $R_7$ a re sulfoximine moieties; and the A—B linkage is a peptide residue or an isosteric form thereof.

By "sulfoximine moieties" as used with regard to $R_6$ and $R_7$ is meant identical or different groups including, but not limited to, an alkyl, a cycloalkyl, a cycloalkylalkyl, a cycloalkylalkenyl, an aryl, or an aralkyl. In such an instance, alkyl is preferably of 1 to 5 carbon atoms, especially ethyl. Cycloalkyl preferably is of 3 to 7 carbon atoms, preferably cyclopentyl or cyclohexyl. Cycloalkylalkyl or cycloalkylalkenyl preferably is of 3 to 7 carbon atoms in the cycloalkyl, particularly 5 or 6 carbon atoms, and of 1 to 5 carbon atoms, particularly 1 carbon atom, in the alkyl or alkylene moieties thereof. Aryl preferably is phenyl. Aralkyl preferably is phenylalkyl of 7 to 12 carbon atoms, particularly benzyl. The optional substituents of an aryl or aralkyl moiety preferably are one or two groups alkyl of 1 to 5 carbon atoms, alkoxy of 1 to 5 carbon atoms, halogen of atomic number of from 9 to 35, hydroxy and/or amino, preferably one or two groups methyl, methoxy, chlorine, bromine, fluorine, hydroxy or amino, particularly one hydroxy, amino, chlorine, bromine, or fluorine, optionally in protected form where appropriate, nitro, alkyl or arylsulfonyl, or halogen-substituted alkyl of 1 to 5 carbon atoms, particularly trifluoromethyl. Also included are perfluoro groups, such as perfluoro aryl, alkyl, and aralkyl groups.

Particularly preferred for $R_6$ and $R_7$ are: (1) (C1–C5) alkyl, preferably ethyl; (2) (C3–C7)cycloalkyl, preferably cyclohexyl or cyclopentyl; (3) (C3–C7)cycloalkyl-(C1–C5) alkyl, preferably (C5–C6)cycloalkyl-C1alkyl; (4) (C3–C7) cycloalkyl-(C1–C5)alkenyl, preferably (C5–C6)cycloalkyl-C1alkenyl; (5) phenyl; (6) (C7–C12)phenylalkyl, preferably benzyl; (7) aryl or aralkyl substituted by one or two groups of C1–C5 alkyl, C1–C5 alkoxy, halogen, hydroxy or amino, with one or two groups of methyl, methoxy, chlorine, bromine, fluorine, hydroxy or amino being preferred and hydroxy, amino, chlorine, bromine or fluorine being particularly preferred; or (8) aryl or aralkyl substituted by one or two groups of halogen-substituted C1–C5 alkyl, especially trifluoromethyl.

In one embodiment, the cysteine protease inhibitors of the present invention have the structure shown in Formula 12:

Formula 12

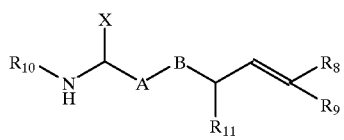

wherein
$R_8$=the five or six membered homo- or heterocyclic aromatic rings with at least one substituted EWM, MDG, or DG; and
$R_9$=a suitable group as defined below.

The $R_8$ group is an EWG group. It may be a five or six membered homocyclic aromatic ring with at least one substitution group. The substituted group may be an EWM, as defined above, in the case of five membered rings, or an EWM, MDG, or DG as defined above. EWMs that may be substituted onto a five or six membered ring that are preferred are esters, sulfones, carboxylates, amides, phosphonates, ketones, nitrites, nitro compounds, sulfonates, sulfoxides, sulfonamides, sulfinamides, and sulfoximines, as are defined above. MDGs that may be used are the quaternary ammonium salts, $NR_3+$, where R may be for example an aryl, alkyl or aralkyl, as well as such meta directing groups as $NO_2$, $SO_3H$, $SO_2R$, $SOR$, $SO_2NH_2$, $SO_2NHR$, $SO_2NHR_2$, $SONH_2$, $SONHR$, $SONR_2$, $CN$, $PO_3H$, $P(O)(OR)_2$, $P(O)OR$, $OH$, $COOH$, $COR$, and $COOR'$. DGs that may be substituted onto a six membered ring are all the halogen atoms, such as F, Cl, Br, I, and At; for example, $F_5$, $CF_3$, and $(CF_3)_n$.

The $R_9$ group may be a wide variety of groups. In the preferred embodiment, the $R_9$ group is a hydrogen atom, or other functionally neutral groups such as methyl groups. In alternative embodiments, the $R_9$ group is a peptide, such that additional targeting or specificity-enhancing residues are added to the cysteine protease inhibitor.

In a preferred embodiment, the cysteine protease inhibitors of the present invention have a vinylogous five membered heterocyclic aromatic ring with a substituted EWM, as the EWG, as shown in Formula 13:

Formula 13

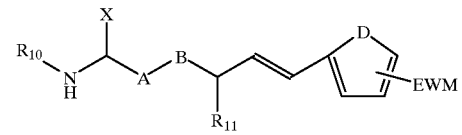

wherein
$R_{10}$=hydrogen, a peptide amino end blocking group, a peptide residue with or without an amino end blocking group, a single amino acid with or without an amino end blocking group, or a label;
X and $R_{11}$ are amino acid side chains, with either (R) or (S) stereochemical configuration;
the A—B linkage is a peptide residue or an isosteric form thereof;
D=an oxygen, sulfur, nitrogen, phosphorus or arsenic atom; and
EWM=an electron withdrawing moiety.

The EWM may be any of the electron withdrawing groups as previously defined.

In a preferred embodiment, the cysteine protease inhibitors of the present invention have a vinylogous six membered homocyclic aromatic ring with a substituted EWM, MDG or DG as the EWG, as shown in Formula 14:

Formula 14

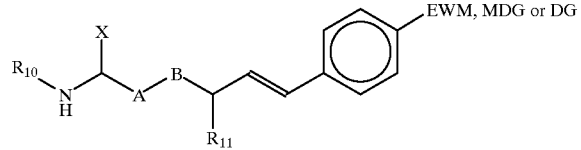

wherein
$R_{10}$=hydrogen, a peptide amino end blocking group, a peptide residue with or without an amino end blocking group, a single amino acid with or without an amino end blocking group, or a label;
X and $R_{11}$ are amino acid side chains, with either (R) or (S) stereochemical configuration;
the A—B linkage is a peptide residue or an isosteric form thereof;
EWM=an electron withdrawing moiety;
MDG=a meta directing group; and
DG=a deactivating group.

In a preferred embodiment, the cysteine protease inhibitors of the present invention have a vinylogous six membered heterocyclic aromatic ring with a substituted EWM as the EWG, as shown in Formula 15:

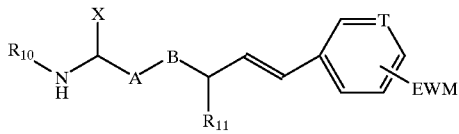

Formula 15 wherein
- $R_{10}$=hydrogen, a peptide amino end blocking group, a peptide residue with or without an amino end blocking group, a single amino acid with or without an amino end blocking group, or a label;
- X and $R_{11}$ are amino acid side chains, with either (R) or (S) stereochemical configuration;
- the A—B linkage is a peptide residue or an isosteric form thereof;
- T=a nitrogen or phosphorus atom; and
- EWM=an electron withdrawing moiety.

The EWM may also be attached to the "T" heteroatom.

In a further embodiment, the targeting group and the EWG are linked by a diene bond. By "diene bond" herein is meant a chain of four carbon atoms (C1, C2, C3, and C4) in which C1 and C2 are connected by a double bond, C3 and C4 are connected by a double bond, and C2 and C3 are connected by a single bond. In this embodiment, the targeting group is linked to the first carbon of the first carbon-carbon double bond (C1), and the EWG is linked to the last carbon of the second carbon-carbon double bond (C4). In a preferred embodiment, the two double bonds of the diene are in (E)-(E) configuration, although alternative embodiments utilize (E)-(Z), (Z)-(E), or (E)-(E) configurations.

In a preferred embodiment, the second order rate constant for inhibition of a cysteine protease with the diene bond cysteine protease inhibitor, expressed as $k_{irr}K_I$, is at least about 1000 $M^{-1}sec^{-1}$, with alterative embodiments having second order rate constants at least about 10,000 $M^{-1}sec^{-1}$, with the most preferred rate constant being at least about 100,000 $M^{-1}sec^{-1}$.

In this embodiment, the targeting group and EWG are defined as above.

In a preferred embodiment, the cysteine protease inhibitor comprises a compound with the formula:

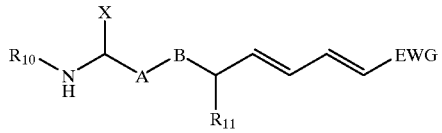

Formula 16 wherein
- $R_{10}$ is hydrogen, a peptide amino end blocking group, a peptide residue with or without an amino end blocking group, a single amino acid with or without an amino end blocking group, or a label;
- X and $R_{11}$ are amino acid side chains, with either (R) or (S) stereochemical configuration;
- A—B is a peptide linkage; and
- EWG is an electron withdrawing group.

In an additional embodiment, the cysteine protease inhibitors of the present invention comprise a targeting group linked via an alkene bond to two EWGs. In this embodiment, the targeting group is linked to one of the carbons of the carbon-carbon double bond, and the two EWGs are linked to the other carbon of the carbon-carbon double bond. The linkage of the targeting group to the alkene bond is as described above for the single EWG embodiment The linkage of the two EWGs to the alkene bond is similar as for one EWG; that is, the linkage is such that the electron withdrawing properties of the EWGs are exerted on the alkene bond, to allow nucleophilic attack by a cysteine protease on the alkene bond.

In this embodiment, preferably the two EWGs are different. In an alternative embodiment, the two EWGs are the same.

In a preferred embodiment, the cysteine protease inhibitor comprises a compound with the formula:

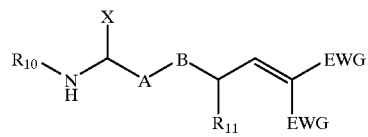

Formula 17 wherein
- $R_{10}$ is hydrogen, a peptide amino end blocking group, a peptide residue with or without an amino end blocking group, a single amino acid with or without an amino end blocking group, or a label;
- X and $R_{11}$ are amino acid side chains, with either (R) or (S) stereochemical configuration;
- A—B is a peptide linkage; and
- EWG is an electron withdrawing group.

In one embodiment, the cysteine protease inhibitors are comprised of a targeting group linked to an alkene bond conjugated with an electron withdrawing group (EWG).

In this embodiment, the second order rate constant for inhibition of a cysteine protease with the inhibitor, expressed as $k_{irr}/K_I$, is at least about 1000 $M^{-1}sec^{-1}$.

By the term "second order rate constant" or grammatical equivalents herein is meant the kinetic constant associated with a bimolecular reaction that is dependent on the concentration of two species. The second order rate constants are defined and determined as below.

The determination of second order rate constants is known in the art. For example, for irreversible inhibition reactions such as those of the present invention, the reaction scheme is as follows:

Equation 4

The reaction is divided into two processes. The enzyme and the inhibitor first combine to give an enzyme-inhibitor complex, E.I. This step is assumed to be rapid and reversible, with no chemical changes taking place; the enzyme and the inhibitor are held together by non-covalent forces. In this reaction, $k_1$ is the second order rate constant for the formation of the E.I reversible complex. $k_2$ is the first order rate constant for the disassociation of the reversible EI complex. The chemical processes then occur in a second step with a first order rate constant $k_{irr}$, which is the constant for the inactivation of the E.I complex, which is similar to the $k_{cat}$ constant or turnover number. In this reaction, $K_I=k_2/k_1$, and the second order rate constant of inactivation is $k_{irr}/K_I$.

The measurement of the first order rate constant $k_{irr}$ and the equilibrium constant $K_I$ proceeds according to techniques well known in the art, as described in the examples. For example, assays are run in the presence of inhibitor and substrate, generally using synthetic chromogenic substrates. Inhibition progress curve analysis using non-linear curve fitting software widely available enables the calculation of the first order rate constant $k_{irr}$ and the equilibrium constant $K_I$. The second order rate constant, $k_{irr}/K_I$, is then calculated as follows:

At equilibrium, $k_1[E][I]=k_2[E.I]$ or $$\frac{[E][I]}{[E \cdot I]} = \frac{k_2}{k_1} = K_I$$

where $K_I$ is a dissociation constant with units of M.
For the inactivation of E, $$\frac{d}{dt}E-I = v_{E-I} = k_{irr}[E \cdot I]$$

$$E_{total} = E + E \cdot I$$

$$K_I = \frac{[E][I]}{[E \cdot I]}$$

$$\frac{v_{E-I}}{[E_T]} = \frac{k_{irr}[E \cdot I]}{[E]+[E \cdot I]}$$

$$\frac{v_{E-I}}{[E_T]} = \frac{k_{irr}\frac{[E][I]}{K_I}}{[E]+\frac{[E][I]}{K_I}}$$

Eliminating [E]:

$$\frac{v_{E-I}}{[E_T]} = \frac{k_{irr}\frac{[I]}{K_I}}{1+\frac{I}{K_I}}$$

Using $K_I$ as a common denominator gives:

$$\frac{v_{E-I}}{[E_T]} = \frac{k_{irr}[I]}{K_I+[I]}$$

and:

$$v_{E-I} = \frac{k_{irr}[I][E_T]}{[I]+K_I}$$

$k_{irr}$ is the first order rate constant of inactivation of E.
When $[I]<<K_I$, the rate equation reduces to $$v_{E-I} = \frac{k_{irr}}{K_I}[I][E_T]$$

that is the pseudo-second order rate expression where $k_{irr}/K_I$ represents the pseudo-second order rate constant with units of $M^{-1}sec^{-1}$.

It is to be understood that second order rate constants are a particularly useful way of quantifying the efficiency of an enzyme with a particular substrate or inhibitor, and are frequently used in the art as such. The efficiency of an inhibitor depends on the second order rate constant and not on either the $K_I$ value alone or the $k_{irr}$ value alone. Thus even if an inhibitor exhibits a very low $K_I$, or alternatively a very high $k_{irr}$, it may not be a efficient inhibitor if the second order rate constant is low. Accordingly, the cysteine protease inhibitors of the present invention have second order rate constants, expressed as $k_{irr}/K_I$, of at least about $1000\ M^{-1}sec^{-1}$. Preferred embodiments have inhibitors that exhibit second order rate constants of at least about $10{,}000\ M^{-1}sec^{-1}$, with the most preferred embodiments having second order rate constants of at least about $100{,}000\ M^{-1}sec^{-1}$. In addition, the second order rate constants of the preferred embodiment do not exceed the diffusion limit of about $1\times10^8\ M^{-1}sec^{-1}$.

In the preferred embodiment, the cysteine protease inhibitors are chiral. In this embodiment, the chiral cysteine protease inhibitor is comprised of a targeting group linked to an alkene bond conjugated with an EWG. By the term "chiral" or grammatical equivalents herein is meant a compound that exhibits dissymetry. That is, the chiral compound is not identical with its mirror image. Thus in the preferred embodiment, the compounds of the present invention are pure epimers. Chiral compounds, and particularly chiral cysteine protease inhibitors, are useful in the present invention because biological systems, and enzymes in particular, are stereospecific, preferring the (S) or L-form of amino acids. Thus in the preferred embodiment, the chiral cysteine protease inhibitors of the present invention will have amino acid side chains in the (S) or L-configuration, although some inhibitors may utilize amino acid side chains in the (R) or D-configuration.

In alternative embodiments, the compositions of the present invention are not pure epimers, but are mixtures that contain more than 50% of one epimer. Preferred embodiments have greater than about 70% of one epimer, and the most preferred embodiment has at least about 90% of one epimer.

The synthesis of the cysteine protease inhibitors of the present invention proceeds as follows. In general, preparation of the inhibitors described herein requires first that the amino acids from which the inhibitory functionalities are derived, i.e. the targeting amino acids, be converted into t-butoxycarbonyl-protected a-aminoaldehydes, also called N-protected α-amino aldehydes, as shown in Equation 5 (for example by the method of Fehrentz, J-A. and Castro, B. (Synthesis, (1983), 676 (Equation 5)).

Equation 5

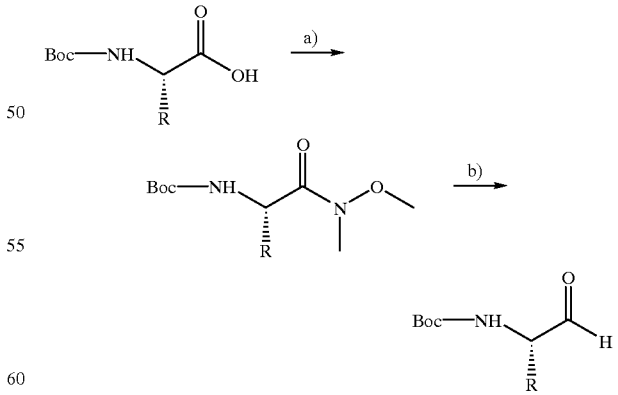

wherein
R=an amino acid side chain: alkyl, aryl, aminoalkyl, etc.;
a) Cl—$H_2$N+(Me)OMe, dicyclohexylcarbodiimide, triethylamine; and
b) lithium aluminum hydride.

The resulting aldehydes are transformed into vinylogous compounds using the Wadsworth-Emmons-Horner modification of the Wittig reaction to make cysteine protease inhibitor intermediates (Wadsworth et al., J. Amer. Chem. Soc. 83:1733 (1961); Equation 1).

In one embodiment, the vinylogous compounds, as cysteine protease inhibitor intermediates, may be used as cysteine protease inhibitors without further chemical addition, i.e. the inhibitors have only a single amino acid side chain, as depicted in Formula 16:

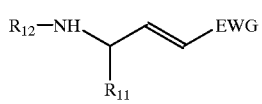

Formula 18 wherein $R_{12}$ is hydrogen or a peptide amino end blocking group;

$R_{11}$ any amino acid side chain except glycine (hydrogen), or, when the EWG is a vinylogous ester, phenylalanine (benzyl); and EWG is an electron withdrawing group.

For example, Boc-AspVSPh may be used as an inhibitor of ICE without further addition of amino acid side chain targeting groups.

In a preferred embodiment, additional targeting groups, in the form of amino acid side chains, are added to the vinylogous cysteine protease inhibitors to form the structure, depicted in Formula 1, above. Generally, this is done by deprotecting the $R_{10}$ group and coupling an additional N-protected amino acid, as is well own in the art.

Specifically, the cysteine protease inhibitors of the present invention that contain vinylogous esters as the EWG can be generated by the sequence of reactions shown in Scheme I below:

Scheme 1

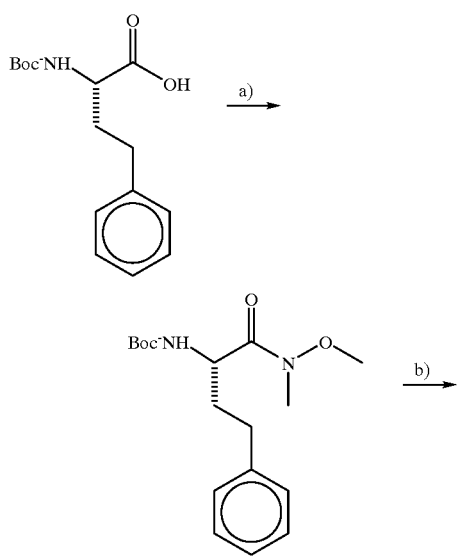

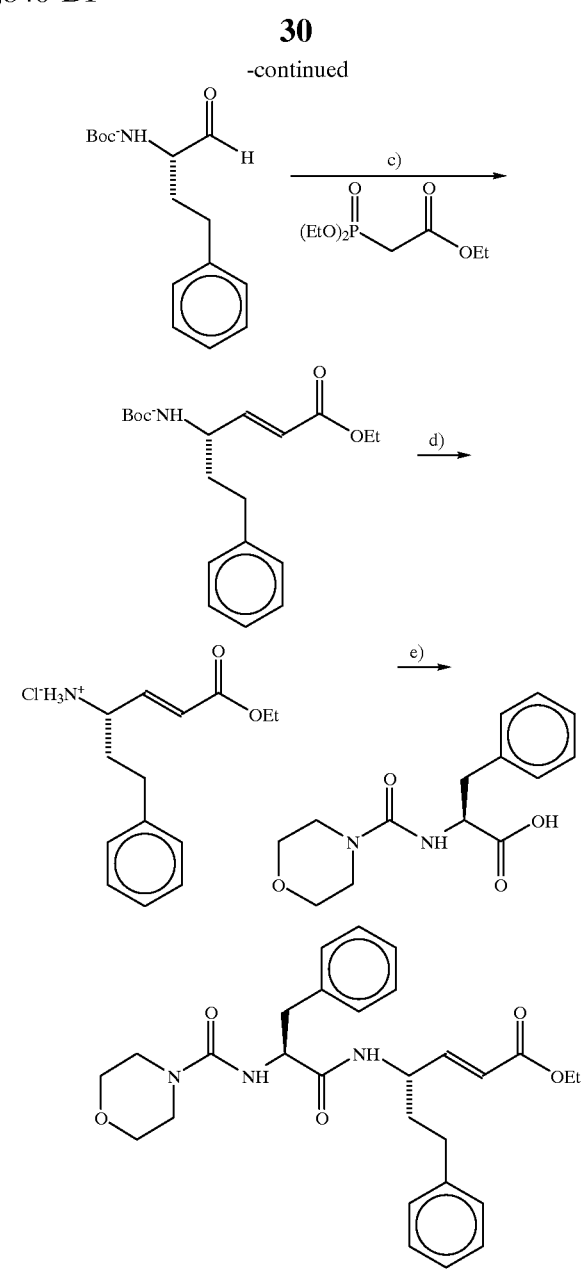

a) Cl—NH$_2$+(CH$_3$)OCH$_3$, dicyclohexylcarboiimide, Et$_3$N/CH$_2$Cl$_2$;
b) LiAlH$_4$/THF;
c) NaH/THF;
d) HCl/dioxane/CH$_2$Cl$_2$; and
e) 4-methylmorpholine, isobutyl chloroformate/THF.

A preferred embodiment treats Boc-protected amino acids such as homophenylalanine, depicted as the example of Scheme 1, with N,O-dimethylhydroxylamine hydrochloride, in the presence of triethylamine and dicyclohexylcarbodiimide in dichloromethane.

Alternative embodiments treat the Boc-protected amino acids in the presence of triethylamine and the coupling reagent benzotriazol-1-yloxytris (dimethylamino)-phosphonium hexafluorophosphate (BOP). Subsequent reduction with lithium aluminum hydride results in Boc-a-amino aldehydes, for example using the method of Fehrentz, J-A. and Castro, B. (Synthesis, (1983), 676–678). The resulting aldehydes are then treated with the sodium anion of triethyl phosphonoacetate, in the manner of Wadsworth, W. S. and Emmons, W. D. (J. Am. Chem. Soc. (1961), 83, 1733, to produce the vinylogous esters of the present invention. These vinylogous esters are then deprotected with hydrogen chloride in dioxane, and coupled with N-protected amino acids to form pseudopeptidyl vinylogous esters, the cysteine protease inhibitors of this embodiment. Coupling is acheived via mixed anhydride or other peptide coupling reaction sequences known to those skilled in the art.

In a preferred embodiment, the cysteine protease inhibitors of the present invention that contain vinylogous sulfones as the EWG can be generated by the sequence of reactions shown in Scheme II below:

Scheme II

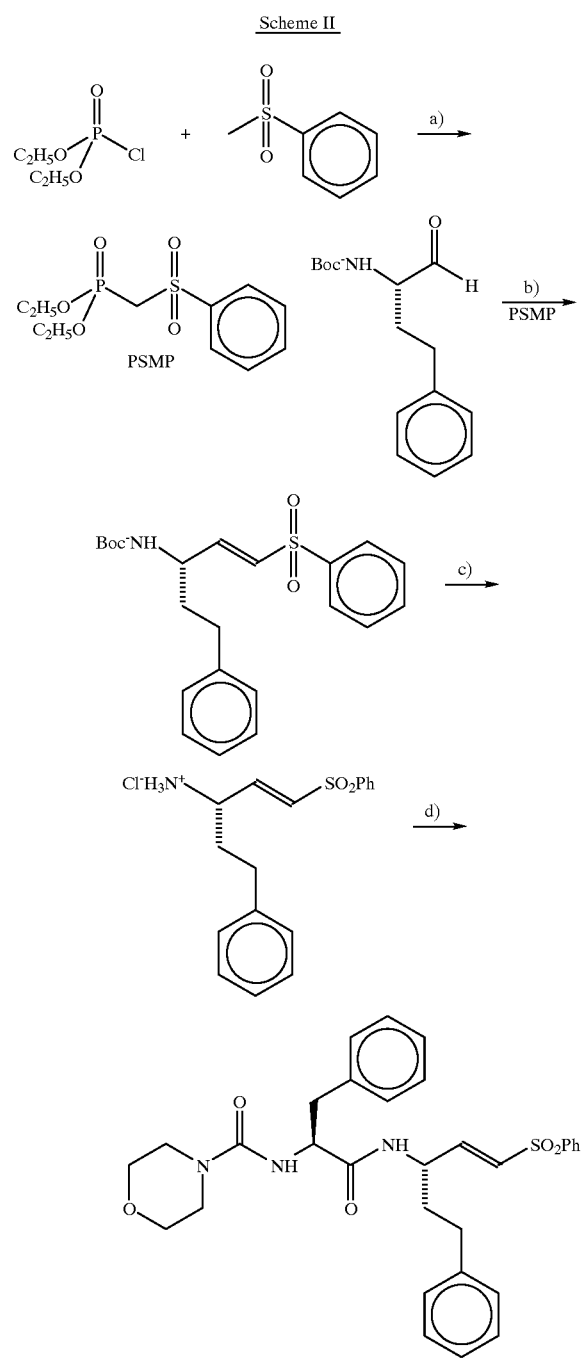

-continued a) butylithium/THF; b) NaH/THF; c) HCl/dioxane;
d) Mu-PheOH, 4-methylmorpholine, isobutyl chloroformate/THF.

Generally, the preferred embodiment utilizes Boc-a-amino aldehydes, prepared according to the method of Fehrentz, J-A. and Castro, B. (Synthesis, (1983). Treatment of these aldehydes with the sodium anion of sulfonylmethanephosphonates, for example diethyl phenylsulfonylmethanephosphonate, results in the corresponding vinylogous sulfone derivatives, in the manner of Wadsworth, W. S. and Emmons, W. D. (J. Am. Chem. Soc. (1961), 83, 1733. In one embodiment, sulfonyl methanephosphonates are synthesized by coupling of the alkali metal anion of sulfones such as methyl phenyl sulfone with diethyl chlorophosphate.

Alternative embodiments utilize m-chloroperbenzoic acid oxidation of commercially available sulfides such as diethylphosphonomethyl methyl sulfide (Aldrich Chemical Co.). The vinylogous sulfones are then deprotected with hydrogen chloride in dioxane, and are coupled with N-protected amino acids to form pseudopeptidyl vinylogous sulfones, using techniques well known in the art.

The vinylogous carboxylates of this embodiment are made using the sequence of reactions shown in Scheme III below:

Scheme III

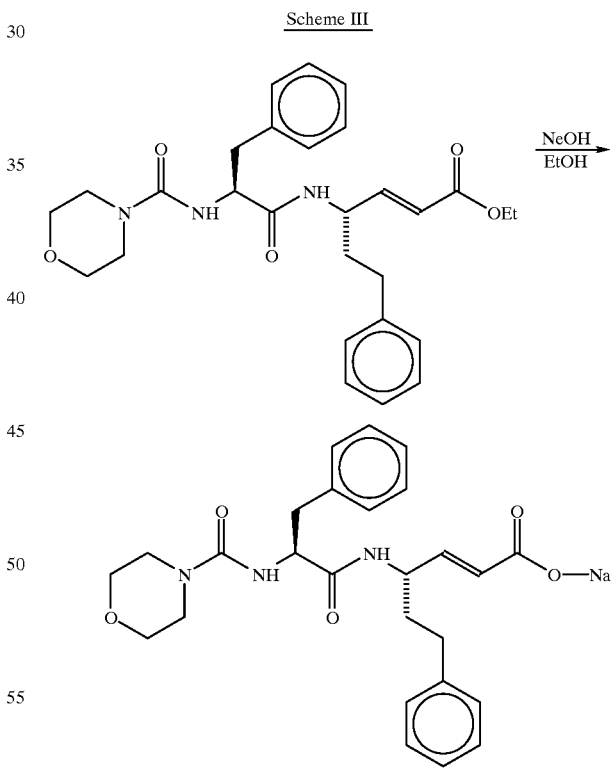

Generally, saponification of the ester functionality of the vinylogous esters, described above, results in carboxylates. Acidification, as is known in the art, gives the corresponding carboxylic acids.

The cysteine protease inhibitors of the present invention that contain vinylogous phosphonates as the EWG may be synthesized by the sequence of reactions shown in Scheme IV:

Scheme IV

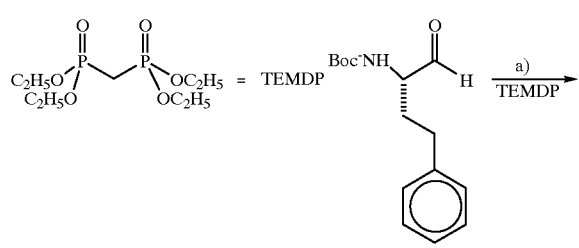

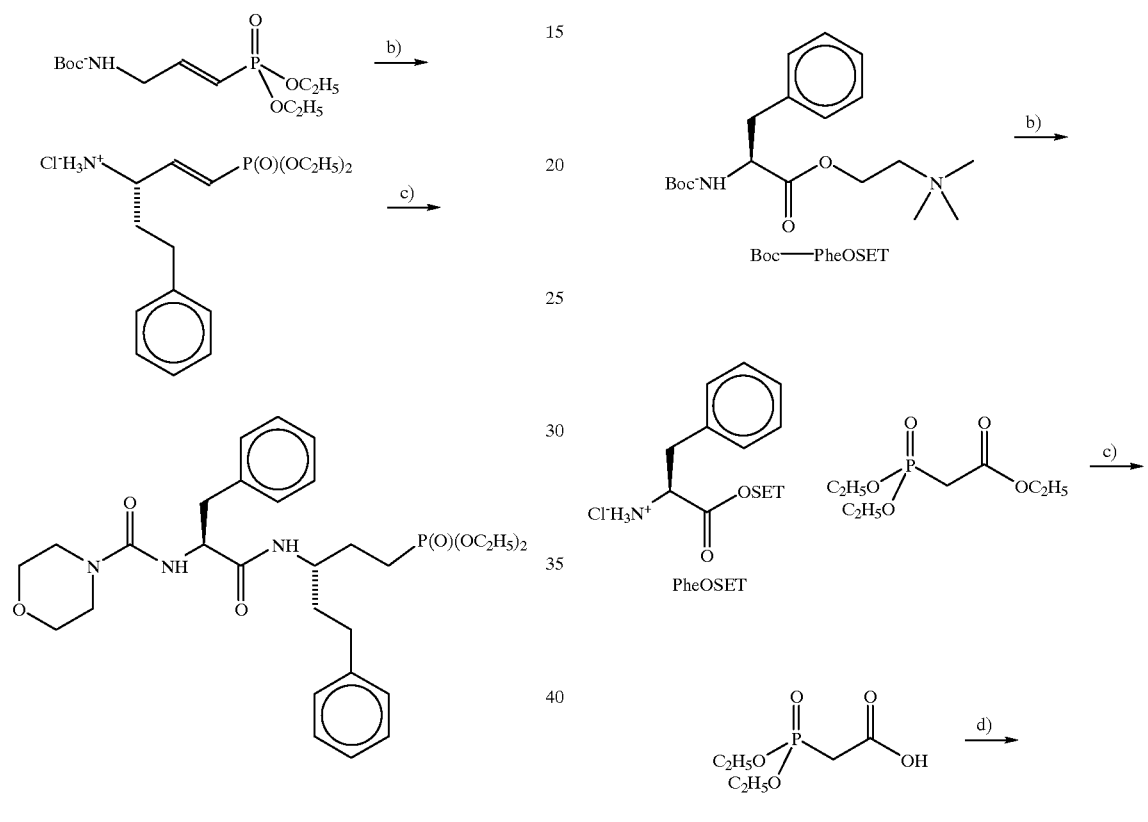

a) NaH/THF;

b) HCl/dioxane; and c) Mu-PheOH, 4-methylmorpholine, isobutyl chloroformate/THF.

Generally, vinylogous phosphonate derivatives are made by treating Boc-a-amino aldehydes, prepared according to the method of Fehrentz, J-A. and Castro, B. (Synthesis, (1983), with the sodium anion of methylenediphosphonates, for example tetraethyl methylenediphosphonate. The vinylogous phosphonate derivatives are then deprotected with hydrogen chloride in dioxane, and coupled with N-protected amino acids to form pseudopeptidyl vinylogous phosphonates using techniques known to those skilled in the art.

The vinylogous amides and peptide derivatives of this invention can be generated by the sequence of reactions shown in Scheme V.

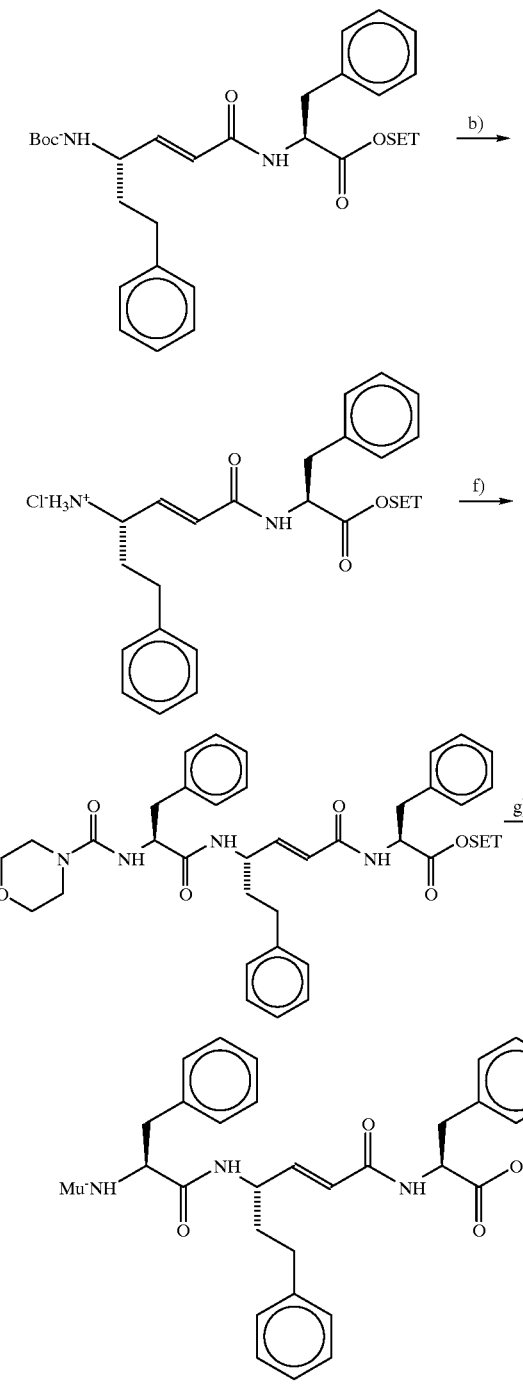

a) (CH₃)₃SiCH₂CH₂OH, dicyclohexylcarbodiimide (DCC), (C₂H₅)₃N, 4-dimethylamino-pyridine, CH₂Cl₂;
b) HCl/dioxane;
c) NaOH/C₂H₅OH;
d) PheOSET, DCC, (C₂H₅)₃N, CH₂Cl₂;
e) NaH, EPAc-PheOSET, THF;
f) Mu-PheOH, 4-methylmorpholine, isobutyl chloroformate, THF; and
g) (n-C₄H₉)₄N+F-, 3 Å molecular sieves, THF.

The N-Boc amino acid, protected as its silylethyl (SET) ester, is N-deprotected, then coupled with the saponification product of triethyl phosphonoacetate. The diethyl phosphonoacetyl amino acid derivative is then coupled, in Wadsworth-Emmons fashion, with the appropriate Boc-protected a-amino aldehyde. Further elongation of the peptide sequence is concluded with fluoride-assisted deprotection of the SET moiety to afford the vinylogous amide.

Generally, to ensure that the double bond remains intact during the preparation of the vinylogous amides bound to peptide chains in that the C-terminus is to be converted to the free carboxylate or carboxylic acid group, the fluoride-cleavable silyethyl (SET) esters are used. Thus saponification conditions, which cause product mixtures resulting from both ester hydrolysis and 1,4-addition of hydroxide to the vinylogous amide at high pH, are avoided. The SET protection scheme therefore permits clean, smooth preparation of peptide sequences prior to the key Wadsworth-Emmons coupling with an eye to carboxylate formation if the C-terminus is to be a free acid.

The cysteine protease inhibitors of the present invention that contain vinylogous ketones, nitriles, sulfoxides, sulfonamides, sulfinamides, sulfonates and sulfoximines as the EWG may be synthesized as follows using the general scheme outlined in Scheme VI:

Scheme VI

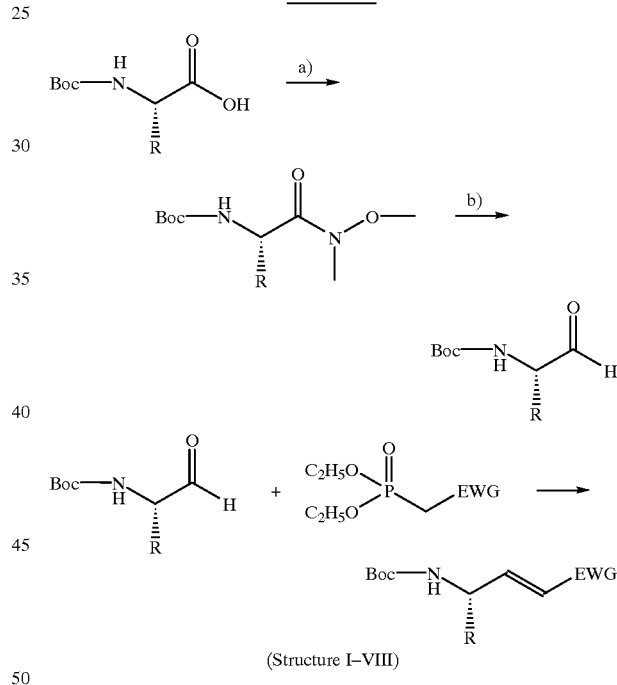

(Structure I–VIII)

wherein
a) Cl—H₂N+(Me)OMe, dicyclohexylcarboniimide, triethylamine; and
b) lithium aluminum hydride.

Structure (I–VIII) are as follows. For the synthesis of cysteine protease inhibitors with vinylogous ketones as the EWG, structure I is used:

Structure I

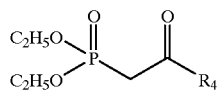

Synthesis of α,β-unsaturated ketones is performed by means of the Wadsworth-Emmons reaction between Boc-α- amino aldehydes and the appropriate phosphonate. Generally, the aldehyde portion is synthesized as outlined above. The phosphonate is synthesized by treatment of the enolate anion of methyl or substituted methyl ketones, such as acetone or acetophenone, with diethyl chlorophosphonate. The enolate anion is generated, for example, by treatment of a tetrahydrofuran solution of diisopropylamine with butyllithium, followed by addition of the ketone to the lithium diisopropylamide (LDA) solution (H.O. House, Modern Synthetic Reactions, 2and Ed. (W. Benjamin, Inc., Menlo Park, Calif., Chapter 9). Following formation of the enolate, diethyl chlorophosphonate is added. The Wadsworth-Emmons reagent forms as a consequence of coupling of the enolate with diethyl chlorophosphate.

For the synthesis of cysteine protease inhibitors with vinylogous nitrites as the EWG, structure II is used:

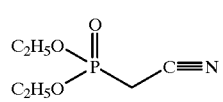

Structure II

Synthesis of α,β-unsaturated nitrites is performed by means of the Wadsworth-Emmons reaction between Boc-α-amino aldehydes and the appropriate phosphonate. Generally, the aldehyde portion is synthesized as outlined above. The phosphonate is commercially available.

For the synthesis of cysteine protease inhibitors with vinylogous sulfoxides as the EWG, structure III is used:

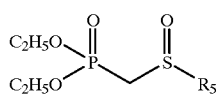

Structure III

Synthesis of α,β-unsaturated sulfoxides is performed by means of the Wadsworth-Emmons reaction between Boc-α-amino aldehydes and the appropriate phosphonate. Generally, the aldehyde portion is synthesized as outlined above. The phosphonate is synthesized by treatment of the anion of methyl sulfoxides with diethyl chlorophosphate. The anion is generated by addition of BuLi to diisopropylamine, followed by addition of the methyl sulfoxide.

For the synthesis of cysteine protease inhibitors with vinylogous sulfonamides as the EWG, structure IV is used:

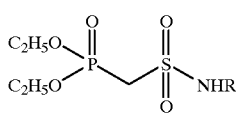

Structure IV

Synthesis of α,β-unsaturated sulfonamides is performed by means of the Wadsworth-Emmons reaction between Boc-α-amino aldehydes and the appropriate phosphonate. Generally, the aldehyde portion is synthesized as outlined above. The phosphonate is synthesized, for instances, by a method such as the following: a) diethylphosphoryl methanesulfonates, as prepared by the method of Carretero and Ghosez (Tetrahedron Lett., 28:1104–1108 (1987)), are converted to sulfonyl chlorides by treatment with phospho rus pentachloride (M. Quaedvlieg, in "Methoden der Organische Chemie (Houben-Weyl)", ed. E. Muller, Thieme Verlag, Stuttgart, 4th Ed., 1955, Vol. IX, Chapter 14); or b) treatment of the sulfonyl chloride with an amine, such as ammonia, a primary amine (including an amino acid derivative), or a secondary amine, that results in the formation of the sulfonamide (Quaedvlieg, supra, Chapter 19). The sulfonamide-phosphonate is then reacted with Boc-α-aminoaldehydes to form the target compounds as per the Wadsworth-Emmons reaction.

For the synthesis of cysteine protease inhibitors with vinylogous sulfinamides as the EWG, structure V is used:

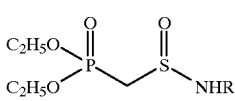

Structure V

Synthesis of α,β-unsaturated sulfinamides is performed by means of the Wadsworth-Emmons reaction between Boc-α-amino aldehydes and the appropriate phosphonate. Generally, the aldehyde portion is synthesized as outlined above. The phosphonate may be synthesized using one of the following methods. Treatment of methyl dialkyl phosphonates such as the commercially available methyl diethyl phosphonate (Aldrich), with thionyl chloride in the presence of aluminum chloride gives the dialkylphosphoryl methanesulfinyl chloride (Vennstra et al., Synthesis (1975) 519. See also Anderson, "Comprehensive Organic Chemistry (Pergamon Press)", Vol. 3, Chapter 11.18, (1979). Alternatively, treatment of the dialkyl phosphoryl sulfinyl chloride amines (Stirling, Internat. J. Sulfur Chem. (B) 6:277 (1971)), yields the dialkyl phosphoryl sulfinamide.

For the synthesis of cysteine protease inhibitors with vinylogous sulfoximines as the EWG, structure VI is used:

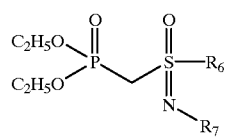

Structure VI

Synthesis of α,β-unsaturated sulfoximines is performed by means of the Wadsworth-Emmons reaction between Boc-α-amino aldehydes and the appropriate phosphonate. Generally, the aldehyde portion is synthesized as outlined above. The phosphonate may be synthesized in several ways. For example, N-alkyl or N-aryl phenyl methyl sulfoximines are made by the methods described by Johnson, in "Comprehensive Organic Chemistry (Pergamon Press), supra, Chapter 11.11. Alternatively, the lithium anion of compounds such as N-alkyl phenyl methyl sulfoximine is prepared by the treatment of the neutral compound with buthyl lithium in THF (Cram et al., J. Amer. Chem. Soc. 92:7369 (1970)). Reaction of this lithium anion with dialkyl chlorophosphates such as the commercially available diethyl chlorophosphate (Aldrich) results in the Wadsworth-Emmons reagent necessary for synthesis of the sulfoximine compounds.

For the synthesis of cysteine protease inhibitors with vinylogous sulfonates as the EWG, structure VII is used:

Structure VII

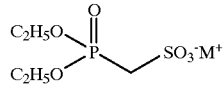

Synthesis of α,β-unsaturated sulfonates is performed by means of the Wadsworth-Emmons reaction between Boc-α-amino aldehydes and the appropriate phosphonate, for instance diethylphosphoryl methanesulfonate. The phosphonate may be synthesized as follows. The anion of methyl dialkyl phosphonates such as the commercially available methyl diethyl phosphonate (Aldrich) is generated by treatment of said phosphonate with a strong base such as LDA. The resulting anion is sulfonated with sulfur trioxide/ trimethylamine complex (Carreto et al., Tetrahedron Lett., 28:1104–1108 (1987)) to form diethylphosphoryl methanesulfonate, which is capable of reacting in the Wadsworth-Emmons procedure with aldehydes to form α,β-unsaturated sulfonates.

For the synthesis of cysteine protease inhibitors with vinylogous nitro compoundss as the EWG, structure VIII is used:

Structure VIII

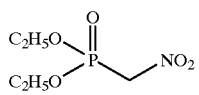

Synthesis of α,β-unsaturated nitro compounds is performed by means of the Wadsworth-Emmons reaction between Boc-α-amino aldehydes and the appropriate phosphonate. The phosphonate is synthesized by treatment of the enolate anion of nitromethane with diethyl chlorophosphate. The enolate anion is generated, for example, by treatment of a tetrahydrofuran solution of diisopropylamine with butyllithium, followed by addition of nitromethane to the lithium diisopropylamide (LDA) solution (House, supra). Following formation of the enolate, diethyl chlorophosphate is added. The Wadsworth-Emmons reagent forms as a consequence of coupling of the nitromethane anion with diethyl chlorophosphate.

For the synthesis of cysteine protease inhibitors with EWGs comprising five or six homo- or heterocyclic aromatic rings with at least one substituted EWG group, scheme VII is used:

Scheme VII

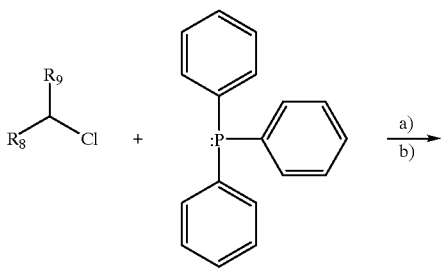

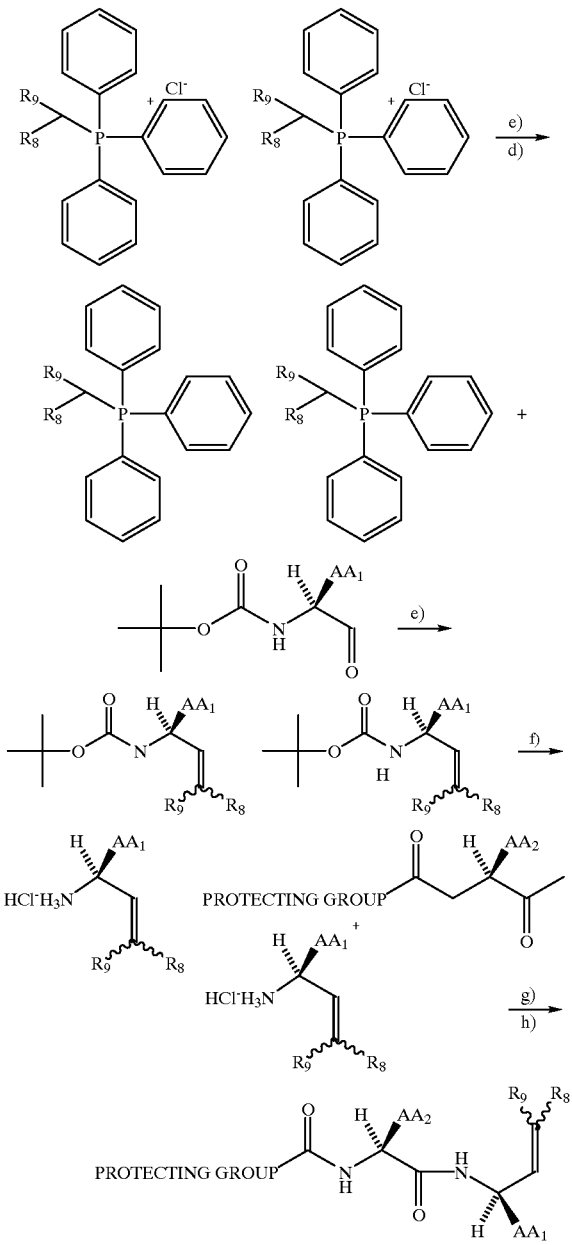

Wherein
a) heat at reflux;
b) solvent;
c) H$_2$O/NaOH;
d) organic extraction;
e) mix;
f) HCl/dioxane 4M;
g) couple;
h) base; and
R$_8$=the five or six homo- or heterocyclic aromatic rings with at least one substituted EWM, MDG, or DG; and
R$_9$=a suitable group as defined above.

The chloride compounds containing R$_8$ and R$_9$ groups are generally made using commercially available reagents and products using techniques well known in the art. The reaction generally produces a mixture of cis and trans configurations.

Cysteine protease inhibitors containing a diene bond instead of a single alkene bond are made using the same general synthetic scheme as outlined above, by repeating the reaction, as shown below in Scheme VIII:

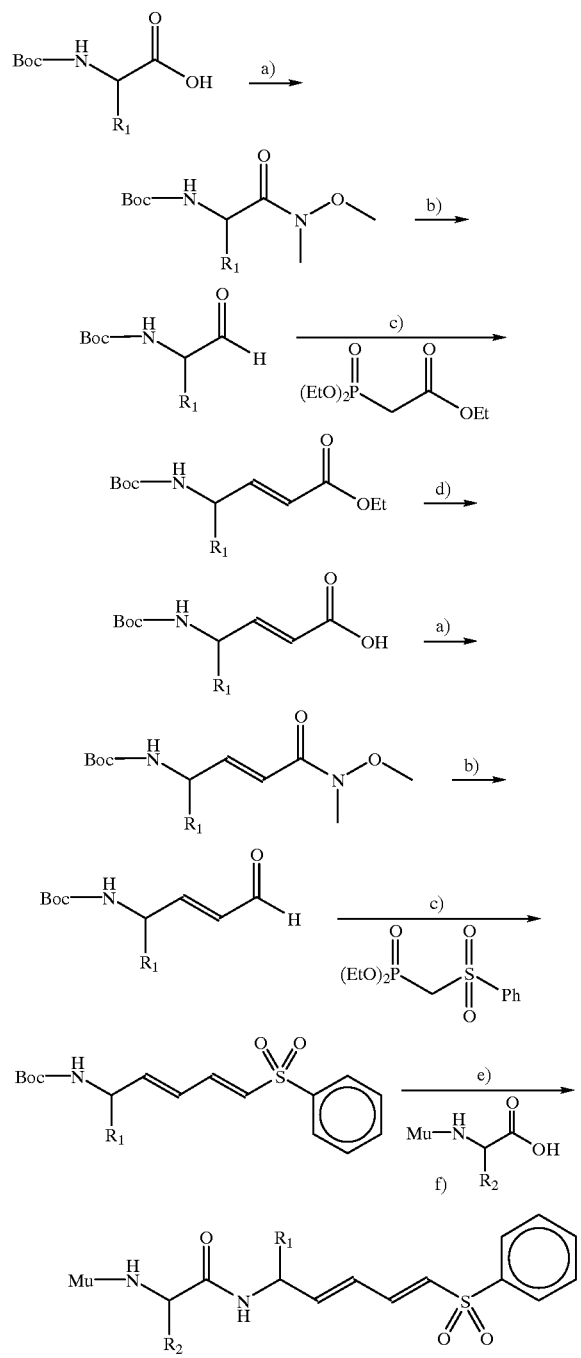

a) NHCH$_3$OCH$_3$•HCl, dicyclohexylcarbodiimide,Et$_3$N/CH$_2$Cl$_2$;
b) LiAlH$_4$/THF; c) NaH/THF; d) NaOH, H$_2$O, EtOH;
e) HCl/dioxane/CH$_2$Cl$_2$; f) 4-methylmorpholine, isobutyl chlorofomate/THF The cysteine protease inhibitors which contain two EWGs linked to one of the carbons of the alkene bond may be synthesized using, for example, the methods disclosed in Brillon et al., J. Org. Chem. 57:1838–1842 (1992), hereby expressly incorporated by reference.

In one embodiment, the cysteine protease inhibitors of the present invention are further purified if necessary after synthesis, for example to remove unreacted materials. For example, the cysteine protease inhibitors of the present invention may be crystallized, or passed through silica chromatography columns using solvent mixtures to elute the pure inhibitors.

In particular, the cysteine protease inhibitors of the present invention synthesized through the use of the Wittig reaction may be further purified to isolate either the cis or trans configuration. For example, the techniques outlined above may be used.

Once produced, the cysteine protease inhibitors of the present invention may be easily screened for their inhibitory effect. The inhibitor is first tested against the cysteine protease for that the targeting group of the inhibitor was chosen, as outlined above. Alternatively, many cysteine proteases and their corresponding chromogenic substrates are commercially available. Thus, a variety of cysteine proteases are routinely assayed with synthetic chromogenic substrates in the presence and absence of the cysteine protease inhibitor, to confirm the inhibitory action of the compound, using techniques well known in the art. The effective inhibitors are then subjected to kinetic analysis to calculate the $k_{irr}$ and $K_I$ values, and the second order rate constants determined. This is done using techniques well known in the art; for example, progress curve analysis using non-linear curve fitting software can be done to determine the first order rate constants. Such software is sold under such tradenames as Sigma Plot (Jandel Scientific Corp.) and Statview (Abacus Concepts, Inc.).

If a compound inhibits at least one cysteine protease, it is a cysteine protease inhibitor for the purposes of the invention. Preferred embodiments have inhibitors that exhibit the correct kinetic parameters against at least the targeted cysteine protease.

In some cases, the cysteine protease is not commercially available in a purified form. The cysteine protease inhibitors of the present invention may also be assayed for efficacy using biological assays. For example, the inhibitors may be added to cells or tissues that contain cysteine proteases, and the biological effects measured.

In one embodiment, the cysteine protease inhibitors of the present invention are synthesized or modified such that the in vivo and in vitro proteolytic degradation of the inhibitors is reduced or prevented. Generally, this is done through the incorporation of synthetic amino acids, derivatives, or substituents into the cysteine protease inhibitor. Preferably, only one non-naturally occurring amino acid or amino acid sidechain is incorporated into the cysteine protease inhibitor, such that the targeting of the inhibitor to the enzyme is not significantly affected. However, some embodiments that use longer cysteine protease inhibitors containing a number of targeting residues may tolerate more than one synthetic derivative. In addition, non-naturally occurring amino acid substituents may be designed to mimic the binding of the naturally occurring side chain to the enzyme, such that more than one synthetic substituent is tolerated.

In this embodiment, the resistance of the modified cysteine protease inhibitors may be tested against a variety of known commercially available proteases in vitro to determine their proteolytic stability. Promising candidates may then be routinely screened in animal models, for example using labelled inhibitors, to determine the in vivo stability and efficacy.

In one embodiment, the cysteine protease inhibitors of the present invention are labelled. By a "labelled cysteine protease inhibitor" herein is meant a cysteine protease inhibitor that has at least one element, isotope or chemical compound attached to enable the detection of the cysteine protease inhibitor or the cysteine protease inhibitor irreversible bound to a cysteine protease. In general, labels fall into three classes: a) isotopic labels, which may be radioactive or heavy isotopes; b) immune labels, which may be antibodies or antigens; and c) colored or fluorescent dyes. The labels may be incorporated into the cysteine protease inhibitor at any position. For example, a label may be attached as the $R_{10}$ group in Formula 1. Examples of useful labels include $^{14}C$, $^{3}H$, biotin, and fluorescent labels as are well known in the art.

In one embodiment, compositions comprising chiral vinylogous phosphonates are provided. These chiral vinylogous phosphonates are derived from α-amino acids; that is, α-amino acids are used to generate the (α-amino aldehydes used in the synthesis. This novel class of compounds may be used in a preferred embodiment as cysteine protease inhibitors.

In one embodiment, compositions comprising chirally pure vinylogous sulfones derived from ax-amino acids are provided. This novel class of compounds may be used in a preferred embodiment as cysteine protease inhibitors.

Also provided are methods for inhibiting cysteine proteases using the cysteine protease inhibitors of the present invention. In the preferred embodiment, a cysteine protease inhibitor is irreversibly bound to a cysteine protease. This is accomplished using ordinary techniques, and will normally require contacting or adding the cysteine protease inhibitor to the sample of the cysteine protease to be inhibited. The cysteine protease inhibitors of the present invention are stoichiometric inhibitors; that is, a single inhibitor molecule will inhibit a single enzyme molecule. Thus in the preferred embodiment, an excess of inhibitor is added to ensure it all or most of the protease is inhibited. In alternative embodiments, only a portion of the protease activity is inhibited. In some embodiments, the cysteine protease inhibitor is labelled, such that the presence of a cysteine protease is detected after the excess inhibitor is removed. This may be done for example in a diagnostic assay for the detection or quantification of cysteine proteases in a sample, for example, in blood, lymph, saliva, skin or other tissue samples, in addition to bacterial, fungal, plant, yeast, viral or mammalian cell cultures.

In the preferred embodiment, the cysteine protease inhibitors of the present invention are administered to a patient to treat cysteine protease-associated disorders. By "cysteine protease-associated disorders" or grammatical equivalents herein is meant pathological conditions associated with cysteine proteases. In some disorders, the condition is associated with increased levels of cysteine proteases; for example, arthritis, muscular dystrophy, inflammation, tumor invasion, and glomerulonephritis are all associated with increased levels of cysteine proteases. In other disorders or diseases, the condition is associated with the appearance of an extracellular cysteine protease activity that is not present in normal tissue. In other embodiments, a cysteine protease is associated with the ability of a pathogen, such as a virus, to infect or replicate in the host organism.

Specific examples of cysteine protease associated disorders or conditions include, but are not limited to, arthritis, muscular dystrophy, inflammation, rumor invasion, glomerulonephritis, malaria, Aizheimer's disease, disorders associated with autoimmune system breakdowns, periodontal disease, cancer metastasis, trauma, inflammation, gingivitis, leishmaniasis, filariasis, and other bacterial and parasite-borne infections, and others outlined above.

In particular, disorders associated with interleukin 1β converting enzyme (ICE) are included, as outlined above.

In this embodiment, a therapeutically effective dose of a cysteine protease inhibitor is administered to a patient. By "therapeutically effective dose" herein is meant a dose that produces the effects for that it is administered. The exact dose will depend on the disorder to be treated and the amount of cysteine protease to be inhibited, and will be ascertainable by one skilled in the art using known techniques. In general, the cysteine protease inhibitors of the present invention are administered at about 1 to about 1000 mg per day. For example, as outlined above, some disorders are associated with increased levels of cysteine proteases. Due to the 1:1 stoichiometry of the inhibition reaction, the dose to be administered will be directly related to the amount of the excess cysteine protease. In addition, as is known in the art, adjustments for inhibitor degradation, systemic versus localized delivery, and rate of new protease synthesis, as well as the age, body weight, general health, sex, diet, time of administration, drug interaction and the severity of the disease may be necessary, and will be ascertainable with routine experimentation by those skilled in the art.

A "patient" for the purposes of the present invention includes both humans and other animals and organisms. Thus the methods are applicable to both human therapy and veterinary applications. For example, the veterinary applications include, but are not limited to, canine, bovine, feline, porcine, equine, and ovine animals, as well as other domesticated animals including reptiles, such as iguanas, turtles and snakes, birds such as finches and members of the parrot family, rabbits, rodents such as rats, mice, guinea pigs and hamsters, amphibians, and fish. Valuable non-domesticated animals, such as zoo animals, may also be treated. In the preferred embodiment the patient is a mammal, and in the most preferred embodiment the patient is human.

The administration of the cysteine protease inhibitors of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the cysteine protease inhibitors may be directly applied as a solution or spray.

The pharmaceutical compositions of the present invention comprise a cysteine protease inhibitor in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference.

EXAMPLES

The following abbreviation conventions have been used to simplify the examples.

Mu=morpholine urea $Xaa_1$=amino acid at P1 position relative to active site of the enzyme $Xaa_2$=amino acid at P2 position relative to active site of the enzyme $Xaa_{1'}$=amino acid at P1' position relative to active site of the enzyme VSMe=vinyl sulfone with methyl terminus VA=vinyl carboxylate VAM-$Xaa_{1'}$=vinyl amide coupled to amino acid 3;

VEOEt=vinyl ethyl ester

VPEt=vinyl phosphonate

VSPh=vinyl sulfone with phenyl terminus

Hph=homophenylalanine

For instance, Mu-Phe-Lys(Z)VSPh, where $Xaa_2$=Phe (phenylalanine) and $Xaa_1$=Lys(Z) (lysine, protected as its carbobenzyloxy urethane), transformed to the phenyl vinyl sulfone according to the procedure described in Example 5 and depicted in Scheme 2.

Example 1

Synthesis of Cysteine Protease Inhibitor Containing a Vinylogous Ethyl Ester

Unless otherwise indicated, all reactions were performed under an inert atmosphere of argon or nitrogen at room temperature. THF was distilled from sodium benzophenone ketyl. All other solvents and commercially available reagents were used without further purification.

Synthesis of Ethyl (S)-(E)-4-(4-morpholinecarbonyl-phenylalanyl)amino-6-phenyl-2-hexenoate, abbreviated Mu-Phe-HphVEOEt, was as follows. Unless otherwise noted, all reagents were obtained from Aldrich, Inc. 0.393 g of a 60% mineral oil dispersion (9.82 mmol) of sodium hydride was added to a solution of triethyl phosphonoacetate (2.20 g, 9.82 mmol) in THF (50 mL) at −10° C. The mixture was stirred for 15 minutes, whereupon solution of Boc-homophenylalaninal (Boc-HphH) (2.35 g, 9.82 mmol, prepared by conversion of Boc-homophenylalanine (Synthetech) to its N,O-dimethylhydroxamide, using the Fehrentz method, followed by lithium aluminum hydride reduction) in THF (20 mL) was added. The mixture was stirred for 45 minutes. 1M HCl (30 mL) was added. The product was extracted with ethyl acetate (50 mL), washed with saturated aqueous $NaHCO_3$ (30 mL) dried over $MgSO_4$, filtered, and evaporated to dryness. The dried material was dissolved in $CH_2Cl_2$ (10 mL), and a 4.0 M solution of HCl in dioxane (20 mL) was added. The mixture was stirred for 30 minutes. The solvents were removed under reduced pressure and the residue, ethyl (S)-4-amino-6-phenyl-2-hexenoate hydrochloride, was pumped dry.

Morpholinecarbonylphenylalanine (2.74 g, 9.82 mmol, prepared according to the method described in Esser, R. et.al., Arthritis & Rheumatism (1994), 0000) was dissolved in THF (50 mL) at −10° C. 4-methylmorpholine (1.08 mL, 9.82 mmol) was added, followed by isobutyl chloroformate (1.27 mL, 9.82 mmol). The mixed anhydride was stirred for 10 minutes, whereupon a solution of ethyl (S)-4-amino-6-phenyl-2-hexenoate hydrochloride from the previous step in DMF (10 mL) was added, followed by 4-methylmorpholine (1.08 mL, 9.82 mmol). The mixture was stirred for 1 hour. 1M HCl (50 mL) was added. The product was extracted with ethyl acetate (100 mL), washed with saturated aqueous $NaHCO_3$ (50 mL), dried over $MgSO_4$ and decolorizing charcoal (DARCO), filtered, and evaporated to dryness, giving 3.80 g (80% yield from Boc-homophenylalaninal).

Thin-layer chromatography (TLC) was done. Unless otherwise noted, all data for this and subsequent examples used 10% MeOH/$CH_2Cl_2$. Visualization was accomplished by means of UV light at 254 nm, followed by ninhydrin, bromocresol green, or p-anisaldehyde stain. The retention factor (Rf) of the Mu-Phe-HphVEOEt was 0.55.

NMR spectra were recorded on a Varian Gemini 300 MHz instrument. All $^1H$ NMR data of this and subsequent examples are reported as delta values in parts per million relative to internal tetramethylsilane, peak assignments in boldface. The following abbreviations are used: s, singlet; d, doublet; t, triplet; q, quartet; br, broad. An asterisk (*) implies that a signal is obscured or buried under another resonance.

$^1H$ NMR (CDCl$_3$): 1.28 (3H, t, J=6 Hz, CH$_3$); 1.7–1.95 (m, 2H, CH$_2$CH$_2$Ph); 2.59 (2H, CH$_2$CH$_2$Ph); 2.99–3.17 (2H, 2×dd, J=7,15 Hz and 5,15 Hz, PhCH$_2$ of Phe residue); 3.26 (4H, m, 2×CH$_2$O (morpholine)); 3.61 (4H, m, 2×CH$_2$N (morpholine)); 4.39 (q, J=6 Hz, CH$_2$ (ester)); 4.47–4.6 (2H, m*, 2×CHNH); 5.06 (1H, d, J=7 Hz, NHCH), 5.65 (1H, d, J=15 Hz, trans COCH=CH,); 6.15 (1H, d, J=7 Hz, NHCH); 6.67 (1H, dd, J=5,15 Hz, trans CH=CHCO); 7.09–7.36 (10H, m, aromatic).

Mass spectral data were obtained from M-Scan, Inc., West Chester, Pa. FAB, high-resolution: calculated for $C_{28}H_{35}N_3O_5$, (m+H)=494.2655, found, 494.2638.

Indication of approximately a 7:1 ratio of (S) to (R) epimers was evidenced by the appearance of a doublet at 5.82 ppm (J=15 Hz) coupled to a doublet of doublets at 6.79 (J=5,15 Hz). This phenomenon is possibly due to isomerically impure commercial material.

Example 2

Synthesis of Cysteine Protease Inhibitor Containing a Vinylogous Ethyl Ester

Ethyl (S)-(E)-7-guanidino-4-(4-morpholinecarbonylphenylalanyl)amino-2-heptenoate hydrobromide, abbreviated MU-Phe-ArgVEOEt.HBr, was made as follows. Boc-$N_g$-4methoxy-2,3,6-trimethylbenzenesulfonylarginine Boc-Arg(Mtr)OH) was converted to its aldehyde, abbreviated as Boc-Arg(Mtr)H according to the method of Fehrentz and Castro, supra. To a solution of triethyl phosphonoacetate (0.916 mL, 3.61 mmol) in THF (20 mL) was added NaH (0.145 g of a 60% mineral oil dispersion, 3.61 mmol). The solution was stirred for 15 minutes. A solution of Boc-Arg(Mtr)H (1.5 g, 3.29 mmol) in THF (5 mL) was added. The mixture was stirred for 45 minutes. 1HCl (30 mL) was added. The product was extracted into ethyl acetate (50 mL), washed with saturated aqueous NaHCO$_3$ (30 mL), dried over MgSO$_4$, filtered, and evaporated to dryness. The residue was precipitated from CH$_2$Cl$_2$/ether/hexane to give 1.55 g (89%) of product, ethyl (S)-(E)-4-tert-butoxycarbonylamino-7-(4methoxy-2,3, 6trimethylbenzenesulfonylguanidino)-2-heptenoate.

This material was treated immediately with 5 mL of 30% hydrogen bromide in acetic acid for 5 hours. The orange oil was dissolved in methanol (8 mL), and poured into ether (300 mL). The oil that separated was dried in vacuo, giving 0.81 g (67%) of ethyl (S)-4-amino-7-guanidino-2-heptenoate dihydrobromide (ArgVEOEt.2HBr) as an orange foamy solid.

To a solution of Mu-PheOH (0.55 g, 1.98 mmol) in DMF (8 mL) at −10° C. were added 4-methylmorpholine (0.217 mL, 1.98 mmol), followed by isobutyl chloroformate (0.256 mL, 198 mmol). The mixed anhydride was stirred for 15 minutes, whereupon a solution of ArgVEOEt.2HBr (0.81 g, 1.98 mmol) in DMF (2 mL) was added, followed by 4-methylmorpholine (0.217 mL, 1.98 mmol). The mixture was stirred for 1 hour. The solvent was removed in vacuo. Butanol (30 mL) was added. The solution was washed with saturated aqueous NaHCO$_3$ (15 mL), filtered through glass wool, and the solvent was removed under reduced pressure. The residue was dissolved in methanol (5 mL) and filtered through a pad of Celite. The filtrate was poured into 1:1 ether/ethyl acetate (300 mL), filtered, and the solids were dried overnight, giving 0.77 g of product (68%: 41% from Boc-Arg(Mtr)H).

Melting points for this and subsequent examples were recorded on a Mel-Temp II. The melting point of the ArgVEOEt.HBr was 138–142° C. (dec.).

The NMR results, as defined in Example 1, were as follows. NMR (DMSO-d$^6$): 1.2 (3H, t, J=6 Hz, CH$_3$); 1.4–1.65 (4H, m, CH$_2$CH$_2$CH$_2$-guanidinium); 2.82–2.95 (2H, m, CH$_2$Ph); 3.0–3.15 (2H, m*, CH$_2$-guanidinium); 3.1 (4H, m, 2×CH$_2$N (morpholine)); 3.45 (4H, m, 2×CH$_2$O (morpholine)); 4.1 (2H, q, J=6 Hz, CH$_2$ (ester)); 4.18 (1H, m, CHNH); 4.43 (1H, m, CHNH); 5.75 (1H, d, J=15 Hz, trans COCH=CH); 6.67 (1H, d, J=7 Hz, NHCH); 6.75 (1H, dd, J=5,15 Hz, trans CH=CHCO); 7.1–7.3 (9H, m*, aromatic and guanidinium); 7.81 (1H, m, NH); 8.15 (1H, d, J=7 Hz, NHCH).

Example 3

Additional Cysteine Protease Inhibitors with Vinylogous Ethyl Esters (S)-(E)-Ethyl 8-(benzyloxycarbonyl)amino-4-(4-morpholinecarbonylphenylalanyl)amino-2-octenoate and (S)-(E)-Ethyl 8-amino-4-(4-morpholinecarbonylphenylalanyl)amino-2-octenoate hydrobromide were made as per Examples 1 and 2, and tested against a variety of cysteine proteases as shown below.

Example 4

Synthesis of a Cysteine Protease Inhibitor with a Vinylogous Sulfone with Methyl terminus Synthesis of (S)-(E)-5-(4-morpholinecarbonyl-phenylalanyl)amino-7-phenyl-2-thia-3-heptene 2,2-dioxide, abbreviated Mu-Phe-HphVSMe, was as follows. Diethyl (methylsulfonylmethyl) phosphonate (MSMP) was prepared by m-chloroperbenzoic acid oxidation of commercially available diethyl(methylthiomethyl) phosphonate. To a solution of MSMP (1.5 g, 6.51 mmol) in THF (25 mL) at 0° C. was added sodium hydride (0.26 g of a 60% mineral oil dispersion). The mixture was stirred for 15 minutes. A solution of Boc-HphH (1.72 g, 6.51 mmol) in THF (10 mL) was added. The mixture was stirred for 1 hour. 1M HCl (30 mL) was added. The product was extracted into ethyl acetate (50 mL), washed with saturated aqueous NaHCO$_3$ (30 mL), dried over MgSO$_4$, filtered, and the solvents were removed under reduced pressure, giving 1.90 g of a white solid.

This material was dissolved in CH$_2$Cl$_2$ (5 mL), and was treated with 10 mL of a 4.0 M solution of HCl in dioxane. The mixture was stirred for 2 hours. Ether (200 mL) was added to the white suspension. The mixture was stirred vigorously for 5 minutes, filtered, and pumped dry to give 1.40 g of (S)-(E)-5-amino-7-phenyl-2-thia-3-heptene 2,2-dioxide (HCl.HphVSMe).

To a solution of Mu-PheOH (0.71 g, 2.54 mmol) in THF (10 mL) at −10° C. were added 4-methylmorpholine (0.28 mL, 2.54 mmol) and isobutyl chloroformate (0.329 mL, 2.54 mmol). The mixed anhydride was stirred for 10 minutes, whereupon a solution of HCl.HphVSMe (0.70 g, 2.54 mmol) in DMF (2 mL) was added, followed by 4-methylmorpholine (0.28 mL, 2.54 mmol). The mixture was stirred for 45 minutes. 1M HCl (30 mL) was added. The product was extracted into ethyl acetate (50 mL), washed with saturated aqueous NaHCO3 (30 mL), dried over MgSO4, filtered, and evaporated to dryness. The residue was crystallized from CH$_2$Cl$_2$/ether/hexane (1:10:5) to give a total of 0.57 g (45% yield, 35% from Boc-HphH).

The retention factor on TLC: (10% MeOH/CH2Cl2) was 0.69. $^1$H NMR (CDCl3): 1.7–1.97 (2H, m, CH$_2$CH$_2$Ph); 2.31 (2H, m, CH$_2$CH$_2$Ph); 2.86 (3H, s, CH$_3$SO$_2$); 3.08 (2H, br. d, PhCH$_2$); 3.48 (4H, m, 2×CH$_2$N (morpholine)); 3.62 (4H, m, 2×CH$_2$O, (morpholine)); 4.52 (1H, q, J=7 Hz, CHNH (Phe)); 4.61 (1H, m, C$_H$NH); 4.95 (1H, d, J=7 Hz, NHCH); 6.10 (1H, dd, J=2,15 Hz, trans SO$_2$CH=CH); 6.43 (1H, d, J=7 Hz, NHCH); 6.70 (1H, dd, J=5,15 Hz, trans CH=CHSO$_2$); 7.08–7.38 (10H, m, aromatic.)

Indication of approximately an 8:1 ratio of (S) to (R) epimers was evidenced by the presence in the spectrum of Mu-Phe-HphVSMe of a doublet of doublets at 6.95 ppm (J=5,15 Hz), along with a singlet at 2.87 ppm. This phenomenon is possibly due to isomerically impure commercial material.

Example 5

Synthesis of additional Cysteine Protease Inhibitors with Vinylogous Sulfones with Methyl Termini (S)-(E)-3-(4-morpholinecarbonylphenylalanyl)amino-1-methylsulfonyl-1-butene, (S)-(E)-3-(4-morpholinecarbonylphenylalanyl)amino-1-methylsulfonyl-4-phenyl-1-butene, and (S)-(E)-3-(tert-butoxycarbonylalanyl)amino-1-methylsulfonyl-4-phenyl-1-butene were made as above, and tested against various cysteine proteases as shown below.

Example 6

Synthesis of a Cysteine Protease Inhibitor with a Vinylogous Sulfone with Phenyl terminus Synthesis of (S)-(E)-3-tert-butoxycarbonylamino-4-methyl-1-phenylsulfonyl-1-pentene, abbreviated Boc- ValVSPh, was as follows. To a solution of diethyl phenyl-sulfonylmethylenephosphonate (PSMP), (1.40 g, 4.79 mmol, prepared by treatment of the lithium anion of methyl phenyl sulfone with diethyl chlorophosphate) in THF (20 mL) at −20° C. was added sodium hydride (0.192 g of a 60% mineral oil dispersion, 4.79 mmol). The mixture was warmed to 0° C. over 20 minutes. Boc-valinal (0.876 g, 4.35 mmol) prepared according to the method of Fehrentz and Castro, supra), was added as a solution in THF (5 mL). The mixture was stirred for 30 minutes. 1M HCl (30 mL) was added. The product was extracted with ethyl acetate (50 mL), washed with saturated aqueous NaHCO$_3$ (30 mL), brine (20 mL), dried over MgSO$_4$, filtered, and evaporated to dryness to afford the product in quantitative yield.

The melting point of the Boc-ValVSPh was 101–103° C.

TLC analysis (30% ethyl acetate/pet. ether) showed a retention factor of 0.4.

$^1$H NMR (CDCl$_3$): 0.92 (6H, 2×d, J=6 Hz, isopropyl CH$_3$'s of valine residue); 1.39 (9H, s, t-C$_4$H$_9$); 1.87 (1H, m, CH(CH$_3$)$_2$); 4.11 (1H, m, CHNH); 4.5 (1H, br d, NHCH); 6.41 (1H, d, J=15 Hz, trans SO$_2$CH=CH); 6.87 (1H, dd, J=5,15 Hz, trans C$_H$=CHSO$_2$); 7.48–7.87 (5H, m, aromatic).

Example 7

Synthesis of a Cysteine Protease Inhibitor with a Vinylogous Sulfone with Phenyl Terminus Synthesis of (S)-(E)-3-(4-morpholinecarbonyl-phenylalanyl)amino-5-phenyl-1-phenylsulfonyl-1-pentene, abbreviated Mu-Phe-HphVSPh, was as follows. To a solution of PSMP (1.94 g, 6.64 mmol) in THF (30 mL) at 0° C. was added sodium hydride (0.27 g of a 60% mineral oil dispersion, 6.64 mmol). After 15 minutes, a solution of Boc-HphH (1.59 g, 8.94 mmol) in THF (5 mL) was added. The mixture was stirred for 30 minutes. 1M HCl (20 mL) was added. The product (Boc-HphVSPh) was extracted into ethyl acetate (80 mL), washed with saturated aqueous NaHCO$_3$ (30 mL), dried over MgSO$_4$, filtered, and the solvents were removed under reduced pressure to give a pale yellow oil.

This material was dissolved in CH$_2$Cl$_2$ (5 mL) and treated with a 4.0 M solution of HCl in dioxane (15 mL) for 30 minutes. The solvents were removed under reduced pressure, the residue was dissolved in methanol (5 mL) and the solution was poured into hexane/ether (1:1; 350 mL). The precipitate was filtered and pumped dry to give 0.77 g (38% from Boc-HphH) of (S)-(E)-3-amino-5-phenyl-1-phenylsulfonyl-1-pentene hydrochloride (HCl.HphVSPh).

To a solution of Mu-PheOH (0.63 g, 2.28 mmol) in THF (10 mL) at −10° C. was added 4-methylmorpholine (0.251 mL, 2.28 mmol), followed by isobutyl chloroformate (0.295 mL, 2.28 mmol). The mixed anhydride was stirred for 10 minutes, whereupon a solution of HCl.HphVSPh (0.77 g, 2.28 mmol) in DMF (2 mL) was added, followed by 4-methylmorpholine (0.251 mL, 2.28 mmol). The mixture was stirred for 1 hour. 1M HCl (20 mL) was added. The product was extracted into ethyl acetate (50 mL), washed with saturated aqueous NaHCO$_3$ (30 mL), dried over MgSO$_4$, filtered, and evaporated to dryness, giving 0.80 g (62%) yield of product as an amorphous solid.

The melting point of the product was 85–87° C.

$^1$H NMR (CDCl$_3$): 1.68–1.93 (2H, m, CH$_2$CH$_2$Ph); 2.58 (2H, m, CH$_2$CH$_2$Ph); 3.03 (2H, d, J=7 Hz, PhCH$_2$CH); 3.27 (4H, m, 2×CH$_2$N (morpholine)); 3.62 (4H, m, 2×CH$_2$O (morpholine)); 4.44 (1H, q, J=7 Hz, CHCH$_2$Ph); 4.62 (1H, m, CHCH=CH); 4.93 (1H, d, J=7 Hz, NHCH); 6.08 (1H, dd, J=2,15 Hz, trans SO$_2$CH=CH); 6.23 (1H, d, J=7 Hz, NHCH); 6.77 (1H, dd, J=5,15 Hz, trans CH=CHSO$_2$); 7.07–7.87 (15H, m, aromatic). Mass Spectroscopy (FAB, high resolution): calculated for C$_{31}$H$_{35}$N$_3$O$_5$S, (m+H)= 562.2376, found 562.2362.

Example 8

Synthesis of Additional Cysteine Protease Inhibitors with Vinylogous Sulfones with Phenyl Termini The following cysteine protease inhibitors were made as per examples 6 and 7 and tested as shown below: (S)-(E)-3-(4-morpholinecarbonylphenylalanyl) amino-6-guanidino-1-phenylsulfonyl-1-hexene hydrobromide, (S)-(E)-3-(4-morpholinecarbonylphenylalanyl)amino-5-phenyl-1-phenylsulfonyl-1-pentene, (S)-(E)-3-glycylamino-4-phenyl-1-phenylsulfonyl-1-butene hydrochloride, (S)-(E)-7-(benzyloxycarbonyl)amino-3-(4-morpholinecarbonylphenylalanyl)-amino-1-phenylsulfonyl-1-heptene, (S)-(E)-7-amino-3-(4-morpholinecarbonylphenylalanyl)amino-1-phenylsulfonyl-1-heptene hydrobromide, (S)-(E)-3-(4-morpholinecarbonylphenylalanyl)amino-4-methyl-1-phenylsulfonyl-1-butene, (S)-(E)-3-amino-4-phenyl-1-phenylsulfonyl-1-butene hydrochloride, (S)-(E)-3-(4-morpholinecarbonylvalyl)amino-4-phenyl-1-phenylsulfonyl-1-butene, (S)-(E)-3-(4-morpholinecarbonylarginyl)amino-6 -guanidino-1-phenylsulfonyl-1-hexene dihydrobromide, (S)-(E)-3-(4-morpholinecarbonylphenylalanyl)amino-4-benzyloxy-1-phenylsulfonyl-1-butene, (S)-(E)-3-(4-morpholinecarbonylphenylalanyl)amino-7-benzoylamino-1-phenylsulfonyl-1-heptene, (R)-(E)-3-(4-morpholinecarbonylphenylalanyl)amino-5-phenyl-1-phenylsulfonyl-1-pentene, (S)-(E)-3-[4-morpholinecarbonyl-(3,5-diiodotyrosyl)]-amino-5-phenyl-1-phenylsulfonyl-1-pentene, (S)-(E)-3-[4-tert-butoxycarbonyl-(3,5-diiodotyrosyl)]-amino-5-phenyl-1-phenylsulfonyl-1-pentene, (S,S)-(E)-3-[4-morpholinecarbonyl-(1,2,3,4-tetrahydro-3-isoquinolinecarbonyl)]amino-5-phenyl-1-phenylsulfonyl-1-pentene, (S,S)-(E)-3-[tert-butoxycarbonyl-(1,2,3,4-tetrahydro-3-isoquinolinecarbonyl)]-amino-5-phenyl-1-phenylsulfonyl-1-pentene, (S)-(E)-3-(4-morpholinecarbonylleucylleucyl) amino-4-(4-hydroxyphenyl)-1-phenylsulfonyl-1-butene, (S)-(E)-3-amino-5-phenyl-1-phenylsulfonyl-1-pentene hydrochloride, (S)-(E)-3-[(4-morpholinecarbonyl-(R,S)-α-methylphenylalanyl]amino-5-phenyl-1-phenylsulfonyl-1-pentene, (S)-(E)-3-(benzyloxycarbonylleucylleucyl)amino-4-(4-hydroxyphenyl)-1-phenylsulfonyl-1-butene, (S)-(E)-3-(4-morpholinecarbonyltyrosyl)amino-5-phenyl-1-phenylsulfonyl-1-pentene, (S)-(E)-3-(tert-butoxycarbonyl-2-naphthylalanyl)amino-5-phenyl-1-phenylsulfonyl-1-pentene, (S)-(E)-3-(4-morpholinecarbonyl-2-naphthylalanyl)amino-5-phenyl-1-phenylsulfonyl-1-pentene, (S)-(E)-3-(4-morpholinecarbonyl-4-biphenylalanyl)amino-5-phenyl-1-phenylsulfonyl-1-pentene, (S)-(E)-3-(4-morpholinecarbonylphenylalanyl) amino-1-phenylsulfonyl-1-heptene, (S)-(E)-3-(4-morpholinecarbonylphenylalanyl)amino-1-phenylsulfonyl-6-thia-1-heptene, (S)-(E)-3-(4-morpholinecarbonylphenylalanyl)amino-5-methylsulfonyl-1-phenylsulfonyl-1-pentene, (S)-(E)-3-(acetylleucylleucyl) amino-1-phenylsulfonyl-1-heptene, (S)-(E)-3-(acetylleucylleucyl)amino-1-phenylsulfonyl-6-thia-1-heptene, (S)-(E)-3-(acetylleucylleucyl)amino-5- methylsulfonyl-1-phenylsulfonyl-1-pentene, (S)-(E)-3-(carbomethoxypropionylphenylalanyl)amino-5-phenyl-1-phenylsulfonyl-1-pentene, (S)-7-(benzyloxycarbonyl)amino-3-(4-morpholinecarbonylphenylalanyl)-amino-1-fluoro-1-phenylsulfonyl-1-heptene, (S)-(E)-3-(acetylleucylleucyl)amino-4-(4-hydroxyphenyl)-1-phenylsulfonyl-1-butene, (S)-(E)-3-(dimethylsulfamoylphenylalanyl)amino-5-phenyl-1-phenylsulfonyl-1-pentene, (S)-(E)-3-(4-morpholinecarbonylphenylalanyl)amino-1-(4-bromophenylsulfonyl)-5-phenyl-1-pentene, (S)-(E)-3-(4-morpholinecarbonylphenylalanyl)amino-1-(2-napthylsulfonyl)-5-phenyl-1-pentene, (S)-(E)-3-(4-morpholinecarbonyl-2-naphthylalanyl)amino-1-(2-napthylsulfonyl)-5-phenyl-1-pentene, (S)-(E)-3-(4-morpholinecarbonyl)amino-5-phenyl-1-phenylsulfonyl-1-pentene, (S)-(E)-3-(4-morpholinecarbonylphenylalanyl)amino-1-methylsulfonyl-1-butene, (S)-(E)-3-(4-morpholinecarbonylphenylalanyl)amino-1-methylsulfonyl-4-phenyl-1-butene, and (S)-(E)-3-(tert-2butoxycarbonylalanyl)amino-1-methylsulfonyl-4-phenyl-1-butene.

Example 9

Synthesis of a Cysteine Protease Inhibitor with a Vinylogous Carboxlate

Synthesis of (S)-(E)-4-(4-morpholinecarbonyl-phenylalanyl)amino-6-phenyl-2-hexenoic acid, abbreviated Mu-Phe-HphVA, was as follows. To a solution of Mu-Phe-VEOEt (see Example 1; 1.96 g, 4.15 mmol) in ethanol (7 mL) was added 1M NaOH (9.5 mL) over 3 hours. The solvents were evaporated. Water (30 mL) was added. The solution was washed with ethyl acetate (30 mL), acidified with 1M HCl (15 mL), extracted with ethyl acetate (60 mL), dried over MgSO$_4$, filtered, and evaporated to dryness, giving a slightly off-white foam. Yield=1.63 g (89%).

The melting point was determined to be 91–93° C. TLC analysis in 10% CH$_3$OH/CH$_2$Cl$_2$ showed a retention factor of 0–0.3 (streak, staining yellow with bromocresol green, indicating presence of acidic functionality). The material was derivatized with HCl.Leu-ProOCH$_3$ (Example 8, infra, to demonstrate retention of double bond configuration; see NMR data described therein.

Example 10

Synthesis of an Additional Cysteine Protease Inhibitor with a Vinylogous Carboxylate (S)-(E)-Benzyl 4-(4-morpholinecarbonylphenylalanyl)amino-6-phenyl-2-hexenamide was synthesized using the techniques of example 9 and tested as shown below.

Example II

Synthesis of a Cysteine Protease Inhibitor with a Vinylogous Phosphonate

Synthesis of diethyl (S)-(E)-4-(4-morpholinecarbonylphenylalanyl)amino-6-phenyl-2-hexenephosphonate, abbreviated Mu-Phe-HphVPEt, was as follows. To a solution of tetraethyl methylenediphosphonate (2.00 g, 6.94 mmol) in THF (30 mL) was added sodium hydride (0.278 g of a 60% mineral oil dispersion, 6.94 mmol). The mixture effervesced rapidly and then clarified. After 5 minutes, a solution of Boc-HphH (1.83 g, 6.94 mmol) in THF (5 mL) was added. The mixture was stirred for 1 hour. 1M HCl (20 mL) was added. The product was extracted into ethyl acetate (50 mL), washed with saturated aqueous NaHCO$_3$ (20 mL), brine (10 mL), dried over MgSO$_4$, filtered, and evaporated to dryness, giving 2.46 g (89%) of diethyl (S)-(E)-4-tert-butoxycarbonylamino-6-phenyl-2-hexenephosphonate (Boc-HphVPEt) as a single spot on TLC (Rf=0.58, 10% CH$_3$OH/CH$_2$Cl$_2$). This material was used without further purification.

To a solution of Boc-Hph-VPEt (2.46 g, 6.19 mmol) in CH$_2$Cl$_2$ (3 mL) was added 10 mL of a 4.0 M solution of HCl in dioxane. The mixture was stirred at room temperature for 1.5 hours. The solvents were removed under reduced pressure and the residue was dissolved in methanol (10 mL). The solution was poured into ether (400 mL). The precipitate was collected on a Buchner funnel, washed with ether (2×20 mL), and was pumped dry to give 1.25 g (60%) of product, diethyl (S)-(E)-4-amino-6-phenyl-2-hexenephosphonate hydrochloride (HCl.HphVPEt).

To a solution of Mu-PheOH (1.04 g, 3.74 mmol) in THF (15 mL) at −10° C. was added 4-methylmorpholine (0.412 mL. 3.74 mmol), followed by isobutyl chloroformate (0.486 mL, 3.74 mmol). The mixed anhydride was stirred for 5 minutes, whereupon a solution of HCl.HphVPEt (1.25 g, 3.74 mmol) in DMF (5 mL) was added, followed by 4-methylmorpholine (0.412 mL, 3.74 mmol). The mixture was stirred for 1 hour. Ethyl acetate (50 mL) was added, The solution was washed with 1M HCl (25 mL), saturated aqueous NaHCO$_3$ (25 mL), and brine (10 mL), dried over MgSO$_4$, filtered, and evaporated to dryness. The product, upon treatment with CH$_2$Cl$_2$/ether/hexane (315 mL in a 15:200:100 ratio) formed an oil that solidified on drying in vacuo to give 1.44 g (69%) of the final product The melting point of the product was determined to be 53–55° C.

TLC analysis (10% CH$_3$OH/CH$_2$Cl$_2$) showed a retention factor of 0.48.

$^1$H NMR (CDCl$_3$): 1.35 (6H, 2×t, J=7 Hz, 2×CH$_3$CH$_1$OP); 1.68–1.87 (2H, m, CH$_2$CH$_2$Ph); 2.58 (2H, m, CH$_2$CH$_2$Ph); 3.08 (2H, d, J=7 Hz, CH$_2$Ph); 3.28 (4H, m, 2×CH$_2$N (morpholine)); 3.62 (4H, m, 2×CH$_2$O (morpholine)); 4.0–4.13 (4H, 2×dq, J=3,7 Hz, 2×CH$_3$CH$_2$OP, long-range H—C—O—P coupling responsible for splitting of quartet); 4.53 (1H, q*, J=7 Hz, CHNHC=O); 4.56 (1H, m, CHCH=CH); 5.02 (1H, d, J=7 Hz, NHCH); 5.50 (1H, ddd, J=2,15,17 Hz, P—CH=CH—CH); 6.34 (1H, d, J=7 Hz, NHCH); 6.58 (1H, ddd, 5,15,20 Hz, CH=CH—P); 7.08–7.34 (10H, m, aromatic).

Mass spectroscopy (FAB, high resolution): calculated for C$_{29}$H$_{40}$N$_3$O$_6$P, (m+H)=558.2733, found 558.2775.

Example 12

Synthesis of a Cysteine Protease Inhibitor with A Vinylogous Amide

Synthesis of (S)-(E)-(N-leucylproline methyl ester)-4-(4-morpholinecarbonylphenyl-alanyl)amino-6-phenyl-2-hexenamide, abbreviated Mu-Phe-HphVAM-Leu-ProOMe, was as follows. Leucylproline methyl ester hydrochloride (HCl.Leu-Pro-OMe) was prepared by mixed anhydride coupling of Boc-leucine and proline methyl ester hydrochloride, followed by Hcl-mediated deprotection of the N-terminal Boc group. Mu-Phe-HphVA (from Example 6, 1.42 g, 3.21 mmol) was dissolved in THF (15 mL) and cooled to −10° C. To this solution was added 4-methylmorpholine (0.354 mL, 3.21 mmol), followed by isobutyl chloroformate (0.417 mL, 3.21 mmol). The mixed anhydride was stirred for 5 minutes, whereupon HCl.Leu-ProOMe (0.897 g, 3.21 mmol) was added. 4-methylmorpholine (0.354 mL, 3.21 mmol) was added. The mixture was stirred for 4 hours. 1M HCl (20 mL) was added. The product was extracted into ethyl acetate (50 mL), washed with saturated aqueous $NaHCO_3$ (20 mL), brina (20 mL), dried over $MgSO_4$, filtered, and evaporated to dryness. The residue was dissolved in $CH_2Cl_2$ (5 mL) and was poured into 1:1 ether/pet ether (150 mL). The precipitate was collected on a Buchner funnel and pumped dry to give 1.42 g (64%) of a white solid.

The melting point of the product was determined to be 97–100° C.

TLC analysis (10% $CH_3OH/CH_2Cl_2$) showed a retention factor of 0.47.

$^1$H NMR ($CDCl_3$): 0.93 (6H, 2×d, J=7 Hz, 2×$CH_3$ (Leu)); 1.67–2.25 (9H, m $CH(CH_3)_2$, $CH_2$ (Leu), 2×$CH_2$ (Pro), $CH_2CH_2Ph$); 2.54 (1H, br t, $PhCH_2CH_2$); 3.04 (2H, m, CH2Ph); 3.28 (4H, m, 2×$CH_2N$ (morpholine)); 3.5–3.8 (6H, m*, 2×$CH_2O$ (morpholine), $CH_2N$ (Pro)); 3.7 (3H, s, $OCH_3$); 4.42–4.52 (2H, m, 2×CHNH); 4.89 (1H, m, CHNH); 5.11 (1H, d, J=7 Hz, NHCH); 5.43 (1H, dd, J=2,15 Hz, trans NHCOCH=CH); 6.03 (1H, d, J=7 Hz, NHCH); 6.25 (1H, d, J=7 Hz, NHCH); 6.55 (1H, dd, J=6,15 Hz, trans CH=CHCONH); 7.03=7.36 (10H, m, aromatic).

Example 13

Synthesis of a Cysteine Protease Inhibitor with a Vinylogous Amide

Synthesis of (S)-(E)-(N-phenylalanine)-4-(4-morpholinecarbonylphenylalanyl)amino-6-phenyl-2-hexenamide, abbreviated Mu-Phe-HphVAM-PheOH, proceeded as follows. Boc-PheOH (5.00 g, 18.85 mmol), trimethylsilylethanol (2.70 mL, 18.85 mmol), and 4-dimethylaminopyridine (0.23 g, 1.89 mmol) were dissolved in $CH_2Cl_2$ (70 mL). A solution of dicylcohexylcarbodiimide (DCC) (3.89 g, 18.85 mmol) in $CH_2Cl_2$ (20 mL) was added. The mixture was stirred for 1 hour. The suspension was filtered and the solvent was removed under reduced pressure. The residue was dissolved in ether (200 mL), washed with 50 mL each of 1M HCl, saturated aqueous $NaHCO_3$, and brine, dried over $MgSO_4$, filtered, and evaporated to dryness. The residue was dissolved in hot hexane, filtered to remove any residual dicyclohexylurea (DCU) by-product, and evaporated to give 6.7 g (98% yield) of a colorless oil, tert-butoxycarbonylphenylalanine, silylethyl ester (Boc-PheOSET). TLC of the Boc-PheOSET (30% ethyl acetate/hexane) showed a Rf of 0.65.

30 mL of a 4.0 M solution of HCl in dioxane was added to the Boc-PheOSET from the previous step. The mixture was stirred for 90 minutes. The solvents were evaporated, giving a waxy solid, phenylalanine silylethyl ester hydrochloride (HCl.PheOSET).

$^1$H NMR ($CDCl_3$): 0.02 (9H, s, $(CH_3)_3Si$); 0.89 (2H, m, $CH_2Si$); 3.32–2.51 (2H, 2×dd, J=7,14 Hz, J=5,14 Hz, $CH_2Ph$); 4.18 (2H, m, $CH_2CH_2Si$); 4.37 (1H, br q, $CHNH_3^+$); 7.23–7.37 (5H, m, aromatic); 8.82 (3H, br s, $NH_3^+$).

Diethyl phosphonoacetic acid (DEPA) was prepared in quantitative yield by saponification of triethyl phosphonoacetate in ethanol, in the presence of 1.1 equivalents of 1M NaOH. To a solution of DEPA (1.62 g, 8.28 mmol), HCl.PheOSET (2.5 g, 8.28 mmol), and triethylamine (0.676 mL, 8.28 mmol) in $CH_2Cl_2$ (30 mL) was added a solution of DCC (1.71 g, 8.28 mmol) in $CH_2Cl_2$ (10 mL). The mixture was stirred at room temperature for 16 hours. The white suspension was filtered, the solvent was removed under reduced pressure, and the residue was dissolved in ethyl acetate (100 mL). The solution was washed with 1M HCl (50 mL), saturated aqueous $NaHCO_3$ (50 mL), brine (25 mL), dried over $MgSO_4$, filtered, and evaporated to dryness. The residue was dissolved in hot pet ether and filtered to remove any remaining DCU, and was evaporated to give a colorless oil, diethyl phosphonoacetylphenylalanine, silylethyl ester (EPAc-PheOSET) weighing 3.56 g (97% from Boc-PheOSET). TLC analysis (20% ethyl acetate/$CH_2Cl_2$) showed a retention factor of 0.22.

To a solution of EPAc-PheOSEt (1.19 g, 2.68 mmol) in THF (10 mL) at 0° C. was added sodium hydride (107 mg of a 60% mineral oil dispersion). The mixture was stirred for 15 minutes while being allowed to warm to room temperature, whereupon a solution of Boc-HphH (0.707 g, 2.68 mmol) in THF (5 mL) was added. The mixture was stirred for 20 minutes. 1M HCl (15 mL) was added. The product was extracted into ethyl acetate (40 mL), washed with saturated aqueous $NaHCO_3$ (15 mL), brine (15 mL), dried over $MgSO_4$, filtered, and evaporated to dryness. The product, (S)-(E)-(N-phenylalanine silylethyl ester)-4-tert-butoxycarbonylamino-6-phenyl-2-hexenamide (Boc-HphVAM-PheOSET) was crystallized from $CH_2Cl_2$ and 1:1 ether/hexane. Yield=0.78 g (53%). TLC analysis (30% ethyl acetate/hexane) showed a retention factor of 0.35.

To a solution of Boc-HphVAM-PheOSET (1.80 g, 3.25 mmol) in $CH_2Cl_2$ (1 mL) were added 8 mL of a 4.0 M solution of HCl in dioxane. The mixture was stirred for 60 minutes, whereupon the solvents were removed under reduced pressure. The residue was pumped to a pale yellow foamy solid, (S)-(E)-(N-phenylalanine silylethyl ester)-4-amino-6-phenyl-2-hexenamide (HCl.HphVAM-PheOSET). Yield=1.40 g (88%).

To a solution of Mu-PheOH (0.797 g, 2.86 mmol) in THF (10 mL) at -10° C. was added 4-methylmorpholine (0.315 mL, 2.86 mmol), followed by isobutyl chloroformate (0.371 mL, 2.86 mmol). The mixed anhydride was stirred for 5 minutes, whereupon a solution of HCl.HphVAM-PheOSET (1.40 g, 2.86 mmol) in THF (5 mL) was added.

4-methylmorpholine (0.315 mL, 2.86 mmol) was added. The mixture was stirred for 75 minutes. Ethyl acetate (40 mL) was added. The mixture was washed with 1M HCl (15 mL), saturated aqueous $NaHCO_3$ (15 mL), brine (10 mL), dried over $MgSO_4$, filtered, and evaporated to dryness, giving 1.9 g (93%) of the product, (S)-(E)-(N-phenylalanine silylethyl ester)-4-(4-morpholinecarbonylphenylalanyl) amino-6-phenyl-2-hexenamide (Mu-Phe-HphVAM-PheOSET). TLC analysis (50% ethyl acetate/CH2Cl2) revealed a retention factor of 0.32.

To a solution of Mu-Phe-HphVAM-PheOSET (1.59 g, 2.23 mmol) in THF (10 mL) were added ~2 g of 3 Å molecular sieves, followed by 2.23 mL of a 1.0 M THF solution of tetrabutylammonium fluoride. The mixture was stirred at room temperature overnight. Ethyl acetate (50 mL) was added. The solution was filtered through Celite, washed with 1M HCl (20 mL), brine (20 mL) dried over $MgSO_4$, filtered, and evaporated to dryness. The residue was dissolved in $CH_2Cl_2$ (10 mL) and the solution was poured into ether (300 mL). The precipitate was collected on a Buchner funnel, washed with ether (2×20 mL), and pumped dry to give 0.84 g (61%) of Mu-Phe-HphVAM-PheOH as a white solid.

The melting point was determined to be 95–98° C.

TLC analysis (10% $CH_3OH/CH_2Cl_2$) showed a retention factor of 0.05–0.18 (yellow stain with bromocresol green indicating acidic functionality.)

Example 14

Synthesis of a Cysteine Protease Inhibitor with a Vinylogous Sulfone

Synthesis of (S)-(E)-3-tert-butoxycarbonylamino-4-tertbutoxycarbonyl-1-methylsulfonyl-1-butene, abbreviated herein as (Boc-Asp(Ot-Bu)VSMe, was as follows. The aldehpyde of Boc-Asp(Ot-Bu) was prepared in a slightly modified version of the manner of Fehrentz, supra, by the conversion to the $N_2O$-dimethyl amide in quantitative yield. Reduction with lithium aluminum hydride (0.5 mole equivalents) reduced the amide in the presence of the tertbutyl ester in 88% yield. Sodium hydride (0.633 g of a 60% mineral oil suspension, 16.58 mmol) was added to a solution of diethyl methylsulfonylmethylene phosphonate (3.5 g, 15.2 mmol) in THF (50 ml) at 0° C. The mixture was warmed to 25° C. over 60 minutes. Boc-AspH($\beta$-O-t-Bu) (3.78 g, 13.82 mmol) was added as a solution in THF (15 mls). The mixture was stirred for 60 minutes. 50 mls of 1 M HCl was added. The product was extracted with 100 mls of ethyl acetate, washed with 50 mls saturated aqueous $NaHCO_3$, 50 mls of brine, dired over $CaCl_2$, filtered, and evaporated to dryness. The residue was purified by column chromatography (30–60% ethyl acetate in hexane, gradient elution) to afford the product, (1.88 gm, 39%), that could be crystallized from ether and hexane.

TLC (30% ethyl acetate/hexane): $R_f=0.25$. $^1$H NMR ($CDCL_3$): 1.43 (18H, 2×s*, t-Bu $CH_3$'s); 2.55 (2H, 2×dd, J=16,7 Hz, $CH_2COOt$-Bu); 2.91 (3H, s, $CH_3$); 4.69 (1H, m, CHNH); 5.38 (1H, m, NHCH); 6.50 (1H, dd, J=15,2 Hz, trans $SO_2CH=CH$); 6.86 (1H, J=5, 15 Hz, trans $CH=CHSO_2$).

Example 15

Synthesis of a Cysteine Protease Inhibitor with a Vinylogous Sulfone

(S)-(E)-3-amino-4-tert-butoxycarbonyl-1-methylsulfonyl-1-butene, abbreviated TsOH.Asp(Ot-Bu)VSMe was synthesized as follows. A solution of anhydrous p-toluenesulfonic acid (0.95 g, 5.58 mmol) (commercially available as the hydrate from Aldrich) in 1 ml ether was added to a solution of Boc-Asp(Ot-Bu)VSME (0.41 g, 1.17 mmol) in 1:1 dichloromethane/ether (4 ml). The mixture was stirred at room temperature overnight. 15 ml of ether was added. The product, a precipitate, was filtered, washed with 20 mls ether, and dried in vacuo to give 0.49 g (99%) of the product. By using p-toluenesulfonic acid, the Boc group was selectively removed in the presence of the less labile tert-butyl ester.

Example 16

Synthesis of a Cysteine Protease Inhibitor with a Vinylogous Sulfone

Synthesis of (S)-(E)-3-tert-butoxycarbonylamino-4-tert-butoxycarbonyl-1-phenylsulfonyl-1-butene, abbreviated Boc-Asp(Ot-Bu)-VSPh was as follows. Sodium hydride (0.489 g of a 60% mineral oil dispersion, 12.23 mmol) was added to a solution of PMSP (3.58 g, 12.23 mmol) in 50 mL of THF at 0° C. The mixture was stirred for 15 minutes. A solution of Boc-AspH($\beta$-Ot-Bu), prepared as described above (3.04 gm, 11.12 mmol) in 10 mls THF was added. The mixture was stirred for 1 hour, whereupon 30 mls of 1 M HCl was added. The product was extracted with ethyl acetate (100 ml), and washed with 50 mls of saturated aqueous $NaHCO_3$, 30 mls brine, dired over $MgSO_4$. filtered, and evaporated to dryness. Chromatography on silica gel (20–30% ethyl acetate/hexane, gradient elution) afforded 2.07 g 45%) of the product.

TLC=$R_f$=0.31.

Example 17

Synthesis of a Cysteine Protease Inhibitor with a Vinylogous Sulfone

Synthesis of (S)-(E)-3-amino 4-tert-butoxycarbonyl-1-phenylsulfonyl-1-butene-p-toluenesulfonate, abbreviated TsOH.Asp(Ot-Bu)VSPh, was as follows. A solution of anhydrous p-toluenesulfonic acid (1.0 g, 5.87 mmol) in 2 mls ether was added to a solution of Boc-Asp(Ot-Bu)VSPh (0.72 g, 1.75 mmol) in 2 mls ether. The mixture was stirred at room temperature overnight, then diluted with ether (25 mls). The white precipitate, was filtered, washed with ether, and dried in vacuo to give 0.80 g (95%) of the product.

Example 18

Synthesis of a Cysteine Protease Inhibitor with a Vinylogous Sulfone

Synthesis of (S)-(E)-3-amino-4-hycroxylcarbonyl-1-phenylsulfonyl-1-butene-p-toluenesulfonate, abbreviated HCl.AspVSPh was as follows. To a solution of Boc-Asp (Ot-Bu)VSPh (0.32 g, 0.778 mmol) in 2 mls ether was added 2 mls of 4.0 M HCl in dioxane (Aldrich). The mixture was stirred at room temperature overnight. 50 mls ether was added. The supernatant was decanted, and the residue was precipitated from methanol/ether, filtered, and dried in vacuo to give 0.20 g (88%) of product. By using HCl, both Boc and t-butyl ester groups were thus removed in one reaction.

Example 19

Synthesis of a Cysteine Protease Inhibitor with a Vinylogous Sulfone

Synthesis of (E)-3-acetyltyrosylvalylalanylamino-4-tert-butoxycarbonyl-1-phenylsulfonyl-1-butene, abbreviated Ac-Tyr-Val-Ala-Asp(Ot-Bu)VSPh, was as follows. Ac-Tyr-Val-AlaOH was prepared by standard peptide chemistry and coupled via mixed anhydride chemistry to TsOH.Asp(Ot-Bu)VSPh. The proton NMR spectrum (in $CD_8OD$) indicated a singlet at 1.18 ppm, integrating to 9H (t-butyl ester), a singlet at 1.75 integrating to 3H ($CH_8$ of acetate at N-terminus). Signals for the alkene group hydrogens are obscured by the aromatic Tyr protons at 6.6–7.2 ppm. The sulfonate aromatic protons (5H) absorbed at 7.6–7.9 ppm. The presence of the remaining residues in the NMR spectrum was clarified, in part, by removal of the t-butyl ester and spectroscopic analysis (infra).

Example 20

Synthesis of a Cysteine Protease Inhibitor with Vinylogous Sulfones

Synthesis of (E)-3-acetyltyrosylvalylalanylamino-4-hydroxycarbonyl-1-phenylsulfonyl-1-butene, abbreviated Ac-Tyr-Val-Ala-AspVSPh was as follows. Trifluoroacetic acid (0.5 mL) was added to Ac-Tyr-Val-Ala-Asp(O-t-Bu) VSPh (45 mg, 66.7 μmol). The mixture was permitted to stand at room temperature overnight. Ether (20 mL) was added. The precipitate was chilled to −20° C., filtered, washed with ether (10 mL), and dried in vacuo.

$^1$H NMR (CD$_3$OD/DMSO-d$^6$) indicated Ala and Val residues (0.8–1.2 ppm). The t-butyl group singlet at 1.18 ppm was no longer present. The presence of the vinyl sulfone group was indicated as a doublet (J=15 Hz) at 6.66 ppm, partially obscured by the doublet of the Tyr-aromatic residue, and as a doublet of doublets (J=15,5 Hz) at 6.91 ppm. The other Tyr-aromatic residue was seen as a doublet at 7.01 ppm. The sulfone aromatic protons (5H) were seen between 7.6 and 7.85 ppm.

The above examples demonstrate the feasibility of chemical manipulation of aspartic acid derivatives with the Asp side chain protected and deprotected. By using toluenesulfonic acid and trifluoroacetic acid at the appropriate stages of the synthesis, α,β-unsaturated sulfones [EWG'S] can be prepared as ICE inhibitors bearing Asp as the P$_1$ active site side chain moiety.

Example 21

Synthesis of a Cysteine Protease Inhibitor with a Vinylogous Sulfone

Synthesis of (S)-(E)-3-(4-morpholine-carbonylleucyl)amino-5-phenyl-1-phenylsulfonyl-1-pentene, abbreviated Mu-Leu-HphVSPh, was as follows. Preparation of Mu-Leu-Hph was achieved by coupling of HCl.HphVSPh (described in the preparation of Mu-Phe-HphVSPh) with leucine morpholine urea (Mu-LeuOH). Mu-LeuOH was prepared in two steps, namely by treating the leucine benzyl ester p-toluenesulfonate (Bachem) with 4-morpholine chloride (Aldrich) in the presence of triethylamine (Aldrich) to give Mu-LeuOBzl in 99% yield. Hydrogenolysis over 5% palladium/charcoal in ethyl acetate afforded the desired product in quantitative yield.

Example 22

Inhibition of Cathepsin B

Stock solutions of the various inhibitors (10 mM) were made in DMF; dilutions were made in the same solvent. Cathepsin B from human placenta, obtained from Sigma, was approximately 10 nM in the assay. The assay buffer contained 50 mM phosphate at pH 6.2, 2.5 mM dithiothreitol (DTT), and 2.5 mM ethylenediaminetetraacetic acid (EDTA). The substrate for cathepsin B was 50 μM Z-Arg-Arg-AMC (carbobenzyloxyarginylarginylaminomethylcoumarin). The assays were initiated at 25° C. by addition of enzyme to 2 mL of assay buffer containing the substrate and the various inhibitors (30–0.001 (μM). The increase in fluorescence at 460 nm with excitation at 380 nm was followed with time, and the assay was linear throughout the range observed. Inactivation of cathepsin B was indicated by a downward curve in the increase in fluorescence with time. In the absence of inhibitors, the enzymatic production of free AMC was linear throughout the time course of inactivation examined. Data points were collected over at least 3 half-times of inactivation, and in duplicate. The inhibition progress curves were analyzed using non-linear curve fitting software to compute the $k_{obs}$ values. Approximate second-order inactivation constants ($k_{obs}/$[I]) were calculated for all compounds. For selected inhibitors, plots of 1/[I] vs. 1/$k_{obs}$ yielded the true constants $k_{irr}$, $K_I$, and $k_{irr}/K_I$, and were corrected for the presence of substrate by dividing $K_I$(app.) by {1+[S]/K$_m$}.

The results are shown in Table 2.

TABLE 2

| Inhibitor | k/K$_I$ or k$_{obs}$/[I]* (M$^{-1}$ sec$^{-1}$) | k$_{irr}$, sec$^{-1}$ | K$_I$, μM |
|---|---|---|---|
| Mu-Tic-HphVSPh | 0 | — | — |
| Ac-Leu-Leu-NleVSPh | 0 | — | — |
| Ac-Leu-Leu-MetVSPh | 0 | — | — |
| Mu-DL-Fam-HphVSPh | 0 | — | binds |
| Boc-D(O-tBu)VSMe | 0 | — | — |
| Ac-Tyr-Tyr-Val-Ala-AspVSMe | 0 | — | — |
| Mu-Phe-HphVAMBzl | <100 | — | — |
| Mu-Arg-ARgVSPh.2HBr | 26- | 0.040 | 150 |
| Mu-Phe-AlaVSMe | 300 | 0.19 | ~1000 |
| Boc-Np-HphVSPh | 400* | — | — |
| Mu-Phe-HphVA | 450 | 0.038 | 85 |
| Mu-Phe-HphVAM.PheOH | 600* | — | — |
| Mu-Phe-LysVEOEt.HBr | 650* | — | — |
| Z-Leu-Leu-TyrVSPh | 730* | — | — |
| MeOSuc-Phe-HphVSPh | 870* | — | — |
| Boc-Tyr(I$_2$)-HphVSPh | 1400* | — | — |
| Mu-Phe-Met(O$_2$)VSPh | 1,600* | — | — |
| Mu-Phe-Lys(Z)fVSPh | 2,000* | — | — |
| Mu-Phe-OBSer-VSPh | 2900 | 0.14 | 47 |
| Mu-Phe-Hph-VSPh | 3100 | 0.061 | 19 |
| Mu-Leu-Hph-VSPh | 4250 | — | — |
| Mu-Phe-Lys(Z)VEOEt | 4100 | 0.13 | 32 |
| Mu-fPhe-HphVSPh | 4800* | — | — |
| Mu-Phe-HpHVSMe | 5100 | 0.13 | 26 |
| Mu-Phe-MetVSPh | 7,000 | — | — |
| Mu-Phe-Nle-VSPh | 7,600 | — | — |
| Mu-Phe-ArgVEOEt.HBr | 8200 | 0.16 | 19 |
| Mu-Phe-HphNS | 9,200 | 0.042 | 4.6 |
| Mu-Phe-HphVEOEt | 10,100 | 0.19 | 19 |
| Mu-Phe-LysVSPh.HBr (impure) | 11,700 | — | — |
| Mu-Phe-LysVSPh.HBr (pure) | 11,300* | — | — |
| Mu-Phe-ArgVSPh.HBr | 12,300 | 0.15 | 12 |
| Mu-Phe-HphVSPhBr | 15,500* | — | — |
| Mu-Phe-HphVSPh | 16,400 | 0.17 | 11 |
| Mu-Tyr-HphVSPh | 20,000* | — | — |
| Mu-Phe-HphNS | 21,300 | 0.60 | 28 |
| Mu-Phe-Hph-VSPh | 22,600 | 0.12 | 5.3 |
| Mu-Phe-Lys(Z)VSPh | 39,200 | 0.18 | 4.7 |
| Mu-Phe-HphVSNp | 63,700 | 0.087 | 1.4 |
| Mu-Np-HphVSPh | 86,000* | — | — |
| Mu-Np-HphVSNp | 184,000* | — | — |
| Mu-Tyr(I$_2$)-HphVSPh | 39,200 | 0.18 | 4.7 |

Example 23

Inhibition of Cathepsin L

Stock solutions of the various inhibitors (10 mM) were made in DMF; dilutions were made in the same solvent. Cathepsin L from rat liver, (see Mason et al., Biochem. J. 226:233–241 (1985)) was approximately 1 nM in the assay. The assay buffer contained 50 mM phosphate at pH 6:2, 2.5 mM dithiothreitol (DTT), and 2.5 mM ethylenediaminetetraacetic acid (EDTA). The substrate for cathepsin L was 5 μM Z-Phe-Arg-AMC (carbobenzyloxyphenylalanylarginylaminomethylcoumarin). The assays were initiated at 25° C. by addition of enzyme to 2 mL of assay buffer containing the substrate and the various inhibitors (30–0.001 μM). The increase in fluorescence at 460 nm with excitation at 380 nm was followed with time. Inactivation of cathepsin L was indicated by a downward curve in the increase in fluorescence with time. In the absence of inhibitors, the enzymatic production of free AMC was linear throughout the time course of inactivation examined. Data points were collected over at least 3 half-times of inactivation. The inhibition progress curves were analyzed using non-linear curve fitting software to compute the $k_{obs}$ values. Approximate second-order inactivation constants ($k_{obs}/[I]$) were calculated for all compounds. For selected inhibitors, plots of $1/[I]$ vs. $1/k_{obs}$ yielded the true constants $k_{irr}$, $K_I$, and $k_{irr/KI}$ and were corrected for the presence of substrate by dividing $K_I$(app.) by $(1+[S]/Km)$.

The results are shown in Table 3.

TABLE 3

| Inhibitor | k/$K_I$ or $k_{obs}/[I]$* ($M^{-1} sec^{-1}$) | $k_{irr}$, $sec^{-1}$ | $K_I$, $\mu M$ |
|---|---|---|---|
| Boc-Tic-HphVSPh | 0 | — | — |
| Mu-DL-Fam-HphVSPh | 0 | — | binds |
| Boc-Asp(O-tBu)VSMe | 0 | — | — |
| Ac-Tyr-Val-Ala-AspVSPh | 0 | — | — |
| Mu-Phe-PheVSMe | 100* | — | — |
| Mu-Phe-HphVAmBzl | 2800* | — | — |
| Mu-Phe-LysVEOEt.HBr | 3500 | 0.085 | 24.2 |
| Mu-Phe-HphVPEt | 4100 | 0.16 | 39 |
| Mu-Phe-HphVPhe | 8,600 | 0.032 | 3.7 |
| Mu-Phe-HpHVSMe | 8700* | — | — |
| Mu-Tic-HphVSPh | 12,600* | — | — |
| Mu-Phe-Lys(Z)VEOEt | 13,900 | 0.87 | 6.2 |
| Mu-Phe-D-HphVSPh | 4,500* | — | — |
| Mu-Leu-HphVSPh | 28,700* | — | — |
| Mu-Phe-Ser(OBzl)VSPh | 42,700 | 0.20 | 4.6 |
| MeOSuc-Phe-HphVSPh | 47,000* | — | — |
| Mu-Phe-HphVEOEt | 47,500 | 0.10 | 2.2 |
| Mu-Phe-ArgVEOEt.HBr | 56,900 | 0.18 | 3.1 |
| Mu-Phe-HphNS | 57,400 | — | — |
| Mu-Phe-ValVSPh | 74,000 | 0.19 | 2.6 |
| Boc-Tyr($I_2$)-HphVSPh | 105,000* | — | — |
| Mu-Phe-LysVSPh.HBr | 110,000 | 0.16 | 1.4 |
| Mu-Phe-Lys(Z)VSPh.HBr | 120,000 | 0.45 | 3.8 |
| Mu-Phe-NleVSPh | 188,000 | — | — |
| Mu-Tyr($I_2$)HphVSPh | 190,000* | — | — |
| Mu-Phe-LysVSPh.HBr | 220,000* | — | — |
| Mu-Phe-HphVSPh | 224,000 | 0.24 | 1.0 |
| Mu-Phe-HphVSPh (pure) | 260,000* | — | — |
| Mu-Phe-Lys(Bz)VSPh | 210,000* | — | — |
| Mu-Phe-Met($O_2$)VSPh | 250,000 | — | — |
| Mu-Phe-MetVSPh | 250,000 | — | — |
| Mu-Phe-Hph-VSPh | 201,000 | 0.23 | 1.1 |
| Mu-Phe-ArgVSPh.HBr | 349,000 | 0.67 | 1.9 |
| Mu-Leu-HphVSPh | 490,000 | 0.40 | 0.81 |
| Mu-Tyr-HphVSPh | 700,000* | — | — |
| Ac-Leu-Leu-MetVSPh | 880,000 | — | — |
| Ac-Leu-Leu-NleVSPh | 930,000 | — | — |
| Mu-Np-HphVSPh | 1,000,000* | — | — |
| Ac-Leu-Leu-Met($O_2$)VSPh | 1,500,000 | — | — |
| Boc-Np-HphVSPh | 1,600,000* | — | — |
| Mu-Np-HphVSNp | 9,200,000 | 0.14 | 0.018 |

Example 24

Inhibition of Cathepsin S

Stock solutions of the various inhibitors (10 mM) were made in DMF; dilutions were made in the same solvent. Cloned cathepsin S, (see Brömme et al., J. Biol. Chem. 268(&): 4832–4838 (1993)) was less than 1 nM in the assay. The assay buffer contained 100 mM phosphate at pH 6.5, 0.01% Triton, 2.5 mM dithiothreitol (DTT), and 2.5 mM ethylenediaminetetraacetic acid (EDTA). The substrate for cathepsin S was 10 $\mu M$ Z-Val-Val-Arg-AMC (carbobenzyloxyvalinylvalinylarginylaminomethylcoumarin). The assays were initiated at 25° C. by addition of enzyme to 2 mL of assay buffer containing the substrate and the various inhibitors (30–0.001 $\mu M$). The increase in fluorescence at 460 nm with excitation at 380 nm was followed with time. Inactivation of cathepsin S was indicated by a downward curve in the increase in fluorescence with time. In the absence of inhibitors, the enzymatic production of free AMC was linear throughout the time course of inactivation examined. Data points were collected over at least 3 half-times of inactivation. The inhibition progress curves were analyzed using non-linear curve fitting software to compute the $k_{obs}$ values. Approximate second-order inactivation constants ($k_{obs}/[I]$) were calculated for all compounds. For selected inhibitors, plots of $1/[I]$ vs. $1/k_{obs}$ yielded the true constants $k_{irr}$, $K_I$, and $k_{irr}/K_I$, and were corrected for the presence of substrate by dividing $K_I$(app.) by $\{1+[S]/Km\}$.

The results are shown in Table 4.

TABLE 4

| Inhibitor | k/$K_I$ or $k_{obs}/[I]$* ($M^{-1} sec^{-1}$) | $k_{irr}$, $sec^{-1}$ | $K_I$, $\mu M$ |
|---|---|---|---|
| Boc-Tic-HphVSPh | 0 | — | — |
| Mu-Phe-HphVAM-PheOH | 10,600* | — | — |
| Mu-Phe-Lys(Z)fVSPh | 10,700* | — | — |
| Mu-Phe-HphVAMBzl | 10,800* | — | — |
| Mu-Phe-HpHVPEt | 11,200 | 0.40 | 36 |
| Mu-Leu-Leu-TyrVSPh | 25,100* | — | — |
| Mu-Phe-Ala-VSMe | 26,000* | — | — |
| HCl.Phe-HphVSPh | 35,000* | — | — |
| Mu-DL-Fam-HphVSPh | 39,000 | 0.54 | 14 |
| Mu-Phe-HphNS | 40,300 | 0.033 | 0.81 |
| Mu-Phe-D-HphVSPh | 68,500* | — | — |
| Mu-Phe-Lys(Z)VEOEt | 100,000 | 0.13 | 1.3 |
| Ac-Leu-Leu-TyrVSPh | 100,000* | — | — |
| Mu-Phe-HphNS | 140,000 | 0.08 | 0.58 |
| Boc-Tyr($I_2$)HphVSPh | 210,000* | — | — |
| Z-Leu-Leu-TyrVSPh | 280,000* | — | — |
| Mu-Phe-ValVSPh | 290,000 | 0.039 | 0.13 |
| Mu-Tic-HphVSPh | 630,000* | — | — |
| MeOSuc-Phe-HphVSPh | 740,000* | — | — |
| DimSam-Phe-HphVSPh | 920,000* | — | — |
| Mu-Phe-HpHVSMe | 1,200,00 | 0.10 | 0.088 |
| Mu-Phe-Ser(OBzl)VSPh | 1,240,000 | 0.092 | 0.074 |
| Mu-Phe-ArgVSPh.HBr | 2,000,000 | 0.031 | 0.016 |
| Mu-Phe-Nle-VSPh | 2,300,000* | — | — |
| Mu-Phe-Lys(Bz)VSPh | 2,500,000* | — | — |
| Mu-Phe-Lys(Z)VSPh | 2,600,000 | 0.14 | 0.054 |
| Mu-Phe-Met($O_2$)VSPh | 2,800,000 | — | — |
| Z-Leu-PheVSPh | 3,000,000* | — | — |
| Mu-Phe-MetVSPh | 4,000,000 | — | — |
| Boc-Np-HphVSPh | 4,100,000* | — | — |
| Mu-Tyr-HphVSPh | 4,200,000* | — | — |
| Mu-Phe-HphVSNp | >5,400,000* | — | — |
| Mu-Phe-HphVSPh | 7,700,000 | 0.085 | 0.011 |
| Mu-Tyr($I_2$)HphVSPh | >7,300,000* | — | — |
| Mu-Phe-LysVSPh | 10,700,000* | — | — |
| Mu-fPhe-HphVSPh | 13,300,000* | — | — |
| Mu-Phe-Hph-VSPh | 6,500,000 | 0.15 | 0.023 |
| Mu-Np-HphVSNp | 56,000,000 | 0.10 | .0018 |
| Mu-Leu-HphVSPh | 26,300,000 | 0.16 | .00590 |

Example 25

Inhibition of Cruzain

Inhibition of cruzain, from *T. cruzi*, (see Eakin et at., J. Biol. Chem. 268(9): 6115–6118 (1993)) proceeded exactly as for cathepsin L, outlined above, using an enzyme concentration of 1 nM.

The results are shown in Table 5.

TABLE 5

| Inhibitor | k/$K_I$ or $k_{obs}$/[I]* ($M^{-1}$ sec$^{-1}$) | $k_{irr}$, sec$^{-1}$ | $K_I$, µM |
|---|---|---|---|
| Ac-Tyr-Val-Ala-AspVSPh | 0 | — | — |
| Mu-Tic-HphVSPh | 0 | — | — |
| Mu-Phe-AlaVSMe | 700* | — | — |
| Boc-ASp(O-tBu)VSMe | 800* | — | — |
| Mu-ARg-Arg-VSPh | 2,100* | — | — |
| Mu-Phe-Ser-(OBzl)VSPh | 12,800 | — | — |
| HCl.Phe-HphVSPh | 14,600* | — | — |
| Mu-DL-Fam-HphVSPh | 18,100* | — | — |
| Mu-Phe-HphVSMe | 22,000* | — | — |
| Mu-Phe-ValVSPh | 28,000* | — | — |
| Boc-Tic-HphVSPh | 30,000 | — | — |
| MeOSuc-Phe-HphVSPh | 34,000* | — | — |
| Mu-Phe-Lys(Z)VSPh | 44,500 | — | — |
| Z-Leu-Leu-TyrVSPh | 45,000* | — | — |
| Mu-Phe-HphVNS | 58,000* | — | — |
| Mu-Phe-Lys(Bz)VSPh | 60,000* | — | — |
| Mu-Phe-HphVAMBzl | 70,200* | — | — |
| Mu-Phe-NleVSPh | 77,000 | — | — |
| Mu-Phe-HphVEOEt | 80,400* | — | — |
| Mu-Phe-ArgVSPh | 91,400 | — | — |
| Acc-Leu-Leu-Met($O_2$)VSPh | 104,000 | — | — |
| Ac-Leu-Leu-MetVSPh | 110,000 | — | — |
| Mu-Phe-MetVSPh | 111,000 | — | — |
| Mu-Tyr($I_2$)HphVSPh | 114,000* | — | — |
| Ac-Leu-LeuNleVSPh | 133,000 | — | — |
| Mu-Phe-HphVSPh | 134,000 | 0.43 | 3.2 |
| Mu-Phe-LysVSPh | 149,000* | — | — |
| Mu-Phe-Met($O_2$)VSPh | 160,000 | — | — |
| Boc-Np-HphVSPh | 210,000* | — | — |
| Mu-Np-HphVSPh | 218,000 | — | — |
| Boc-Tyr($I_2$)HphVSPh | 280,000* | — | — |
| Mu-Tyr-HphVSPh | 297,000* | — | — |
| Mu-Phe-HphVSNp | 740,000 | 0.08- | 0.11 |
| Mu-Np-HphVSNA | 1,770,000 | 0.044 | 0.025 |
| Mu-Leu-HphVSPh | 213,000 | 0.11 | 0.52 |

Example 26

Stability of Selected Inhibitors Toward Glutathione

The inhibitors (5 mM) were incubated with glutathione (GSH) (0.3 mM) in phosphate buffer (50 mM) at pH=6.2 containing 15% DMF at 20° C. Periodically, 50 µL samples were added to 1 mL of buffer and treated with 10 µL of 30 mM Ellmans reagent and the absorbance measured at 412 nm.

After 24 hours there was no measurable reaction between Mu-Phe-HphVSMe or Mu-Phe-HphVPEt with GSH. The second order rate constant for the loss of GSH was measured to be $5.5 \times 10^{-4}$ $M^{-1}s^{-1}$ for Mu-Phe-LysVSPh. The vinyl ester analog Mu-Phe-ArgVEOEt was 10 times more reactive at $5.3 \times 10^{-3}$ $M^{-1}s^{-1}$. However, these compounds react at a minimum of $10^6$–$10^9$ times faster at the active sites of cysteine proteases than with GSH.

Example 27

Selectivity for Cysteine Proteases Versus Serine Proteases

Boc-Ala-PheVSPh (100 µM, in 100 mM TRIS buffer at pH=7.5) did not bind to chymotrypsin, nor did it inactivate chymotrypsin after 1 hour. The same was true for MeOSuc-Ala-Ala-Pro-ValVSPh (100 µM, in 100 mM TRIS buffer at pH=7.5) with elastase.

Example 28

Synthesis of a Cysteine Protease Inhibitor with a 6 Membered Homocyclic Substituted Aromatic Ring as the EWG Synthesis of Boc-phenylalanyl-homophenylalanyl-p-nitrostyryl, abbreviated herein as Boc-Phe-Hph-VNS, was as follows. Triphenylphoshine (10 gm, 38.1 mmmol) and 4-chloro-p-nitrophenyl (6.54 g, 38.1 mmol) were dissolved in 200 ml of THF and heated at reflux for 2 days. The white solid was filtered and washed with 200 ml diethyl ether and placed in vacuo for 16 hours.

p-nitromethylphenyltriphenylphosponium chloride (1.20 g, 2.77 mmol) was dissolved in 50 ml $H_2O$ and 1.4 ml of 2 M, (2.77 mmol) sodium hydroxide was added. An immediate glassy red colored solid was formed, and the $H_2O$ layer was extracted with 100 ml of toluene. The organic layer was dried over $K_2CO_3$, filtered and concentrated to dryness. The resulting red solid was dissolved in 100 ml of THF and 0.73 g (2.77 mmol) of Boc-homophenylalanyl aldehyde was added. The solution turned yellow over time. The reaction was complete after 16 hours. The reaction mixture was diluted with 250 ml of $CH_2Cl_2$ and washed with 200 ml of 1 M HCl, and 200 ml of saturated aqueous $NaHCO_3$, dried over $MgSO_4$, filtered and concentrated to dryness. The residue was dissolved in 20 ml of a 20% ETOAc/hexane solution and eluted down a silica gel column with 20% ETOAc/hexane solution. 25 ml fractions were collected. Fractions 6–12 were combined and concentrated to dryness. 340 mg of a 50/50 mixture of cis-trans configuration of Boc-homophenylalanyl-p-nitrostyryl was recovered.

The 340 mg (0.89 mmol) of Boc-homophenylalanyl-p-nitrostyryl was dissolved in 10 ml of HCl in dioxane (4 M) and left to stir under a drying tube for 30 minutes and then concentrated to a yellow foam.

0.29 g (0.98 mmol) Boc-phenylalanine was dissolved in 50 ml of THF and 216 µl (1.96 mmol) of N-methylmorpholine was added. The reaction was then stirred at 0° C. for 5 minutes under argon and 129 µl (0.98 mmol) of isobutylcholorformate was added, and a white precipitate began to form. After 5 minutes, the HCl salt of homophenylalanyl-p-nitrostyryl (284 mg, 0.98 mmol) in 10 ml of DMF was added and the reaction was allowed to warm up to room temperature over 16 hours. The reaction was then concentrated and then diluted with 200 ml of $CH_2Cl_2$ and washed with 200 ml of 1 M HCl and 200 ml of saturated aqueous $NaHCO_3$, dried over $K_2CO_3$, filtered and concentrated to dryness. The product was dissolved in 10 ml EtOAc and diluted with 20 ml of diethyl ether, and a white solid was filtered and dried in vacuo. 200 mgs of the resulting product, Boc-phenylalanyl-homophenylalanyl-p-nitrostyryl, was recovered as a 50/50 mixture of cis and trans configuration as determined by $^1$H NMR, and by TLC: 30% EtOAc/hexane, with bromo creoso green stain: $R_f$ of the two forms, cis and trans, was 0.48 and 0.54.

Example 29

Assay of a Cysteine Protease Inhibitor with a 6 Membered Substituted Homocyclic Ring as the EWG The cysteine protease inhibitor made in Example 15, Boc-phyenylalanylhomophenylalanylvinyl-p-nitrostyryl, was tested against cathepsin S, as outlined in Example 12. The inhibitor showed a $k_{obs}$/[I] value of 40,100 $M^{-1}sec^{-1}$.

Example 30

Synthesis of a Cysteine Protease Inhibitor with a Dienylsulfone as the EWG

Synthesis of (S)-(E,E)-5-(4-morpholinecarbonylphenylalanyl)amino-7-phenyl-1- phenylsuflonyl-1,3-heptadiene (Mu-Phe-Hph-DIESPh). a) Diethyl phosphonoacetyl N,O-dimethylhyroxamide {(EtO)$_2$POCH$_2$CON(Me)OMe} was prepared in 82% yield from diethyl phosphonoacetic acid and N,O-dimethylhydroxylamine hydrochloride in the presence of dicyclohexylcarbodiimide and triethylamine. b) To a solution of {(EtO)$_2$POCH$_2$CON(Me)OMe (1.13 g, 4.71 mmol) in THF (25 mL) at 0° C. was added sodium hydride (0.188 g, 4.71 mmol as a 60% mineral oil dispersion. After 15 minutes, a solution of Boc-homophenylalanlanal (1.24 g, 4.71 mmol) in THF (5 mL) was added. The mixture was stirred for 30 minutes. 1M HCl (50 mL) was added. The intermediate, (S)-(E)-4-tert-butoxycarbonylamino-6-phenyl-2-hexenoyl N,O-dimethylhydroxamide (Boc-HphVAMN(Me)OMe) was extracted with ethyl acetate (50 mL), washed with saturated aqueous sodium bicarbonate (50 mL) and brine (50 mL), dried over MgSO$_4$, filtered, and the solvent was removed under reduced pressure. c) The resulting oil was dissolved in THF (25 mL) and cooled to 0° C. Lithium aluminum hydride (5 mL of a 1.0M THF solution) was added. The solution was stirred for 20 minutes. Water (5 mL) was carefully added, followed by 1M HCl (30 mL). The next intermediate, (S)-(E)-4-tert-butoxycarbonylamino-6-phenyl-2-hexenal (Boc-HphVAl) was extracted into ethyl acetate (50 mL), washed with saturated aqueous sodium bicarbonate (30 mL) and brine (30 mL), dried over MgSO$_4$, filtered, and the solvent was removed under reduced pressure. TLC: (30% ethyl acetate/hexane) R$_f$=0.31. The crude material, weighing 1.36 g, was used immediately in the next step. d) To a solution of PSMP (1.38 g, 4.71 mmol) in THF (20 mL) at 0° C. was added sodium hydride (0.188 g of a 60% mineral oil dispersion, 4.71 mmol). The mixture was stirred for 15 minutes, whereupon a 5 mL THF solution of Boc-HphVAl from the previous step was added. The mixture was stirred for 40 minutes. 1M HCl (25 mL) was added. The intermediate, (S)-(E,E)-5-tert-butoxycarbonylamino-7-phenyl-1-phenylsulfonyl-1,3-heptadiene (Boc-Hph-DIESPh), was extracted with ethyl acetate (25 mL), washed with saturated aqueous sodium bicarbonate (25 mL), brine (25 mL), dried over MgSO$_4$, filtered, and the solvent was removed under reduced pressure. The residue was crystallized from CH$_2$Cl$_2$/ether/hexane to give 0.80 g (39%) from Boc-homophenylalaninal. TLC: (30% ethyl acetate/hexane) R$_f$=0.16. e) To a solution of Boc-HphDIESPh (0.80 g, 1.87 mmol) in ether/CH$_2$Cl$_2$ (3 mL, 2:1) was added a solution of anhydrous p-toluenesulfonic acid (0.80 g, 4.70 mmol) in ether (3 mL). The mixture was stirred at room temperature overnight. An additional 5 mL aliquot of CH$_2$Cl$_2$ was added and stirring permitted to continue for another 24 hours. Ether (80 mL) was then added. The solids were filtered, washed with ether (2×20 mL), and dried in vacuo to give 0.69 g (74%) of the intermediate, (S)-(E,E)-5-amino-7-phenyl-1-phenylsulfonyl-1,3-heptadiene 4-toluenesulfonate (TsOH.HphDIESPh). f) To a solution of Mu-PheOH (0.334 g, 1.20 mmol) in THF (7 mL) at −10° C. were added 4-methylmorpholine (0.132 mL, 1.20 mmol) and isobutyl chloroformate (0.156 mL, 1.20 mmol). The mixed anhydride was stirred for 5 minutes, whereupon TsOH.HphDIESPh (0.60 g, 1.20 mmol) was added, followed by 4-methylmorpholine (0.132 mL, 1.20 mmol). The reaction mixture was stirred for 45 minutes. Ethyl acetate (40 mL) was added. The solution was washed with 1M HCl, saturated aqueous sodium bicarbonate, and brine (5 mL each), dried over MgSO$_4$, filtered, and the solvent was removed under reduced pressure. The product, Mu-Phe-HphDIESPh, formed an oil on attempts to crystallize it. The supernatant was discarded and the residue was dried in vacuo, resulting in a foam (0.43 g, 61%).

TLC (50% ethyl acetate/CH$_2$Cl$_2$) R$_f$=0.29. $^1$H NMR (CDCl$_3$): 1.6–1.95 (2H, m, CH$_2$CH$_2$C$_6$H$_5$); 2.57 (2H, m, CH$_2$CH$_2$C$_6$H$_5$); 3.03 (2H, 2×dd, PhCH$_2$CH); 3.25 (4H, NCH$_2$CH$_2$O); 3.59 (4H, m, NCH$_2$CH$_2$O); 4.43 (1H, m*, CHNH (Hph)); 4.48 (1H, q*, J=6 Hz, CHNH (Phe)); 5.05 (1H, d, J=6 Hz, NHCH (Mu)); 5.86 (2H, m*, CH=CH); 6.09 (1H, d, J=6 Hz, NHCH); 6.26 (1H, d, J=12 Hz, SO$_2$CH=CH); 7.04–7.92 (16H, m, 15×aromatic and one CH=CH). The presence of a smaller doublet at 4.96 ppm, assigned as an NHCH peak corresponding to the morpholine urea, suggests that the all-trans configuration anticipated by performance of successive Wadsworth-Emmons reactions may in this sequence result in at least one of the double bonds in a minor component of the product being of cis configuration.

Example 31

Synthesis of a Cysteine Protease Inhibitor with a Vinyl Sulfone as the EWG with a Fluoro Moiety as an Additional EWG Attached to the Same Carbon of the Alkene Bond Synthesis of (S)-(E,Z)-1-fluoro-3-(4-morpholinecarbonyl-phenylalanyl) amino-5-phenyl-1-phenylsulfonyl-1-pentene (Mu-Phe-Hph-VSPh-VF). a) To a solution of diethyl phenylsulfonylmethylenephosphonate (5.06 g, 17.31 mmol) in THF (100 mL) at 0° C. was added sodium hydride (0.83 g of a 60% mineral oil dispersion, 20.77 mmol). The mixture was stirred for 20 minutes. N-fluorodiphenylsulfonimide (8.73 g, 27.69 mmol) was added as a solid. The mixture was stirred at room temperature overnight. The fluorinated Wadsworth-Emmons reagent, diethylphosphonylphenylsulfonylfluoromethane (PSMP-F) was isolated by partitioning between ethyl acetate (100 mL) and 1M HCl (100 mL). The organic phase was washed with saturated aqueous sodium bicarbonate (100 mL), brine (50 mL), dried over MgSO$_4$, filtered, and the solvent was removed under reduced pressure. The residue was purified by column chromatography (60–200 mesh silica gel, 0–20% ethyl acetate/CH$_2$Cl$_2$, gradient elution) to give 2.03 g (38%) of PSMP-F. TLC: (20% ethyl acetate/CH$_2$Cl$_2$) R$_f$=0.5. $^1$H NMR (CDCl$_3$): 1.37 (6H, 2×t, 2×CH$_3$); 4.26 (4H, m, 2×CH$_2$OP); 5.39 (1H, dd, CHFP); 7.57–8.03 (5H, m*, aromatic). b) To a solution of PSMP-F (1.00 g, 3.22 mmol) in THF (15 mL) at 0° C. was added sodium hydride (0.129 g of a 60% mineral oil dispersion). The mixture was stirred for 10 minutes, whereupon a solution of Boc-homophenylalaninal (0.42 g, 1.59 mmol) in THF (5 mL) was added. The mixture was stirred for 30 minutes. 1M HCl (10 mL) was added. The products, (S)-(E)-1-fluoro-3-tert-butoxycarbonylamino-5-phenyl-1-phenylsulfonyl-1-pentene and (S)-(Z)-1-fluoro-3-tert-butoxycarbonylamino-5-phenyl-1-phenylsulfonyl-1-pentene(Boc-Hph-VSPh-VF) were extracted into ethyl acetate (30 mL), washed with saturated aqueous sodium bicarbonate (10 mL), brine (10 mL), dried over MgSO$_4$, filtered, and the solvent was removed under reduced pressure. TLC: (30% ethyl acetate/hexane) R$_f$=0.29 and 0.39. c) The material from the Wadsworth-Emmons coupling was dissolved in ether (2 mL). A solution of anhydrous 4-toluenesulfonic acid (0.67 g, 3.98 mmol) in ether (2 mL). The mixture was stirred at room temperature overnight. Ether (30 mL) was added. The solids were filtered, washed with ether (2×20 mL), and dried in vacuo to give 0.42 g (54%) (S)-(E)-1-fluoro-3-amino-5-phenyl-1-phenylsulfonyl-1-pentene 4-toluenesulfonate and (S)-(Z)-1-fluoro-3-amino-5-phenyl-1-phenylsulfonyl-1-pentene4-toluenesulfonate (TsOH.Hph-VSPh-VF) in an approximately 5:3 ratio as evidenced by NMR. $^1$H NMR (DMSO-d$^6$): 1.82–2.07 (2H, m, CH$_2$CH$_2$C$_6$H$_5$); 2.28 (3H, s, CH$_3$C$_6$H$_4$SO$_3^-$); 2.37–2.73 (2H, m*, CH$_2$CH$_2$C$_6$H$_5$); 4.02 (0.63H, m*, CHNH (E isomer)); 4.83 (0.37H, m*, CHNH (Z isomer)); 6.22–6.34 (0.37H, dd, J=6,6 Hz, CH=CF (Z isomer)); 6.43 (0.63H, dd, J=6,18 Hz, CH=CF (trans isomer)); 7.04–8.04 (14 H, m, aromatic) 8.22 (3H, br s, NH$_3^+$). d) To a solution of Mu-PheOH (0.238 g, 0.854 mmol) in THF (5 mL) at −10° C. were added 4-methylmorpholine (94 (L, 0.854 mmol) and isobuty) chloroformate (0.111 mL, 0.854 mmol). The mixture was stirred for 5 minutes, whereupon TsOH.HphVSPh-VF (0.42 g, 0.854 mmol) was added, followed by 4methylmorpholine (94 (L, 0.354 mmol). The mixture was stirred for 45 minutes. Ethyl acetate (20 mL) was added. The mixture was washed with 1M HCl (10 mL), saturated aqueous sodium bicarbonate (5 mL). brine (5 mL), dried over MgSO$_4$, filtered, and the solvent was removed under reduced pressure. Yield=0,32 g (64%).

Example 32

In vitro Activity of Selected Michael Acceptors as Cysteine Protease Inhibitors Against the Protozoans of *Leishmania donovani*, *Trypanosoma cruzi*, and *Trypanosoma brucei*

In this table, the in vitro antiprotozoal activities of the indicated compounds were measured as percentage inhibition of *Leishmania donovani* amastigote infecteda mouse peritoneal macrophages, *Trypanosoma cruzi* amastigote infected macrophages, and *Trypanosoma brucei* extracellular bloodstream forms. Where indicated, the term "T" indicates the molecule to have displayed cytotoxicity.

| Compound (uM) | 90 | 30 | 10 | 3 | 1 | ED50 |
|---|---|---|---|---|---|---|
| Mu-Leu-Hph-VSPh | | | | | | |
| L. donovani | T | 15.3 | 0 | 4.6 | | |
| T. cruzi | T | 11.4 | 0 | 0 | | |
| T. brucei | 100 | 84.7 | 82.2 | 11.2 | | |
| Mu-Phe-HphVSPh | | | | | | |
| L. donovani | T | 9.4 | 0 | 0 | | |
| T. cruzi | T | 50.1 | 10 | 10 | | |
| T. brucei | 100 | 100 | 82.7 | 90.5 | 10.2 | 2.19 |
| Mu-Phe-ArgVSPh.HBr | | | | | | |
| L. donovani | 1.3 | 0 | 0 | 0 | | |
| T. cruzi | 5.8 | 0 | 0 | 0 | | |
| T. brucei | 0 | 0 | 0 | 0 | | |
| Mu-Phe-Hph-VAMBzl | | | | | | |
| L. donovani | 23.3 | 14.2 | 0 | 0 | | |
| T. cruzi | 5.83 | 0 | 0 | 0 | | |
| T. brucei | 0 | 0 | 0 | 0 | | |
| Mu-Phe-AlaVSMe | | | | | | |
| L. donovani | 6.7 | 0 | 0 | 0 | | |
| T. cruzi | 12.2 | 11.2 | 0 | 0 | | |
| T. brucei | 0 | 0 | 0 | 0 | | |
| HCl.Gly-Phe-VSPh | | | | | | |
| L. donovani | 4.02 | 0 | 0 | | | |
| T. cruzi | 0 | 0.1 | 0 | 0 | | |
| T. brucei | 0 | 0 | 0 | 0 | | |
| Boc-Asp(O-t-Bu)VSMe | | | | | | |
| L. donovani | 12.9 | 13.4 | 0 | 0 | | |
| T. cruzi | 9.9 | 0 | 0 | 0 | | |
| T. brucei | 0 | 0 | 0 | 0 | | |

-continued

| Compound (uM) | 90 | 30 | 10 | 3 | 1 | ED50 |
|---|---|---|---|---|---|---|
| HCl.PheVSMe | | | | | | |
| L. donovani | 100 | 100 | 100 | 100 | | |
| T. cruzi | 17.3 | 0 | 0 | 0 | | |
| T. brucei | 0 | 0 | 0 | 0 | | |
| Mu-Phe-ValVSPh | | | | | | |
| L. donovani | T | 100 | 100 | 100 | | |
| T. cruzi | 74.2 | 18.9 | 6.2 | 5.5 | | 61.88 |
| T. brucei | 100 | 72.7 | 35.4 | 13.5 | 11.9 | 13.85 |
| HCl.(e-Z)LysVSPh | | | | | | |
| L. donovani | T | T | 100 | 100 | | |
| T. cruzi | 97.8 | 82.8 | 10.6 | 2.7 | | 18.34 |
| T. brucei | 100 | 100 | 39.3 | 13 | 7.6 | 8 |
| Mu-Phe-Ser(OBzl)VSPh | | | | | | |
| L. donovani | T | 100 | 100 | 100 | | |
| T. cruzi | 50.7 | 15.1 | 15.7 | 5.2 | | |
| T. brucei | 100 | 1.00 | 93.3 | 11.5 | 5.2 | |
| Mu-Phe-(e-Z)LysVSPh | | | | | | |
| L. donovani | 0 | 0 | 0 | 0 | | |
| T. cruzi | 0 | 0 | 0 | 0 | | |
| T. brucei | 100 | 100 | 81.3 | 29.9 | 19.8 | 3.64 |
| Mu-Phe-HphStyrNO2 | | | | | | |
| L. donovani | 20.5 | 10.8 | 4 | 5.3 | | |
| T. cruzi | 12.2 | 0 | 0 | 0 | | |
| T. brucei | 100 | 100 | 0 | 0 | | |

Example 33

In vitro Activity of Selected Michael Acceptors as Cysteine Protease Inhibitors Against the Malarial Parasites *P. falciparum* (human) and *P. vinckei* (mouse)

The following table summarizes the comparative IC$_{50}$ values for selected cysteine protease inhibitors against the human malarial parasite *Plasmodium falciparum* and the mouse malarial parasite *Plasmodium vinckei*. The substrate used to measure in vitro protease activity was Z-Phe-Arg-AMC.

| Compound | P. falciparum IC$_{50}$ (human) | P. vinckei IC$_{50}$ (murine) |
|---|---|---|
| Mu-Phe-AlaVSMe | 20 μM | |
| Mu-Phe-HphVSMe | 1 μM | 1 μM |
| Mu-Phe-PheVSMe | 2 μM | |
| HCl.Ala-PheVSMe | >100 μM | |
| Mu-Phe-ArgVSPh.HBr | 50 nM | 50 nM |
| Mu-Phe-HphVSPh | 80 nM | 50 nM |
| Mu-Phe-(e-Z)LysVSPh | 100 nM | 80 nM |
| Mu-Phe-LysVSPh.HBr | 100 nM | 60 nM |
| Mu-Phe-ValVSPh | 1 μM | 1 μM |
| Mu-Phe-Ser(OBzl)VSPh | 1 μM | 500 nM |
| Mu-Leu-HphVSPh | 3 nM | 200 nM |
| Mu-Phe-HphVEOEt | 300 nM | 300 nM |
| Mu-Phe-ArgVEOEt.HBr | 300 nM | 200 nM |
| Mu-Phe-HphVA | 1 μM | 2 μM |
| Mu-Phe-HphVAMLeu-ProOMe | 80 nM | 600 nM |
| Mu-Phe-HphVAMBzl | 200 nM | 2 μM |
| Mu-Phe-HphVPEt | 3 μM | |
| Mu-Phe-HphStyrNO$_2$ | 2 μM | 8 μM |

Example 34
Treatment of Rheumatoid Arthritis with Peptidyl Vinylsulfones

At day zero, Female Lewis rats (5/group), 5 weeks old, were given intradermal injection into the base of the tail of

*Mycobacterium butyricum* in 0.1 ml of light mineral oil. The animals were provided Teklad (4%) rat chow mixed with (treated groups) or without compound (control group) and water ad libitum. The compounds used were Mu-Phe-HphVSPh, Mu-Leu-HphVSPh, Mu-Tyr-HphVSPh, Mu-Phe-Lys($\epsilon$-Z)VSPh, Mu-Phe-LysVSPh-HBr. The compounds were given to three groups at 3, 10, and 30 mg/kg/day, respectively. The following parameters were noted: biweekly weights and biweekly joint evaluations by the following scoring system: paw swelling 0=no edema, 1=slight edema of small digital joints, 2=edema of the digital joints and foot pad, 3=gross edema of the entire foot pad below that ankle or elbow, 4=gross edema of the entire foot pad including the ankle and elbow joint Erythema was scored as: 0=normal, 1=pink, 2=red, 3=deep violaceous. The evaluators were blinded as to treatment groups.

After 28 days the animals were killed and the hind paws and knees were removed and fixed in 4% paraformaldehyde. The bones were decalcified in Fisher Decalcifying Solution (chelating agent, 3 mM HCl 1.35 N) and then embedded in paraffin (58°, 3×45 min). Joint histopathology scores were calculated by the following method: two sections of each joint were read for synovial cell proliferation, cartilage erosion, bone erosion, fibroproliferative pannus, diffuse inflammatory synovitis, and synovial vasculitis: 0=normal, 1=mild, 2=moderate, 3=and severe. The sections were examined by two independent investigators blinded as to treatment groups, and the mean score then used as the score for that section.

Mu-Phe-HphVSPh showed a dose dependent beneficial effect on all scores. The high dose of Mu-Leu-HphVSPh also showed a reduction in bone and cartilage destruction.

Example 35

Activity of Peptidyl Vinylsulfones Against *P. carinii*

Mu-Leu-HphVSPh and Mu-Phe-LysVSPh.HBr were evaluated for their effects on the growth of *P. carinii* in vitro, according to the procedure of M. S. Bartlett et al. [Antimicrotubule Benzimidazoles Inhibit In Vitro Growth of *P. carinii*, M. S. Bartlett, T. D. Edlind, M. M. Durkin, M. M. Shaw, S. F. Queener, and J. W. Smith, (1992) Antimicrobial Agents and Chemotherapy, 36, 779–782; Antimicrobial susceptibility of *P. carinii* in culture, M. S. Bartlett, R. Eichholtz, and J. W. Smith (1985) Diagn. Microbiol. Infect. Dis.; 3, 381–387. Mu-Leu-HphVSPh and Mu-Phe-LysVSPh.HBr (10 mM each) inhibited the growth of *P. carinii* 64% and 50% respectively.

Example 36

Activity of Peptidyl Vinylsulfones and One Vinyl Amide Against *T. cruzi*

Irradiated J774 cells were infected with *T. cruzi* and simultaneously treated with 20 mM of peptidyl vinyl derivatives for 5 days; thereafter without inhibitor. The following compounds were effective in decreasing order: Mu-Phe-ArgVSPh, Boc-Tyr(I$_2$)-HphVSPh, Mu-Phe-ValVSPh, Boc-Tic-HphVSPh, Mu-Phe-Ser(OBzl)VSPh, Mu-Leu-HphVSPh, Mu-Tyr(I$_2$)-HphVSPh, Mu-Phe-LysVSPh, Mu-Tic-HphVSPh.

Example 37

Effect of Peptidyl Vinylsulfones on Glioma Cell Migration

Two permanent human glioma cell lines (U87MG and U251MGn) and a well characterized low passage primary culture derived from a CB-positive glioblastoma (HF66) were used to assess the migratory behavior in the Matrigel barrier migration assay in the presence of graded concentrations of four compounds.

Using the Matrigel assay, Mu-Leu-HphVSPh, Mu-Tyr-HphVSPh, Mu-Phe-HphVSPh, and Mu-Tyr(I$_2$)-HphVSPh (all at 10 mM) inhibited U251MGn by 67, 56, 29, & 20% respectively, while the U87MG cells were inhibited 53, 75, 63, & 56% respectively. The primary culture HF66 cells were inhibited only 10% by these compounds at the same concentration.

Example 38

Inhibition of Calpain

The inhibitors were tested against calpain at 1 or 2% as for the other enzymes. The reaction conditions were 50 mM Tris, pH 7.5, 5 mM CaCl$_2$, 2.5 mM DTT, assayed at 25° C. The substrate was 100 $\mu$M Suc-Leu-Tyr-AMC. The results are shown in Table 6.

TABLE 6

Inactivation of Calpain-1, 2%

| Inhibitor | $k/K_I$ or $k_{obs}/[I]^*$ ($M^{-1}sec^{-1}$) | $k_{in}$, $sec^{-1}$ | $K_I$, $\mu$M |
|---|---|---|---|
| Boc-D(O-tBu)VSMe | 0 | — | — |
| Mu-DL-Fam-HphVSPh | 0 | | |
| Mu-Tic-HphVSPh | 0 | — | — |
| Boc-Tic-HphVSPh | 0 | — | — |
| Boc-Tyr(I$_2$)HphVSPh | 0 | — | — |
| Ac-Tyr-Val-Ala-AspVSPh | 0 | — | — |
| Mu-Phe-AlaVSMe | <50* | — | — |
| Mu-Phe-HphVPhe | <50* | — | — |
| Mu-Phe-HphVAMBzl | <50* | — | — |
| Mu-Phe-HphVPhos | <50* | — | — |
| Mu-Phe-KysVSPh | <50* | — | — |
| Mu-Phe-Ser(OBzl)VSPh | <50*- | — | — |
| Mu-Phe-KysVSPh | <50* | — | — |
| Mu-Phe-ArgVSPh | <50* | — | — |
| Mu-Phe-HphVSPh | <50* | — | — |
| Mu-ARg-ArgVSPh | <50* | — | — |
| Mu-Phe-LysVE | <50* | — | — |
| Boc-Ala-PheVSMe | 60* | — | — |
| Phe-VSPh | <50* | — | — |
| Gly-PheVSPh | <50* | — | — |
| Mu-Val-PheVSPh | 110* | — | — |
| Mu-Phe-ValVSPh | 180* | — | — |
| Mu-Phe-PheVSMe | 260* | — | — |
| Ac-Leu-Leu-MetVSPh | 5,600* | — | — |
| Ac-Leu-Leu-NleVSPh | 6,900* | — | — |
| Mu-Leu-Leu-Tyr-VSPh | 7,600* | — | — |
| Ac-Leu-Leu-Met(O$_2$)VSPh | 8,400* | — | — |
| Mu-Leu-Leu-TyrVSPh | 10,800% | — | — |
| Z-Leu-Leu-Tyr-VSPh | 36,400% | — | — |
| Z-leu-Leu-TyrVSPh | 24,300 | — | — |

We claim:

1. A cysteine protease inhibitor of the formula:

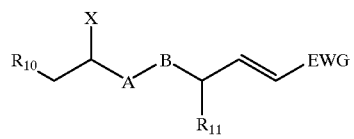

wherein

EWG is phosphonate, sulfoxide, sulfonamide, sulfinamide, sulfoximine, sulfonate, C(O)OR$_1$, S(O$_2$)R$_2$, C(O)NHCH(Z)C(O)Q, or C(O)R$_4$;

$R_1$ is $(C_5)$alkyl, $(C_{3-7})$cycloalkyl, $(C_{3-7})$cycloalkyl$(C_{1-5})$alkyl, optionally substituted aryl, or optionally substituted $(C_{7-12})$aralkyl, wherein said optional substituents are one or two groups of $(C_{1-5})$alkyl, $(C_{1-5})$alkoxy, halogen of atomic number 9 to 35, hydroxy, amino, or halogen substituted $(C_{1-5})$alkyl;

$R_2$ is substituted $(C_1)$alkyl, optionally substituted $(C_{2-5})$alkyl, (wherein said substituent groups of said $(C_1)$alkyl and $(C_{2-5})$alkyl are $(C_{1-5})$alkoxy, halogen of atomic number from 9 to 35, hydroxy, amino, nitro, arylsulfonyl, or halogen-substituted $(C_{1-5})$alkyl), $(C_{3-7})$cycloalkyl, $(C_{3-7})$cycloalkyl$(C_{1-5})$alkyl, $(C_{3-7})$cycloalky$(C_{1-5})$alkenyl, $(C_{5-12})$aryl, or $(C_{7-12})$aralkyl, wherein said $(C_{5-12})$aryl, or $(C_{7-12})$aralkyl are optionally substituted with one or two groups of $(C_{1-5})$alkoxy, halogen of atomic number from 9 to 35, hydroxy, amino, nitro, alkyl, arylsulfonyl or halogen-substituted $(C_{1-5})$alkyl;

Q is hydrogen, ester, $NH_2$, NH—$(C_{1-5})$alkyl NH—$(C_{3-7})$cycloalkyl, NH—$(C_{3-7})$cycloalky$(C_{1-5})$alkyl, NH—$C_{5-12})$aryl, NH—$(C_{7-12})$aralkyl, N-di$(C_{1-5})$alkyl, N-di$(C_{3-7})$cycloalkyl, N-di$(C_{3-7})$cycloalkyl$(C_{1-5})$alkyl, N-di$(C_{5-12})$aryl, or N-di$(C_{7-12})$aralkyl, wherein said aryl and aralkyl groups are optionally substituted with one or two $(C_{1-5})$alkyl, $(C_{1-5})$alkoxy, halogen of atomic number 9 to 35, hydroxy, amino, nitro, $(C_{1-5})$alkyl, $(C_{5-12})$arylsulfonyl, or halogen-substituted $(C_{1-5})$alkyl;

$R_4$ is $(C_{2-5})$alkyl, $(C_{3-7})$cycloalkyl, $(C_{3-7})$cycloalky$(C_{1-5})$alkyl, $(C_{3-7})$cycloalky$(C_{1-5})$alkenyl, optionally substituted $(C_{5-12})$aryl, or optionally substituted $(C_{7-12})$aralkyl, wherein said substituent groups are one or two $(C_{1-5})$alkyl, $(C_{1-5})$alkoxy, halogen of atomic number 9 to 35, hydroxy, amino, nitro, $(C_{1-5})$alkyl, $(C_{5-12})$arylsulfonyl, halogen-substituted $(C_{1-5})$alkyl or perfluoro;

$R_{10}$ is hydrogen, a peptide amino end blocking group, a peptide residue with or without an amino end blocking group, or a single amino acid with or without an amino end blocking group, wherein said amino end blocking group is selected from the group consisting of alkoxy-ω-oxoalkanoyl of 2 to 10 carbon atoms, alkoxycarbonyl of 2 to 10 carbon atoms, alkanoyl of 2 to 10 carbon atoms, cycloalkylcarbonyl of 4 to 8 carbon atoms, carbamoyl, alkylcarbamoyl, dialkylcarbamoyl, benzoyl, or alkylsulfonyl of 1 to 10 carbon atoms;

X, $R_{11}$, and Z are amino acid side chains in the (R) or (S) configuration;

A—B is a peptide linkage or peptidomimetic linkage; and wherein the second order rate constant for inhibition of a cysteine protease with said inhibitor ($k_{irr}/K_I$) is at least about $1000\ M^{-1}sec^{-1}$.

2. The cysteine protease inhibitor of claim 1 of the formula:

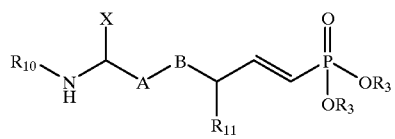

wherein $R_3$ is $(C_{1-5})$alkyl, $(C_{3-7})$cycloalkyl, $(C_{3-7})$cycloalky$(C_{1-5})$alkyl, $(C_{3-7})$cycloalkyl$(C_{1-5})$alkenyl, optionally substituted $(C_{5-12})$aryl, or optionally substituted $(C_{7-12})$aralkyl, wherein said substituent groups are one or two $(C_{1-5})$alkyl, $(C_{1-5})$alkoxy, halogen of atomic number 9 to 35, hydroxy, amino, nitro, $(C_{1-5})$alkyl, $(C_{5-12})$arylsulfonyl, halogen-substituted $(C_{1-5})$alkyl, or perfluoro.

3. The cysteine protease inhibitor of claim 1 of the formula:

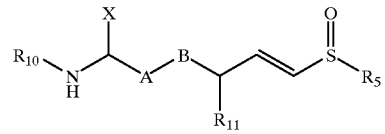

$R_5$ is $(C_{1-5})$alkyl, $(C_{3-7})$cycloalkyl, $(C_{3-7})$cycloalkyl$(C_{1-5})$alkyl, $(C_{3-7})$cycloalkyl$(C_{1-5})$alkenyl, optionally substituted $(C_{5-12})$aryl, or optionally substituted $(C_{7-12})$aralkyl, wherein said optional substituents are one to two groups of $(C_{1-5})$alkyl, $(C_{1-5})$alkoxy, halogen of atomic number of 9 to 35, hydroxy, amino, nitro alkyl, alylsulfonyl, halogen substituted $(C_{1-5})$alkyl or perfluoro.

4. The cysteine protease inhibitor of claim 1 of the formula:

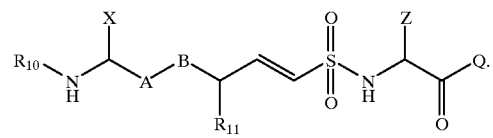

5. The cysteine protease inhibitor of claim 1 of the formula:

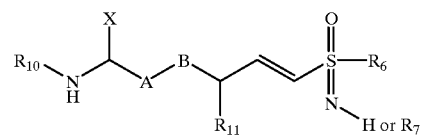

$R_6$ and $R_7$ are independently $(C_{1-5})$alkyl, $(C_{3-7})$cycloalkyl, $(C_{3-7})$cycloalky$(C_{1-5})$alkyl, $(C_{3-7})$cycloalkyl$(C_{1-5})$alkenyl, optionally substituted $(C_{5-12})$aryl, or optionally substituted $(C_{7-12})$aralkyl, wherein said substituent groups are one or two $(C_{1-5})$alkyl, $(C_{1-5})$alkoxy, halogen of atomic number 9 to 35, hydroxy, amino, nitro, $(C_{1-5})$alkyl, $(C_{5-12})$arylsulfonyl, halogen-substituted $(C_{1-5})$alkyl, or perfluoro.

6. A cysteine protease inhibitor of the formula:

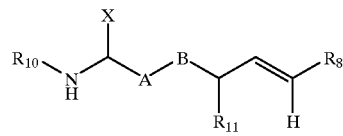

$R_{10}$ is hydrogen, a peptide amino end blocking group, a peptide residue with or without an amino end blocking group, a single amino acid with or without an amino end blocking group, wherein said amino end blocking group is selected from the group consisting of alkoxy-ω-oxoalkanoyl of 2 to 10 carbon atoms, alkoxycarbonyl of 2 to 10 carbon atoms, alkanoyl of 2 to 10 carbon atoms, cycloalkylcarbonyl of 4 to 8 carbon atoms, carbamoyl, alkylcarbamoyl, dialkylcarbamoyl, benzoyl, alkylsulfonyl of 1 to 10 carbon atoms;

A—B is a peptide linkage or peptidomimetic linkage;

$R_8$ is a five or six membered homocyclic aromatic ring with at least one substituted group selected from EWM, MDG, and DG, wherein EWM is ester, sulfone, carboxylate, amide, phosphonate, ketone, nitrile, sulfonate, sulfoxide, sulfonamide, sulfinamide, or sulfoximine; MDG is $SO_3H$, $SO_2R$, $SOR$, $SO_2NH_2$, $SO_2NHR$, $SO_2N(R)_2$, $SONH_2$, $SONHR$, $SON(R)_2$, $CN$, $PO_3H$, $P(O)(OR)_2$, $P(O)OR$, $OH$, $COOH$, $COR$, $COOR$, or $NRRR^+$, wherein each R is independently an aryl, alkyl, or aralkyl; and DG is a halogen; and wherein the second order rate constant for inhibition of a cysteine protease with said inhibitor ($k_{irr}/K_I$) is at least about 1000 $M^{-1}sec^{-1}$.

7. The cysteine protease inhibitor of claim 6 of the formula:

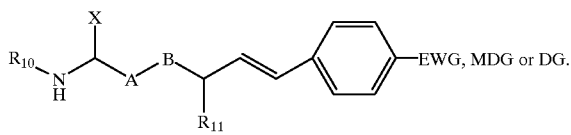

8. A cysteine protease inhibitor of the formula:

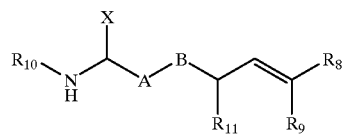

$R_{10}$ is hydrogen, a peptide amino end blocking group, a peptide residue with or without an amino end blocking group, a single amino acid with or without an amino end blocking group, wherein said amino end blocking group is selected from the group consisting of alkoxy-ω-oxoalkanoyl of 2 to 10 carbon atoms, alkoxycarbonyl of 2 to 10 carbon atoms, alkanoyl of 2 to 10 carbon atoms, cycloalkylcarbonyl of 4 to 8 carbon atoms, carbamoyl, alkylcarbamoyl, dialkylcarbamoyl, benzoyl, alkylsulfonyl of 1 to 10 carbon atoms;

X and $R_{11}$ are amino acid side chains in the (R) or (S) configuration;

A—B is a peptide linkage or peptidomimetic linkage;

$R_8$ is a five or six membered homocyclic aromatic ring with at least one substituted group selected from EWM, a MDG, and DG, wherein EWM is an ester, sulfone, carboxylate, amide, phosphonate, ketone, nitrile, nitro compound, sulfonate, sulfoxide, sulfonamide, sulfinamide, or sulfoximine; MDG is $NO_2$, $SO_3H$, $SO_2R$, $SOR$, $SO_2NH_2$, $SO_2NHR$, $SO_2N(R)_2$, $SONH_2$, $SONHR$, $SON(R)_2$, $CN$, $PO_3H$, $P(O)(OR)_2$, $P(O)OR$, $OH$, $COOH$, $COR$, $COOR$, or $NRRR^+$, wherein each R is independently an aryl, alkyl, or aralkyl; and DG is a halogen;

$R_9$ is methyl or a peptide; and wherein the second order rate constant for inhibition of a cysteine protease with said inhibitor ($k_{irr}/K_I$) is at least about 1000 $M^{-1}sec^{-1}$.

9. A cysteine protease inhibitor of the formula:

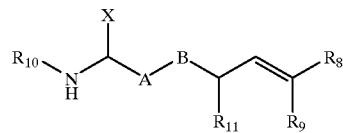

$R_{10}$ is hydrogen, a peptide amino end blocking group, a peptide residue with or without an amino end blocking group, a single amino acid with or without an amino end blocking group, wherein said amino end blocking group is selected from the group consisting of alkoxy-ω-oxoalkanoyl of 2 to 10 carbon atoms, alkoxycarbonyl of 2 to 10 carbon atoms, alkanoyl of 2 to 10 carbon atoms, cycloalkylcarbonyl of 4 to 8 carbon atoms, carbamoyl, alkylcarbamoyl, dialkylcarbamoyl, benzoyl, alkylsulfonyl of 1 to 10 carbon atoms;

X and $R_{11}$ are amino acid side chains in the (R) or (S) configuration;

A—B is a peptide linkage or peptidomimetic linkage;

$R_8$ is a five or six membered heterocyclic aromatic ring with at least one substituted group selected from EWM, a MDG, and DG, wherein EWM is an ester, sulfone, carboxylate, amide, phosphonate, ketone, nitrile, nitro compound, sulfonate, sulfoxide, sulfonamide, sulfinamide, or sulfoximine; MDG is $NO_2$, $SO_3H$, $SO_2R$, $SOR$, $SO_2NH_2$, $SO_2NHR$, $SO_2N(R)_2$, $SONH_2$, $SONHR$ $SON(R)_2$, $CN$, $PO_3H$, $P(O)(OR)_2$, $P(O)OR$, $OH$, $COOH$, $COR$, $COOR$, or $NRRR^+$, wherein each R is independently an aryl, alkyl, or aralkyl; and DG is a halogen;

$R_9$ is hydrogen, methyl or a peptide; and wherein the second order rate constant for inhibition of a cysteine protease with said inhibitor ($k_{irr}/K_I$) is at least about 1000 $M^{-1}sec^{-1}$.

10. A cysteine protease inhibitor of claim 9 of the formula:

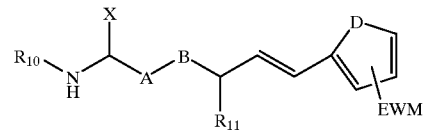

wherein D is oxygen, sulfur, nitrogen, phosphorus or arsenic.

11. The cysteine protease inhibitor of claim 9 of the formula:

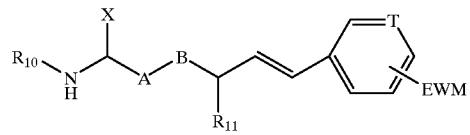

wherein T is nitrogen or phosphorus.

12. A cysteine protease inhibitor of the formula:

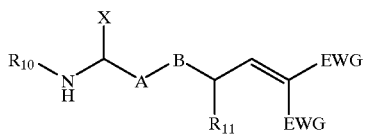

wherein $R_{10}$ is hydrogen, a peptide amino end blocking group, a peptide residue with or without an amino end blocking group, a single amino acid with or without an amino end blocking group wherein said amino end blocking group is selected from the group consisting of alkoxy-ω-oxoalkanoyl of 2 to 10 carbons, alkoxycarbonyl of 2 to 10 carbons, alkanoyl of 2 to 10 carbons, cycloalkylcarbonyl of 4 to 8 carbons, carbamoyl, alkylcarbamoyl, dialkylcarbamoyl, benzoyl, or alkylsulfonyl of 1 to 10 carbons;

X and $R_{11}$ are amino acid side chains in the (R) or (S) configuration;

A—B is a peptide linkage or peptidomimetic linkage;

EWG represents an ester, a sulfone, carboxylate, phosphonate, an amide, a ketone, a nitrite, a sulfoxide, a sulfoximine, a five or six membered homocyclic or heterocyclic aromatic ring with at least one substituted group selected from EWM, MDG, and DG, wherein EWM is an ester, sulfone, carboxylate, amide, phosphonate ketone, nitrite, nitro compound, sulfonate, sulfoxide, sulfonamide, sulfinamide, or sulfoximine; MDG is $NO_2$, $SO_3H$, $SO_2R$, SOR, $SO_2NH_2$, $SO_2NHR$, $SO_2N(R)_2$, $SONH_2$, SONHR, $SON(R)_2$, CN, $PO_3H$, $P(O)(OR)_2$, P(O)OR, OH, COOH, COR, COOR, or $NRRR^+$, wherein each R is independently an aryl, alkyl, or aralkyl; and DG is a halogen; and wherein the second order rate constant for inhibition of a cysteine protease with said inhibitor ($k_{irr}/K_I$) is at least about 1000 $M^{-1}sec^{-1}$.

13. A cysteine protease inhibitor of the formula:

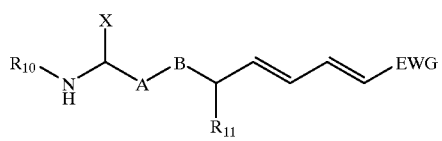

wherein $R_{10}$ is hydrogen, a peptide amino end blocking group, a peptide residue with or without an amino end blocking group, a single amino acid with or without an amino end blocking group wherein said amino end blocking group is selected from the group consisting of alkoxy-ω-oxoalkanoyl of 2 to 10 carbons, alkoxycarbonyl of 2 to 10 carbons, alkanoyl of 2 to 10 carbons, cycloalkylcarbonyl of 4 to 8 carbons, carbamoyl, alkylcarbamoyl, dialkylcarbamoyl, benzoyl, or alkylsulfonyl of 1 to 10 carbons;

X and $R_{11}$ are amino acid side chains in the (R) or (S) configuration;

A—B is a peptide linkage or peptidomimetic linkage;

EWG represents an ester, a sulfone, carboxylate, phosphonate, an amide, a ketone, a nitrite, a sulfoxide, a sulfoxamine, a five or six membered homocyclic or heterocyclic aromatic ring with at least one substituted group selected from EWM, MDG, and DG, wherein EWM is an ester, sulfone, carboxylate, amide, phosphonate, ketone, nitrile, nitro compound, sulfonate, sulfoxide, sulfonamide, sulfinamide, or sulfoximine; MDG is $NO_2$, $SO_3H$, $SO_2R$, SOR, $SO_2NH_2$, $SO_2NHR$, $SO_2N(R)_2$, $SONH_2$, SONHR, $SON(R)_2$, CN, $PO_3H$, $P(O)(OR)_2$, P(O)OR, OH, COOH, COR, COOR, or $NRRR^-$, wherein each R is independently an aryl, alkyl, or aralkyl; and DG is a halogen; and wherein the second order rate constant for inhibition of a cysteine protease with said inhibitor ($k_{irr}/K_I$) is at least about 1000 $M^{-1}sec^{-1}$.

14. A cysteine protease inhibitor of the formula:

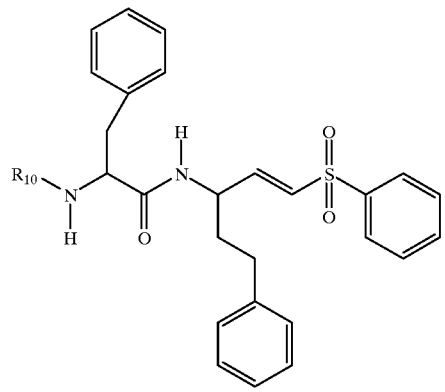

wherein $R_{10}$ is selected from the group consisting of hydrogen, a peptide residue of 1–3 amino acids with or without a peptide end blocking group, and a peptide end blocking group.

15. A method of inhibiting a cysteine protease comprising irreversibly binding the cysteine protease inhibitor of claims 1, 6, 8, 9, 12, 13 or 14 to said cysteine protease.

16. A cysteine protease inhibitor comprising a compound of the formula:

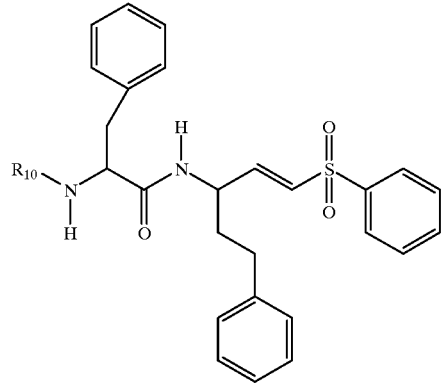

wherein $R_{10}$ is a pepetide and blocking group.

17. The cysteine protease inhibitor of claim 16 wherein said peptide end blocking group is selected from the group consisting of $C_{(2-10)}$alkoxy-ω-oxoalkanoyl, $C_{(2-10)}$alkoxycarbonyl, $C_{(2-10)}$alkanoyl, $C_{(4-8)}$cycloalkylcarbonyl, carbamoyl, dialkylcarbamoyl, benzoyl, $C_{(1-10)}$alkylsulfonyl. heterocycloarylcarbonyl of 4 to 10 atoms in the ring, and heterocycloalkylcarbonyl of 4 to 8 atoms in the ring.

18. The cysteine protease inhibitor of claim 17, wherein said $C_{(2-10)}$alkoxycarbonyl is $C_{(4-8)}$alkoxycarbonyl.

19. The cysteine protease inhibitor of claim 18, wherein said $C_{(4-8)}$alkoxycarbonyl is tert-butoxycarbonyl.

20. The cysteine protease inhibitor of claim 16 wherein said peptide end blocking group is heterocycloalkylcarbonyl.

21. The cysteine protease inhibitor of claim 20 wherein said heterocycloalkylcarbonyl is morpholinecarbonyl.

22. The cysteine protease inhibitor of claim 20 wherein said heterocycloalkylcarbonyl is cycloalkylaminocarbonyl.

23. The cysteine protease inhibitor of claim 22 wherein said cycloalkylaminocarbonyl is cycloalkyldiaminocarbonyl.

24. The cysteine protease inhibitor of claim 23 wherein said cycloalkyldiaminocarbonyl is (4-methyl-piperazin-1-yl)-methanoyl.

25. The cysteine protease inhibitor according to claim 24 wherein said cysteine protease inhibitor is 4-methylpiperazine-1-carboxylic acid [1-((E)-3-benzenesulfonyl-1-phenethyl-allylcarbamoyl)-2-phenyl-ethyl]-amide.

26. The cysteine protease inhibitor of claim 16 wherein said peptide end blocking group is benzyloxycarbonyl.

27. The cysteine protease inhibitor of claim 16, wherein said peptide end blocking group is heterocycloarylcarbonyl.

28. The cysteine protease inhibitor of claim 27, wherein said heterocycloarylcarbonyl is isoqinolinecarbonyl.

29. A method of making a cysteine protease inhibitor of the formula:

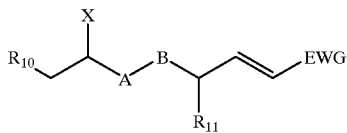

wherein

EWG is phosphonate, sulfoxide, sulfonamide, sulfinamide, sulfoximine, sulfonate, $C(O)OR_1$, $S(O_2)R_2$, $C(O)NHCH(Z)C(O)Q$, or $C(O)R_4$;

$R_1$ is $(C_5)$alkyl, $(C_{3-7})$cycloalkyl, $(C_{3-7})$cycloalkyl$(C_{1-5})$ alkyl, optionally substituted aryl, or optionally substituted $(C_{7-12})$aralkyl, wherein said optional substituents are one or two groups of $(C_{1-5})$alkyl, $(C_{1-5})$alkoxy, halogen of atomic number 9 to 35, hydroxy, amino, or halogen substituted $(C_{1-5})$alkyl;

$R_2$ is substituted $(C_1)$alkyl, optionally substituted $(C_{2-5})$ akyl, (wherein said substituent groups of said $(C_1)$alkyl and $(C_{2-5})$alkyl are $(C_{1-5})$alkoxy, halogen of atomic number from 9 to 35, hydroxy, amino, nitro, arylsulfonyl, or halogen-substituted $(C_{1-5})$alkyl), $(C_{3-7})$cycloalkyl, $(C_{3-7})$cycloalkyl$(C_{1-5})$alkyl, $(C_{3-7})$cycloalky$(C_{1-5})$alkenyl, $(C_{5-12})$aryl, or $(C_{7-12})$aralkyl, wherein said $(C_{5-12})$aryl, or $(C_{7-12})$aralkyl are optionally substituted with one or two groups of $(C_{1-5})$alkoxy, halogen of atomic number from 9 to 35, hydroxy, amino, nitro, alkyl, arylsulfonyl or halogen-substituted $(C_{1-5})$alkyl;

Q is hydrogen, ester, $NH_2$, NH—$(C_{1-5})$alkyl NH—$(C_{3-7})$cycloalkyl, NH—$(C_{3-7})$cycloalky$(C_{1-5})$alkyl, NH—$(C_{5-12})$aryl, NH—$(C_{7-12})$aralkyl, N-di$(C_{1-5})$alkyl, N-di$(C_{3-7})$cycloalkyl, N-di$(C_{3-7})$cycloalkyl$(C_{1-5})$alkyl, N-di$(C_{5-12})$aryl, or N-di$(C_{7-12})$aralkyl, wherein said aryl and aralkyl groups are optionally substituted with one or two $(C_{1-5})$alkyl, $(C_{1-5})$alkoxy, halogen of atomic number 9 to 35, hydroxy, amino, nitro, $(C_{1-5})$alkyl, $(C_{5-12})$arylsulfonyl, or halogen-substituted $(C_{1-5})$alkyl;

$R_4$ is $(C_{2-5})$alkyl, $(C_{3-7})$cycloalkyl, $(C_{3-7})$cycloalky$(C_{1-5})$ alkyl, $(C_{3-7})$cycloalkyl$(C_{1-5})$alkenyl, optionally substituted $(C_{5-12})$aryl, or optionally substituted $(C_{7-12})$ aralkyl, wherein said substituent groups are one or two $(C_{1-5})$alkyl, $(C_{1-5})$alkoxy, halogen of atomic number 9 to 35, hydroxy, amino, nitro, $(C_{1-5})$alkyl, $(C_{5-12})$ arylsulfonyl, halogen-substituted $(C_{1-5})$alkyl or perfluoro;

$R_{10}$ is hydrogen, a peptide amino end blocking group, a peptide residue with or without an amino end blocking group, or a single amino acid with or without an amino end blocking group, or a label, wherein said amino end blocking group is selected from the group consisting of alkoxy-ω-oxoalkanoyl of 2 to 10 carbon atoms, alkoxycarbonyl of 2 to 10 carbon atoms, alkanoyl of 2 to 10 carbon atoms, cycloalkylcarbonyl of 4 to 8 carbon atoms, carbamoyl, alkylcarbamoyl, dialkylcarbamoyl, benzoyl, or alkylsulfonyl of 1 to 10 carbon atoms, and wherein said label is selected from the group consisting of isotopic labels, immune labels, colored labels and fluorescent labels;

X, $R_{11}$, and Z are amino acid side chains in the (R) or (S) configuration;

A—B is a peptide linkage or peptidomimetic linkage; and wherein the second order rate constant for inhibition of a cysteine protease with said inhibitor ($k_{irr}/K_I$) is at least about 1000 $M^{-1}sec^{-1}$, said method comprising:

a) coupling a protected α-amino $R_{11}$ aldehyde with a Wadsworth-Emmons reagent containing said EWG to form a cysteine protease inhibitor intermediate;

b) deprotecting the cysteine protease inhibitor intermediate; and c) coupling the cysteine protease inhibitor intermediate with an N-protected X amino acid.

30. A method of making a cysteine protease inhibitor of the formula:

$$R_{10}-\underset{H}{N}-\overset{X}{\underset{A}{\bigg|}}-B-\underset{R_{11}}{\bigg|}-\overset{}{\underset{H}{=}}R_8$$

$R_{10}$ is hydrogen, a peptide amino end blocking group, a peptide residue with or without an amino end blocking group, a single amino acid with or without an amino end blocking group, or a label, wherein said amino end blocking group is selected from the group consisting of alkoxy-ω-oxoalkanoyl of 2 to 10 carbon atoms, alkoxycarbonyl of 2 to 10 carbon atoms, alkanoyl of 2 to 10 carbon atoms, cycloalkylcarbonyl of 4 to 8 carbon atoms, carbamoyl, alkylcarbamoyl, dialkylcarbamoyl, benzoyl, alkylsulfonyl of 1 to 10 carbon atoms, and wherein said label is selected from the group consisting of isotopic labels, immune labels, colored labels and fluorescent labels;

X and $R_{11}$ are amino acid side chains in the (R) or (S) configuration;

A—B is a peptide linkage or peptidomimetic linkage;

$R_8$ is a five or six membered homocyclic aromatic ring with at least one substituted group selected from EWM, MDG, and DG, wherein EWM is ester, sulfone, carboxylate, amide, phosphonate, ketone, nitrile, sulfonate, sulfoxide, sulfonamide, sulfinamide, or sulfoximine; MDG is $SO_3H$, $SO_2R$, SOR, $SO_2NH_2$, $SO_2NHR$, $SO_2N(R)_2$, $SONH_2$, SONHR, $SON(R)_2$, CN, $PO_3H$, $P(O)(OR)_2$, P(O)OR, OH, COOH, COR, COOR, or $NRRR^+$, wherein each R is independently an aryl, alkyl, or aralkyl; and DG is a halogen; and wherein the second order rate constant for inhibition of a cysteine protease with said inhibitor ($k_{irr}/K_I$) is at least about 1000 $M^{-1}sec^{-1}$, said method comprising:

a) coupling a protected α-amino $R_{11}$ aldehyde with a Wadsworth-Emmons reagent containing said $R_8$ group to form a cysteine protease inhibitor intermediate;

b) deprotecting the cysteine protease inhibitor intermediate; and c) coupling the cysteine protease inhibitor intermediate with an N-protected X amino acid.

31. A method of making a cysteine protease inhibitor of the formula:

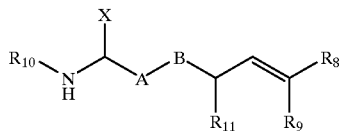

$R_{10}$ is hydrogen, a peptide amino end blocking group, a peptide residue with or without an amino end blocking group, a single amino acid with or without an amino end blocking group, or a label, wherein said amino end blocking group is selected from the group consisting of alkoxy-ω-oxoalkanoyl of 2 to 10 carbon atoms, alkoxycarbonyl of 2 to 10 carbon atoms, alkanoyl of 2 to 10 carbon atoms, cycloalkylcarbonyl of 4 to 8 carbon atoms, carbamoyl, alkylcarbamoyl, dialkylcarbamoyl, benzoyl, alkylsulfonyl of 1 to 10 carbon atoms, and wherein said label is selected from the group consisting of isotopic labels, immune labels, colored labels and fluorescent labels;

X and $R_{11}$ are amino acid side chains in the (R) or (S) configuration;

A—B is a peptide linkage or peptidomimetic linkage;

$R_8$ is a five or six membered homocyclic aromatic ring with at least one substituted group selected from EWM, a MDG, and DG, wherein EWM is an ester, sulfone, carboxylate, amide, phosphonate, ketone, nitrile, nitro compound, sulfonate, sulfoxide, sulfonamide, sulfinamide, or sulfoximine; MDG is $NO_2$, $SO_3H$, $SO_2R$, SOR, $SO_2NH_2$, $SO_2NHR$, $SO_2N(R)_2$, $SONH_2$, SONHR, $SON(R)_2$, CN, $PO_3H$, $P(O)(OR)_2$, P(O)OR, OH, COOH, COR, COOR, or $NRRR^+$, wherein each R is independently an aryl, alkyl, or aralkyl; and DG is a halogen;

$R_9$ is methyl or a peptide; and wherein the second order rate constant for inhibition of a cysteine protease with said inhibitor ($k_{irr}/K_I$) is at least about 1000 $M^{-1}sec^{-1}$, said method comprising:

a) coupling a protected α-amino $R_{11}$ aldehyde with a Wadsworth-Emmons reagent containing said $R_8$ and $R_9$ groups to form a cysteine protease inhibitor intermediate;

b) deprotecting the cysteine protease inhibitor intermediate; and c) coupling the cysteine protease inhibitor intermediate with an N-protected X amino acid.

32. A method of making a cysteine protease inhibitor of the formula:

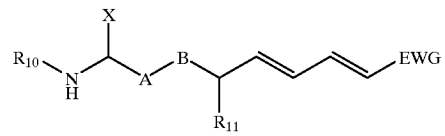

wherein $R_{10}$ is hydrogen, a peptide amino end blocking group, a peptide residue with or without an amino end blocking group, a single amino acid with or without an amino end blocking group or a label, wherein said amino end blocking group is selected from the group consisting of alkoxy-ω-oxoalkanoyl of 2 to 10 carbons, alkoxycarbonyl of 2 to 10 carbons, alkanoyl of 2 to 10 carbons, cycloalkylcarbonyl of 4 to 8 carbons, carbamoyl, alkylcarbamoyl, dialkylcarbamoyl, benzoyl, or alkylsulfonyl of 1 to 10 carbons, and wherein said label is selected from the group consisting of isotopic labels, immune labels, colored labels and fluorescent labels;

X and $R_{11}$ are amino acid side chains in the (R) or (S) configuration;

A—B is a peptide linkage or peptidomimetic linkage;

EWG represents an ester, a sulfone, carboxylate, phosphonate, an amide, a ketone, a nitrile, a sulfoxide, a sulfoxamine, a five or six membered homocyclic or heterocyclic aromatic ring with at least one substituted group selected from EWM, MDG, and DG, wherein EWM is an ester, sulfone, carboxylate, amide, phosphonate, ketone, nitrile, nitro compound, sulfonate, sulfoxide, sulfonamide, sulfinamide, or sulfoximine; MDG is $NO_2$, $SO_3H$, $SO_2R$, SOR, $SO_2NH_2$, $SO_2NHR$, $SO_2N(R)_2H$, $SONH_2$, SONHR, $SON(R)_2$, CN, $PO_3H$, $P(O)(OR)_2$, P(O)OR, OH, COOH, COR, COOR, or $NRRR^+$, wherein each R is independently an aryl, alkyl, or aralkyl; and DG is a halogen; and wherein the second order rate constant for inhibition of a cysteine protease with said inhibitor ($k_{irr}/K_I$) is at least about 1000 $M^{-1}sec^{-1}$, said method comprising:

a) coupling a protected α-amino $R_{11}$ vinylogous aldehyde with a Wadsworth-Emmons reagent containing an EWG to form a diene cysteine protease inhibitor intermediate;

b) deprotecting the diene cysteine protease inhibitor intermediate; and c) coupling the diene cysteine protease inhibitor intermediate with an N-protected "X" amino acid.

* * * * *